United States Patent
Chiu et al.

(10) Patent No.: US 10,514,381 B2
(45) Date of Patent: Dec. 24, 2019

(54) POLYMER DOT COMPOSITIONS AND RELATED METHODS

(71) Applicant: University of Washington through its Center for Commercialization, Seattle, WA (US)

(72) Inventors: Daniel T. Chiu, Seattle, WA (US); Wei Sun, Seattle, WA (US); Jiangbo Yu, Seattle, WA (US); Changfeng Wu, Changchun (CN); Fangmao Ye, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 693 days.

(21) Appl. No.: 14/774,971

(22) PCT Filed: Mar. 14, 2014

(86) PCT No.: PCT/US2014/028846
§ 371 (c)(1),
(2) Date: Sep. 11, 2015

(87) PCT Pub. No.: WO2014/153051
PCT Pub. Date: Sep. 25, 2014

(65) Prior Publication Data
US 2016/0018395 A1 Jan. 21, 2016

Related U.S. Application Data

(60) Provisional application No. 61/785,293, filed on Mar. 14, 2013.

(51) Int. Cl.
*G01N 33/58* (2006.01)
*C09K 11/02* (2006.01)
(Continued)

(52) U.S. Cl.
CPC ....... *G01N 33/54393* (2013.01); *C08G 61/02* (2013.01); *C08G 73/00* (2013.01);
(Continued)

(58) Field of Classification Search
CPC .......................... C09K 11/025; G01N 33/587
See application file for complete search history.

(56) References Cited

U.S. PATENT DOCUMENTS

| 4,774,339 A | 9/1988 | Haugland et al. |
| 4,946,778 A | 8/1990 | Ladner et al. |

(Continued)

FOREIGN PATENT DOCUMENTS

| CN | 1541136 A | 10/2004 |
| CN | 101302353 A | 11/2008 |

(Continued)

OTHER PUBLICATIONS

Corrected Notice of Allowability dated Dec. 1, 2017 for U.S. Appl. No. 13/508,981.

(Continued)

*Primary Examiner* — Tracy Vivlemore
*Assistant Examiner* — Nam P Nguyen
(74) *Attorney, Agent, or Firm* — Christensen O'Connor Johnson Kindness PLLC

(57) ABSTRACT

Lyophilized chromophoric polymer dot compositions are provided. Also disclosed are methods of making and using the lyophilized compositions, methods of dispersing the lyophilized compositions in aqueous solutions and kits supplying the compositions.

22 Claims, 10 Drawing Sheets

(51) Int. Cl.
*G01N 33/543* (2006.01)
*C08G 61/02* (2006.01)
*C08G 73/00* (2006.01)
*C08G 75/32* (2006.01)
*G01N 33/533* (2006.01)

(52) U.S. Cl.
CPC .......... *C08G 75/32* (2013.01); *G01N 33/533* (2013.01); *G01N 33/582* (2013.01); *G01N 33/588* (2013.01); *C08G 2261/11* (2013.01); *C08G 2261/18* (2013.01); *G01N 2650/00* (2013.01); *Y10T 428/2982* (2015.01)

(56) References Cited

U.S. PATENT DOCUMENTS

| | | | |
|---|---|---|---|
| 5,723,218 | A | 3/1998 | Haugland et al. |
| 6,417,402 | B1 | 7/2002 | Das et al. |
| 7,432,298 | B2 | 10/2008 | Lam et al. |
| 7,462,325 | B2 | 12/2008 | Hancock et al. |
| 7,521,232 | B2 | 4/2009 | Moon |
| 7,985,426 | B1 * | 7/2011 | Sung ............ A61K 9/5153 424/489 |
| 8,367,042 | B2 | 2/2013 | Kim et al. |
| 9,382,473 | B2 | 7/2016 | Chiu et al. |
| 9,797,840 | B2 | 10/2017 | Chiu et al. |
| 9,810,693 | B2 | 11/2017 | Chiu et al. |
| 9,849,197 | B2 * | 12/2017 | Saji ............ A61K 49/0032 |
| 10,067,139 | B2 | 9/2018 | Chiu et al. |
| 10,150,841 | B2 | 12/2018 | Chiu et al. |
| 2002/0045045 | A1 | 4/2002 | Adams et al. |
| 2004/0018379 | A1 | 1/2004 | Kinlen |
| 2004/0101822 | A1 | 5/2004 | Wiesner et al. |
| 2004/0131886 | A1 | 7/2004 | Marrocco et al. |
| 2005/0019265 | A1 | 1/2005 | Hammer et al. |
| 2005/0171289 | A1 | 8/2005 | Kataoka et al. |
| 2005/0255044 | A1 | 11/2005 | Lomnes et al. |
| 2006/0127929 | A1 | 6/2006 | Swager et al. |
| 2007/0031490 | A1 | 2/2007 | Loebenberg et al. |
| 2007/0224345 | A1 | 9/2007 | Metz et al. |
| 2008/0081192 | A1 | 4/2008 | Goh et al. |
| 2008/0085566 | A1 | 4/2008 | Swager et al. |
| 2008/0178763 | A1 | 7/2008 | Schwartz et al. |
| 2008/0199700 | A1 | 8/2008 | Anderson et al. |
| 2008/0242806 | A1 | 10/2008 | Chen et al. |
| 2009/0075295 | A1 | 3/2009 | Lindsey |
| 2009/0130665 | A1 | 5/2009 | Sleiman et al. |
| 2009/0220434 | A1 | 9/2009 | Sharma |
| 2010/0016472 | A1 | 1/2010 | Wang et al. |
| 2010/0098902 | A1 | 4/2010 | Kotov et al. |
| 2010/0290999 | A1 | 11/2010 | Kim et al. |
| 2011/0159605 | A1 | 6/2011 | Whitten et al. |
| 2011/0278503 | A1 | 11/2011 | Janczewski et al. |
| 2011/0278536 | A1 | 11/2011 | Walker et al. |
| 2012/0015190 | A1 | 1/2012 | Goh et al. |
| 2012/0175571 | A1 * | 7/2012 | Sarkar ............ B82Y 30/00 252/582 |
| 2012/0282632 | A1 | 11/2012 | Chin et al. |
| 2013/0234067 | A1 | 9/2013 | Chiu et al. |
| 2013/0234068 | A1 | 9/2013 | Chin et al. |
| 2013/0266957 | A1 | 10/2013 | Chiu et al. |
| 2014/0302516 | A1 | 10/2014 | Chin et al. |
| 2014/0350183 | A1 | 11/2014 | Chin et al. |
| 2015/0037259 | A1 | 2/2015 | Chin et al. |
| 2016/0161475 | A1 | 6/2016 | Chiu et al. |
| 2016/0341737 | A1 | 11/2016 | Chiu et al. |

FOREIGN PATENT DOCUMENTS

| | | |
|---|---|---|
| CN | 102791827 A | 11/2012 |
| EP | 2251043 A2 | 11/2010 |
| JP | 2006525527 A | 11/2006 |
| JP | 2013168424 A | 8/2013 |
| WO | WO 2007/027159 A1 | 3/2007 |
| WO | WO 2007/095506 A1 | 8/2007 |
| WO | WO 2008/063378 A2 | 5/2008 |
| WO | WO 2009/051560 A1 | 4/2009 |
| WO | WO 2009/107859 A2 | 9/2009 |
| WO | WO 2010/006753 A2 | 1/2010 |
| WO | WO-2010075512 A1 | 7/2010 |
| WO | WO-2010075514 A1 | 7/2010 |
| WO | WO 2010/099273 A1 | 9/2010 |
| WO | WO 2011/057295 A2 | 5/2011 |
| WO | WO 2012/054525 A2 | 4/2012 |
| WO | WO-2012118136 A1 * | 9/2012 ............ A61K 49/00 |
| WO | WO 2013/101902 A2 | 7/2013 |
| WO | WO-2013116614 A1 | 8/2013 |
| WO | WO-2014153051 A1 | 9/2014 |

OTHER PUBLICATIONS

Greenham, et al., Measurement of Absolute Photoluminescence Quantum Efficiencies in Conjugated Polymers, Chemical Physics Letters, Jul. 14, 1995, 241(1995) 89-96.
Murcia, et al., Biofunctionalization of Fluorescent Nanoparticles, Nanotechnologies for the Life Sciences, 2005, vol. 1, 40 pages.
Notice of allowance dated Jun. 16, 2017 for U.S. Appl. No. 13/687,813.
Notice of allowance dated Jun. 23, 2017 for U.S. Appl. No. 13/865,942.
Notice of allowance dated Aug. 29, 2017 for U.S. Appl. No. 13/508,981.
Notice of Allowance dated Oct. 19, 2017 for U.S. Appl. No. 13/508,981.
Office action dated Jun. 6, 2017 for JP Application No. 2016-151438.
Office action dated Jun. 15, 2017 for CN Application No. 201180060824.2.
Office action dated Jun. 23, 2017 for CN Application No. 201480028351.1.
Office action dated Jul. 26, 2017 for CN Application No. 201280070923.3.
Office action dated Jul. 28, 2017 for EP Application No. 14770843.
Office action dated Sep. 21, 2017 for EP Application No. 15175146.8.
Office action dated Sep. 22, 2017 for EP Application No. 11835019.8.
Office Action dated Oct. 10, 2017 for U.S. Appl. No. 14/366,863.
Office Action dated Nov. 24, 2017 for CN Patent Application No. 201180060824.2.
Office Action dated Nov. 30, 2017 for U.S. Appl. No. 14/373,835.
Benstead, et al. Addressing fluorescence and liquid crystal behaviour in multi-mesogenic BODIPY materials. New Journal of Chemistry. 2011; 35(7):1410-1417.
European search report and opinion dated May 31, 2016 for EP Application No. 12861954.
Greenham et al., Efficient light-emitting diodes based on polymers with high electron affinities, Nature, vol. 365:628-630, published Oct. 14, 1993, print retrieved on Oct. 10, 2016.
Huyal, et al., White emitting polyfluorene functionalized with azide hybridized on near-UV light emitting diode for high color rendering index, Optics Express, Jan. 21, 2008, 16(2):1115-24.
Meng, et al. Color tuning of polyfluorene emission with BODIPY monomers, Macromolecules 2009, 42:1995-2001.
Nagai, et al. Highly luminescent BODIPY-based organoboron polymer exhibiting supramolecular self-assemble structure. J Am Chem Soc. Nov. 19, 2008;130(46):15276-8. doi: 10.1021/ja806939w.
Nagai, et al. Organoboron conjugated polymers. In Conjugated Polymer Synthesis: Methods and reactions. Ed. Yoshiki Chujo. Wiley-VCH Verlag GmbH & Co KGaA, Weinheim. 2010. 195-214.
Office action dated Jan. 29, 2016 for AU Application 2012362466.
Office action dated Feb. 19, 2016 for CN Application 201280070923.3.
Office action dated Mar. 8, 2017 for AU Application No. 2015204342.
Office action dated Mar. 15, 2017 for JP Application No. 2013-535014.
Office action dated Mar. 29, 2016 for JP Application No. 2012-538915.

(56) References Cited

OTHER PUBLICATIONS

Office action dated Mar. 30, 2017 for U.S. Appl. No. 14/373,835.
Office action dated Apr. 5, 2017 for EP Application No. 15175146.8.
Office action dated Apr. 28, 2017 for U.S. Appl. No. 13/865,942.
Office action dated May 16, 2016 for U.S. Appl. No. 14/373,835.
Office action dated May 20, 2016 for EP Application No. 10829306.9.
Office action dated May 29, 2017 for CA Application No. 2,814,790.
Office action dated Sep. 26, 2016 for CN Application No. 201480028351.1.
Office action dated Sep. 27, 2016 for EP Application No. 11835019.8.
Office action dated Sep. 27, 2016 for JP Application 2014-550455.
Office action dated Oct. 20, 2016 for U.S. Appl. No. 13/687,813.
Office action dated Nov. 4, 2016 for CN Application No. 201280070923.3.
Office action dated Dec. 29, 2016 for U.S. Appl. No. 13/865,942.
Office action dated Jan. 30, 2017 for AU Application No. 2012362466.
Office action dated Feb. 22, 2017 for U.S. Appl. No. 13/508,981.
Office action dated Mar. 1, 2017 for U.S. Appl. No. 14/366,863.
Office action dated Sep. 13, 2016 for U.S. Appl. No. 14/373,835.
Park, et al., White-Emitting Conjugated Polymer Nanoparticles with Cross-Linked Shell for Mechanical Stability and Controllable photometric Properties in Color-Conversion LED Applications, ACS Nano, 2011, 5(4):2483-92.
Riddle, et al. Signal Amplifying Resonance Energy Transfer: A Dynamic Multichromophore Array for Allosteric Switching. Angewandte Chemie International Edition. 2007; 46(37):7019-7022.
Yao, et al., Fluorescent Nanoparticles Comprising Amphiphilic Rod-Coil Graft Copolymers, Macromolecules, 2008, 41:1438-43.
Zhang, et al., Synthesis and characterization of a novel water-soluble block copolymer with a rod-coil structure, Materials Letters 60, (2006), pp. 679-684.
Zhu, et al. Efficient tuning nonlinear optical properties: Synthesis and characterization of a series of novel poly (aryleneethynylene) s co-containing BODIPY. Journal of Polymer Science Part A: Polymer Chemistry. 2008; 46(22):7401-7410.
Abdelwahed, et al. Freeze-drying of nanoparticles: formulation, process and storage considerations. Adv Drug Deliv Rev. Dec. 30, 2006;58(15):1688-713.
European search report and opinion dated Sep. 8, 2016 for EP Application No. 14770843.2.
Rong, et al. Multicolor fluorescent semiconducting polymer dots with narrow emissions and high brightness. Acs Nano. 2013; 7(1)L376-384.
Sun, et al. Lyophilization of semiconducting polymer dot bioconjugates. Anal Chem. May 7, 2013;85(9):4316-20. doi: 10.1021/ac4007123. Epub Apr. 19, 2013.
European office action dated Mar. 2, 2016 for EP Application No. 11835019.8.
Office action dated Feb. 11, 2016 for U.S. Appl. No. 13/865,942.
Australian examination report dated Apr. 8, 2016 for AU Application 2015204342.
Chinese office action dated Sep. 26, 2016 for CN Application No. 20118006824.2.
CN 201610969596.5 First Office Action dated Jan. 22, 2018. (w/ English translation).
JP 2016-502922 Office Action dated Feb. 6, 2018. (w/ English translation).
EP 12861954.1 Office Action dated Jan. 26, 2018.
U.S. Appl. No. 13/508,981 Office Action dated Mar. 28, 2018.
Abbel, et al. Multicolour self-assembled particles of fluorene-based bolaamphiphiles. Chem Commun (Camb). Apr. 7, 2009;(13):1697-9. doi: 10.1039/b822943k. Epub Feb. 17, 2009.
Achari, et al. 1.67-A X-ray structure of the B2 immunoglobulin-binding domain of streptococcal protein G and comparison to the NMR structure of the B1 domain Biochemistry. Nov. 3, 1992;31(43):10449-57.
Agard, et al. A comparative study of bioorthogonal reactions with azides. ACS Chem Biol. Nov. 21, 2006;1(10):644-8.
Akerstrom, et al. A physicochemical study of protein G, a molecule with unique immunoglobulin G-binding properties. J Biol Chem. Aug. 5, 1986;261(22):10240-7.
Alivistatos, et al. Quantum dots as cellular probes. Annu Rev Biomed Eng. 2005;7:55-76.
Ausborn, et al. The protective effect of free and membrane-bound cryoprotectants during freezing and freeze-drying of liposomes. Journal of Controlled Release. 1994; 30:105-116.
Baler, et al. Fluorescent conjugated polymer nanoparticles by polymerization in miniemulsion. J Am Chem Soc. Oct. 14, 2009;131(40):14267-73. doi: 10.1021/ja905077c.
Berlier, et al. Quantitative comparison of long-wavelength Alexa Fluor dyes to Cy dyes: fluorescence of the dyes and their bioconjugates. J Histochem Cytochem. Dec. 2003;51(12):1699-712.
Bernardin, et al. Copper-free click chemistry for highly luminescent quantum dot conjugates: application to in vivo metabolic imaging. Bioconjug Chem. Apr. 21, 2010;21(4):583-8. doi: 10.1021/bc900564w.
Best. Click chemistry and bioorthogonal reactions: unprecedented selectivity in the labeling of biological molecules. Biochemistry. Jul. 21, 2009;48(28):6571-84. doi: 10.1021/bi9007726.
Bird, et al. Single-chain antigen-binding proteins. Science. Oct. 21, 1988;242(4877):423-6.
Boyere, et al. Elaboration of drug nanocarriers based on a glucosamine labeled amphiphilic polymer. Polymer Chemistry. 2014; 5:3030-3037.
Breidenbach, et al. Targeted metabolic labeling of yeast N-glycans with unnatural sugars. Proc Natl Acad Sci U S A. Mar. 2, 2010;107(9):3988-93. doi: 10.1073/pnas.0911247107. Epub Feb. 8, 2010.
Bruchez, et al. Semiconductor nanocrystals as fluorescent biological labels. Science. Sep. 25, 1998;281(5385):2013-6.
Caruso. Nanoengineering of Particle Surfaces. Adv. Mater. 2001; 13:11-22.
Chalfie, et al. Green fluorescent protein as a marker for gene expression. Science. Feb. 11, 1994;263(5148):802-5.
Chan, et al. Copper(II) and iron(II) ion sensing with semiconducting polymer dots. Chem Commun (Camb). Mar. 14, 2011;47(10):2820-2. doi: 10.1039/c0cc04929h. Epub Jan. 14, 2011.
Chan, et al. Development of ultrabright semiconducting polymer dots for ratio metric pH sensing. Anal Chem. Feb. 15, 2011;83(4):1448-55. doi: 10.1021/ac103140x. Epub Jan. 18, 2011.
Chan, et al. Hybrid semiconducting polymer dot-quantum dot with narrow-band emission, near-infrared fluorescence, and high brightness. J Am Chem Soc. May 2, 2012;134(17):7309-12. doi: 10.1021/ja3022973. Epub Apr. 23, 2012.
Chan, et al. Quantum dot bioconjugates for ultrasensitive nonisotopic detection. Science. Sep. 25, 1998;281(5385):2016-8.
Chan, et al. Ultrasensitive copper(II) detection using plasmon-enhanced and photo-brightened luminescence of CdSe quantum dots. Anal Chem. May 1, 2010;82(9):3671-8. doi: 10.1021/ac902985p.
Chen, et al. Highly sensitive biological and chemical sensors based on reversible fluorescence quenching in a conjugated polymer. Proc Natl Acad Sci U S A. Oct. 26, 1999;96(22):12287-92.
Choi, et al. Design considerations for tumour-targeted nanoparticles. Nat Nanotechnol. Jan. 2010;5(1):42-7. doi: 10.1038/nnano.2009.314. Epub Nov. 1, 2009.
Choi, et al. Renal clearance of quantum dots. Nat Biotechnol. Oct. 2007;25(10):1165-70. Epub Sep. 23, 2007.
Clafton, et al. Chemical defects in the highly fluorescent conjugated polymer dots. Langmuir. Dec. 7, 2010;26(23):17785-9. doi: 10.1021/1a103063p. Epub Nov. 11, 2010.
Collini, et al. Coherent intrachain energy migration in a conjugated polymer at room temperature. Science. Jan. 16, 2009;323(5912):369-73. doi: 10.1126/science.1164016.
Derfus, et al. Probing the Cytotoxicity of Semiconductor Quantum Dots. Nano Letters. 2004; 4(1):11-18.
Dieterich, et al. Selective identification of newly synthesized proteins in mammalian cells using bioorthogonal noncanonical amino

(56) References Cited

OTHER PUBLICATIONS acid tagging (BONCAT). Proc Natl Acad Sci U S A. Jun. 20, 2006;103(25):9482-7. Epub Jun. 12, 2006.
Dube, et al. Probing mucin-type O-linked glycosylation in living animals. Proc Natl Acad Sci U S A. Mar. 28, 2006;103(13):4819-24. Epub Mar. 20, 2006.
European search report and opinion dated Mar. 19, 2014 for EP Application No. 11835019.8.
European search report and opinion dated Aug. 12, 2015 for EP Application No. 15175146.8.
European search report and opinion dated Sep. 18, 2013 for EP Application No. 10829306.9.
European search report and opinion dated Oct. 8, 2015 for EP Application No. 13743132.6.
Fan, et al. Beyond superquenching: hyper-efficient energy transfer from conjugated polymers to gold nanoparticles. Proc Natl Acad Sci U S A. May 27, 2003;100(11):6297-301. Epub May 15, 2003.
Fernandez-Suarez, et al. Fluorescent probes for super-resolution imaging in living cells. Nat Rev Mol Cell Biol. Dec. 3009;9(12):929-43. doi: 10.1038/nrm2531. Epub Nov. 12, 2008.
Fernando, et al. Mechanism of cellular uptake of highly fluorescent conjugated polymer nanoparticles. Biomacromolecules. Oct. 11, 2010;11(10):2675-82. doi: 10.1021/bm1007103.
Friend, et al. Electroluminescence in conjugated polymers. Nature. 1999; 397:121-128.
Giepmans, et al. The fluorescent toolbox for assessing protein location and function. Science. Apr. 14, 2006;312(5771):217-24.
Green. Avidin and streptavidin. Methods Enzymol. Wilchek and Bayer. New York, Academic Press, Inc. 1990;184:51-67.
Gunes, et al. Conjugated polymer-based organic solar cells. Chem Rev. Apr. 2007;107(4):1324-38.
Han, et al. Development of a bioorthogonal and highly efficient conjugation method for quantum dots using tetrazine-norbornene cycloaddition. J Am Chem Soc. Jun. 16, 2010;132(23):7838-9. doi: 10.1021/ja101677r.
Hashim, et al. Luminescent quantum-dot-sized conjugated polymer nanoparticles—nanoparticle formation in miniemulsion system. Journal of Materials Chemistry. 2011; 21: 1797-1803.
Hermanson. Bioconjugate techniques, Academic Press, San Diego, 1996; Ch 13, 570-591.
Hou, et al. Novel red-emitting fluorene-based copolymers. Journal of Materials Chemistry. 2002; 12:2887-2892.
Hou, et al. Synthesis and electroluminescent properties of high-efficiency saturated red emitter based on copolymers from fluorene and 4,7-di(4-hexylthien-2-y1)-2,1,3-benzothiadiazole, Macromolecules. 2004; 37:6299-6305.
Howarth, et al. Monovalent, reduced-size quantum dots for imaging receptors on living cells. Nat Methods. May 2008;5(5):397-9. doi: 10.1038/nmeth.1206. Epub Apr. 20, 2008.
Howes, et al. Colloidal and optical stability of PEG-capped and phospholipid-encapsulated semiconducting polymer nanospheres in different aqueous media. Photochem Photobiol Sci. Aug. 2010;9(8):1159-66. doi: 10.1039/c0pp00106f. Epub Jun. 29, 2010.
Howes, et al. Magnetic conjugated polymer nanoparticles as bimodal imaging agents. J Am Chem Soc. Jul. 21, 2010;132(28):9833-42. doi: 10.1021/ja1031634.
Howes, et al. Phospholipid encapsulated semiconducting polymer nanoparticles: their use in cell imaging and protein attachment. J Am Chem Soc. Mar. 24, 2010;132(11):3989-96. doi: 10.1021/ja1002179.
Howes, et al. Synthesis, characterisation and intracellular imaging of PEG capped BEHP-PPV nanospheres. Chem Commun (Camb). May 14, 2009;(18):2490-2. doi: 10.1039/b903405f. Epub Apr. 2, 2009.
International preliminary report on patentability dated Apr. 23, 2013 for PCT/US2011/056768.
International search report and written opinion dated Mar. 27, 2013 for PCT/US2012/071767.
International search report and written opinion dated Apr. 9, 2013 for PCT/US2013/024300.
International search report and written opinion dated Jun. 26, 2012 for PCT/US2011/056768.
International search report and written opinion dated Jul. 28, 2011 for PCT/US2010/056079.
International search report and written opinion dated Aug. 22, 2014 for PCT/US2014/028846.
Jin, et al. Generation of functionalized and robust semiconducting polymer dots with polyelectrolytes. Chem Commun (Camb). Mar. 28, 2012;48(26):3161-3. doi: 10.1039/c2cc17703j. Epub Feb. 20, 2012.
Jin, et al. Near-infrared fluorescent dye-doped semiconducting polymer dots. ACS Nano. Feb. 22. 2011;5(2):1468-75. doi: 10.1021/nn103304m. Epub Jan. 31, 2011.
Jin, et al. Silica Nanoparticles with Continuously Tunable Sizes: Synthesis and Size Effects on Cellular Imaging. Chem. Mater. 2008, 20:4411-4419.
Johnston, et al. Layer-by-layer engineered capsules and their applications. Curr. Opin. Colloid Interface Sci. 2006; 11:203-209.
Kaeser, et al. Fluorescent nanoparticles based on self-assembled pi-conjugated systems. Adv Mater. Jul. 27, 2010;22(28):2985-97. doi: 10.1002/adma.201000427.
Kietzke, et al. Novel approaches to polymer blends based on polymer nanoparticles. Nat Mater. Jun. 2003;2(6):408-12.
Kim, et al. Conjugated polymer nanoparticles for biomedical in vivo imaging. Chem Commun (Camb). Mar. 14, 2010;46(10):1617-9. doi: 10.1039/b923309a. Epub Jan. 12, 2010.
Kolb, et al. Click Chemistry: Diverse Chemical Function from a Few Good Reactions. w Chem Int Ed Engl. Jun. 1, 2001;40(11):2004-2021.
Kolb, et al. The growing impact of click chemistry on drug discovery. Drug Discov Today. Dec. 15, 2003;8(24):1128-37.
Kumar, et al. Photon antibunching from oriented semiconducting polymer nanostructures. J Am Chem Soc. Mar. 24, 2004;126(11):3376-7.
Laughlin, et al. Imaging the glycome. Proc Natl Acad Sci U S A. Jan. 6, 2009;106(1):12-7. doi: 10.1073/pnas.0811481106. Epub Dec. 22, 2008.
Lee, et al. Recent advances in fluorescent and colorimetric conjugated polymer-based biosensors. Analyst. Sep. 2010;135(9):2179-89. doi: 10.1039/c0an00239a. Epub Jun. 11, 2010.
Li, et al. Polymer encapsulated conjugated polymer nanoparticles for fluorescence bioimaging. Journal of Materials Chemistry 2012; 22:1257-1264.
McCafferty, et al. Phage antibodies: filamentous phage displaying antibody variable domains Nature. Dec. 6, 1990;348(6301):552-4.
Michalet, et al. Quantum dots for live cells, in vivo imaging, and diagnostics. Science. Jan. 28. 2005;307(5709):538-44.
Moon, et al. Conjugated polymer nanoparticles for small interfering RNA delivery. Chem Commun (Camb). Aug. 7, 2011;47(29):8370-2. doi: 10.1039/c1cc10991j. Epub Jun. 22, 2011.
Moon, et al. Live-cell-permeable poly(p-phenylene ethynylene). Angew Chem Int Ed Engl. 2007;46(43):8223-5.
Moses, et al. The growing applications of click chemistry. Chem Soc Rev. Aug. 2007;36(8):1249-62. Epub May 3, 2007.
Nirmal, et al. Fluorescence intermittency in single cadmium selenide nanocrystals. Nature. 1996; 383:802-804. doi:10.1038/383802a0.
Palacios, et al. Charging and discharging of single conjugated-polymer nanoparticles. Nat Mater. Sep. 2007;6(9):680-5. Epub Jul. 22, 2007.
Pecher, et al. Nanoparticles of conjugated polymers. Chem Rev. Oct. 13. 2010;110(10):6260-79. doi: 10.1021/cr100132y.
Pepperkok, et al. High-throughput fluorescence microscopy for systems biology. Nat Rev Mol Cell Biol. Sep. 2006;7(9):690-6. Epub Jul. 19, 2006.
Poon, et al. Controlling in vivo stability and biodistribution in electrostatically assembled nanoparticles for systemic delivery. Nano Lett. May 11, 2011;11(5):2096-103. doi: 10.1021/nl200636r. Epub Apr. 27, 2011.
Poon, et al. Layer-by-layer nanoparticles with a pH-sheddable layer for in vivo targeting of tumor hypoxia. ACS Nano. Jun. 28, 2011;5(6):4284-92. doi: 10.1021/nn200876f. Epub Apr. 29, 2011.

(56) References Cited

OTHER PUBLICATIONS

Pras, et al. Photoluminescence of 2,7-poly(9,9-dialkylfluorene-co-fluorenone) nanoparticles: effect of particle size and inert polymer addition. Langmuir. Sep. 21, 2010;26(18):14437-42. doi: 10.1021/la1011742.
Prescher, et al. Chemical remodelling of cell surfaces in living animals Nature. Aug. 19, 2004;430(7002):873-7.
Prescher, et al. Chemistry in living systems. Nat Chem Biol. Jun. 2005;1(1):13-21.
Pu, et al. Fluorescent conjugated polyelectroltyes for bioimaging. Advanced Functional Materials. 2011; 21:3408-3423.
Pu, et al. Fluorescent single-molecular core—shell nanospheres of hypethranched conjugated polyelectrolyte for live-cell imaging. Chem. Mater. 2009;21:3816-3822.
Office action dated Feb. 2, 2016 for CN Application No. 201180068242.
Office action dated Feb. 4, 2015 for CN Application No. 201180068242.
Office action dated Apr. 28, 2014 for AU Application No. 2011317142.
Office action dated May 30, 2014 for CN Application No. 201180068242.
Office action dated Aug. 4, 2015 for CN Application No. 201180068242.
Office action dated Dec. 3, 2015 for JP Application No. 2013-535014.
Que, et al. Metals in neurobiology: probing their chemistry and biology with molecular imaging. Chem Rev. May 2008;108(5):1517-49. doi: 10.1021/cr078203u. Epub Apr. 22, 2008.
Rahim, et al. Conjugated Polymer Nanoparticles for Two-Photon Imaging of Endothelial Cells in a Tissue Model. Adv. Mater. 2009; 21(34):3492-3496.
Resch-Genger, et al. Quantum dots versus organic dyes as fluorescent labels. Nat Methods. Sep. 2008;5(9):763-75. doi: 10.1038/nmeth.1248.
Sadtler, et al. Selective facet reactivity during cation exchange in cadmium sulfide nanorods. J Am Chem Soc. Apr. 15, 2009;131(14):5285-93. doi: 10.1021/ja809854q.
Sigma Aldrich. Product Information Triton X-1 00. Apr. 21, 1999. Retrieved at http://www.sigmaaldrich.com/content!dam/sigmaaldrich/docs/Sigma/Product_Information_Sheet/1 /t8532pis.pdf on Mar. 14, 2014.
Sletten, et al. Bioorthogonal chemistry: fishing for selectivity in a sea of functionality. Angew Chem Int Ed Engl. 2009;48(38):6974-98. doi: 10.1002/anie.200900942.
Smith, et al. Investigating lyophilization of lipid nanocapsules with fluorescence correlation spectroscopy. Investigating lyophilization of lipid nanocapsules with fluorescence correlation spectroscopy.
Speers, et al. Activity-based protein profiling in vivo using a copper(i)-catalyzed azide-alkyne [3+2] cycloaddition. J Am Chem Soc. Apr. 23, 2003;125(16):4686-7.
Szymanski, et al. Single molecule nanoparticles of the conjugated polymer MEH-PPV, preparation and characterization by near-field scanning optical microscopy. J Phys Chem B. May 12, 2005;109(18):8543-6.
Thomas, et al. Chemical sensors based on amplifying fluorescent conjugated polymers. Chem Rev. Apr. 2007;107(4):1339-86. Epub Mar. 27, 2007.
Tian, et al. Amplified energy transfer in conjugated polymer nanoparticle tags and sensors. Nanoscale. Oct. 2010;2(10):1999-2011. doi: 10.1039/c0nr00322k. Epub Aug. 10, 2010.
Thivierge, et al. Brilliant BODIPY-fluorene Copolymers With Dispersed Absorption and Emission Maxima Macromolecules. May 24, 2011;44(10):4012-4015.
Tsien. The green fluorescent protein. Annu Rev Biochem. 1998;67:509-44.
Tuncel, et al. Conjugated polymer nanoparticles. Nanoscale. Apr. 2010;2(4):484-94. doi: 10.1039/b9nr00374f. Epub Mar. 6, 2010.
Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.
Wang, et al. Bioconjugation by copper(I)-catalyzed azide-alkyne [3 + 2] cycloaddition. J Am Chem Soc. Mar. 19, 2003;125(11):3192-3.
Wang, et al. Non-blinking semiconductor nanocrystals. Nature. Jun. 4, 2009;459(7247):686-9. doi: 10.1038/nature08072.
Wang, et al. Watching silica nanoparticles glow in the biological world. Anal. Chem. 2006;78(3):646-654.
Wu, et al. Bioconjugation of ultrabright semiconducting polymer dots for specific cellular targeting. J Am Chem Soc. Nov. 3, 2010;132(43):15410-7. doi: 10.1021/ja107196s.
Wu, et al. Conjugated polymer dots for multiphoton fluorescence imaging. J Am Chem Soc. Oct. 31, 2007;129(43):12904-5. Epub Oct. 6, 2007.
Wu, et al. Corrigendum: Immunofluorescent labeling of cancer marker Her2 and other cellular targets with semiconductor quantum dots. Nat Biotechnol. Jan. 2003;21(1):41-6. Epub Dec. 2, 2002.
Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.
Wu, et al. Energy Transfer in a Nanoscale Multichromophoric System: Fluorescent Dye-Doped Conjugated Polymer Nanoparticles. Phys Chem C Nanomater Interfaces. Feb. 14, 2008;112(6):1772-1781.
Wu, et al. Energy transfer mediated fluorescence from blended conjugated polymer nanoparticles. J Phys Chem B. Jul. 27, 2006;110(29):14148-54.
Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.
Wu, et al. Immunofluorescent labeling of cancer marker Her2 and other cellular targets with semiconductor quantum dots. Nat Biotechnol. Jan. 2003;21(1):41-6. Epub Dec. 2, 2002.
Wu, et al. Multicolor conjugated polymer dots for biological fluorescence imaging. ACS Nano. Nov. 25, 2008;2(11):2415-23. doi: 10.1021/nn800590n.
Wu, et al. Preparation and encapsulation of highly fluorescent conjugated polymer nanoparticles. Langmuir. Mar. 28, 2006;22(7):2956-60.
Wu, et al. Ratiometric single-nanoparticle oxygen sensors for biological imaging. Angew Chem Int Ed Engl. 2009;48(15):2741-5. doi: 10.1002/anie.200805894.
Wu, et al. Swelling-controlled polymer phase and fluorescence properties of polyfluorene nanoparticles. Langmuir. Jun. 3, 2008;24(11):5855-61. doi: 10.1021/la8000762. Epub May 7, 2008.
Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.
Wu. Fluorescent conjugated polymer dots for single molecule imaging and sensing application A Dissertation presented to the Graduate School of Clemson University. Dec. 1, 2008. pages 1-182. http://etd.lib.clemson.edu/documents/1239895063/Wu_clemson005D_10023.pdf.
Xie, et al. Luminescent CdSe—ZnSe quantum dots as selective $Cu^{2+}$ probe. Spectrochimica Acta Part A. 2004; 60:2527-2530.
Xing, et al. Bioconjugated quantum dots for multiplexed and quantitative immunohistochemistry. Nat Protoc. 2007;2(5):1152-65.
Yang, et al. Deep-red electroluminescent polymers: Synthesis and characterization of new low-band-gap conjugated copolymers for light-emitting diodes and photovoltaic devices. Macromolecules 2005; 38:244-253.
Yao, et al. Blinking and nonradiant dark fraction of water-soluble quantum dots in aqueous solution. Proc Natl Acad Sci U S A. Oct. 4, 2005;102(40):14284-9. Epub Sep. 16, 2005.
Ye, et al. A compact and highly fluorescent orange-emitting polymer dot for specific subcellular imaging. Chem Commun (Camb). Feb. 7, 2012;48(12):1778-80. doi: 10.1039/c2cc16486h. Epub Jan. 4, 2012.

(56) References Cited

OTHER PUBLICATIONS

Ye, et al. Ratiometric temperature sensing with semiconducting polymer dots. J Am Chem Soc. Jun. 1, 2011;133(21):8146-9. doi: 10.1021/ja202945g. Epub May 11, 2011.
Yu, et al. Nanoscale 3D tracking with conjugated polymer nanoparticles. J Am Chem Soc. Dec. 30, 2009;131(51):18410-4. doi: 10.1021/ja907228q.
Yu, et al. Stable functionalization of small semiconducting polymer dots via covalent cross-linking and their application for specific cellular imaging. Adv Mater. Jul. 10, 2012;24(26):3498-504. doi: 10.1002/adma.201201245. Epub Jun. 11, 2012.
Zhang, et al. Importance of having low-density functional groups for generating high-performance semiconducting polymer dots. ACS Nano. Jun. 26, 2012;6(6):5429-39. doi: 10.1021/nn301308w. Epub May 24, 2012.
Zheng. Detection of the cancer marker CD146 expression in melanoma cells with semiconductor quantum dot label (Abstract). J Biomed Nanotechnol. Aug. 2010;6(4):303-11.
Australian Examination Report dated Jun. 13, 2018 for AU Application No. AU2017204805.
CA2814790 Office Action dated May 28, 2018.
CN 201280070923.3 Fourth Office Action dated Apr. 23, 2018 (w/ English translation).
"CN 201480028351.1 Third Office Action dated Mar. 28, 2018 (w/ English translation)".
"EP 14770843.2 Office Action dated Apr. 13, 2018".
"JP 2016-235598 Office Action dated Mar. 28, 2018 (w/ English translation)".
Notice of allowance dated Jun. 27, 2018 for U.S. Appl. No. 14/366,863.
Notice of allowance dated Jul. 23, 2018 for U.S. Appl. No. 14/366,863.
Notice of allowance dated Aug. 8, 2018 for U.S. Appl. No. 14/373,835.
Notice of allowance dated Sep. 6, 2018 for U.S. Appl. No. 13/508,981.
"U.S. Appl. No. 14/373,835 Notice of Allowance dated Apr. 24, 2018".
Co-pending U.S. Appl. No. 16/041,569, filed Jul. 20, 2018.
Co-pending U.S. Appl. No. 16/209,729, filed Dec. 4, 2018.
European search report with written opinion dated Oct. 24, 2018 for EP Application No. 18193806.
Green, et al. Simple conjugated polymer nanoparticles as biological labels. Proc. R. Soc. A. 2009. 465. 2751-2759; DOI: 10.1098/rspa.2009.0181. Published Jul. 27, 2009.
JP 2016-235598 Office Action dated Oct. 3, 2018 (w/ English translation).
Notice of allowance dated Dec. 26, 2018 for U.S. Appl. No. 13/508,981.
Office action dated Nov. 6, 2018 for EP Application No. 14770843.
Office action dated Dec. 4, 2018 for U.S. Appl. No. 16/041,569.
China National Intellectual Property Administration: Notice on the Second Office Action dated Aug. 23, 2018, issued in corresponding Chinese Application No. 201610969596.5, filed Aug. 6, 2018, 21 pages.
Examination Report No. 1 for Standard Patent Application dated Mar. 29, 2018, issued in corresponding Australian Application No. 2017200592, filed Jun. 10, 2016, 5 pages.
Examination Report No. 2 for Standard Patent Application dated Oct. 25, 2018, issued in corresponding Australian Application No. 2017200592, filed Jun. 10, 2016, 3 pages.
China National Intellectual Property Administration: Notice on the Second Office Action dated Dec. 1, 2014, issued in corresponding Chinese Application No. 201080060982.3, filed Nov. 9, 2010, 12 pages.
China National Intellectual Property Administration: Notice on the First Office Action dated Jan. 14, 2014, issued in corresponding Chinese Application No. 201080060982.3, filed Nov. 9, 2010, 24 pages.
China National Intellectual Property Administration: Notice on the Fourth Office Action dated Jan. 5, 2016, issued in corresponding Chinese Application No. 201080060982.3, filed Nov. 9, 2010, 12 pages.
China National Intellectual Property Administration: Notice on the Third Office Action dated Jul. 31, 2015, issued in corresponding Chinese Application No. 201080060982.3, filed Nov. 9, 2010, 9 pages.
Notice of Reasons for Rejection dated Dec. 26, 2019, issued in corresponding Japanese Application No. 2017-92547, filed Dec. 27, 2019, 11 pages.

* cited by examiner

POLYMER DOT COMPOSITIONS AND RELATED METHODS

CROSS-REFERENCE

This application is a U.S. National Phase Application under 35 U.S.C. § 371 of International Application No. PCT/US2014/028846, filed Mar. 14, 2014, which claims the benefit of U.S. Provisional Application No. 61/785,293, filed Mar. 14, 2013, which application is incorporated herein by reference in its entirety for all purposes.

STATEMENT AS TO FEDERALLY SPONSORED RESEARCH

This disclosure was made with the support of the National Institutes of Health under grant number GM085485. The government may have rights to this disclosure.

BACKGROUND

Fluorescence-based techniques are playing an increasingly important role in the study of biological systems. New fluorescent probes ranging from small organic fluorophores to nanoparticles, such as quantum dots (Qdots), and various forms of genetically encoded green fluorescent proteins (GFPs) have been developed. These fluorescent probes have made new measurements and advances possible but they have their limitations, such as low brightness, insufficient photostability, or toxicity concerns. As a result, there continues to be a need for probes that improve upon the existing fluorescent labels or at least complement them.

Polymer dots (chromophoric polymer dots) have been developed as a new class of fluorescent nanoparticles. Compared to organic dyes and fluorescent proteins, chromophoric polymer dots can possess orders of magnitude greater brightness and are more resistant to photobleaching. When comparing to quantum dots (Qdots), for example, chromophoric polymer dots can be an order of magnitude brighter. Moreover, the dimensions of chromophoric polymer dots can be tuned from several to tens of nanometers without affecting their spectral properties. Chromophoric polymer dots with small sizes are desirable in situations where labeling with large nanoparticles may perturb the native behavior of the tagged biomolecules. The small chromophoric polymer dots may also be useful in crowded cellular or intercellular spaces where they can better penetrate and distribute themselves. Various schemes have been developed to control the surface properties and bioconjugation of chromophoric polymer dots, which have provided use of chromophoric polymer dots for cell-surface and subcellular labeling. In addition, chromophoric polymer dot-based ratiometric sensors have been developed, including ones for pH, temperature, and ions, such as iron and copper.

Although chromophoric polymer dots represent a promising new class of fluorescent probes, there is a continued need to for developing methods and compositions involving the use of chromophoric polymer dots, e.g., methods and compositions for storing chromophoric polymer dots.

SUMMARY

The present disclosure provides compositions of lyophilized chromophoric polymer dots and related methods. For example, the present disclosure includes lyophilized compositions comprising fluorescent nanoparticles, the fluorescent nanoparticles comprising at least one condensed conjugated polymer. The present disclosure also includes a lyophilized composition comprising fluorescent nanoparticles, wherein the fluorescent nanoparticles are lyophilized. Additionally, the present disclosure also includes a method of producing a lyophilized composition, the method comprising, lyophilizing a suspension comprising fluorescent particles, thereby forming the lyophilized composition of fluorescent nanoparticles, wherein the fluorescent nanoparticles are chromophoric polymer dots each including at least one condensed conjugated polymer. For example, the present disclosure also includes a method of producing a lyophilized composition, the method comprising, lyophilizing a suspension comprising fluorescent particles, thereby forming the lyophilized composition of fluorescent nanoparticles, wherein the fluorescent nanoparticles are chromophoric polymer dots comprising a polymer. The present disclosure also includes method for dispersing a lyophilized composition of a nanoparticle comprising, combining a lyophilized composition comprising a fluorescent nanoparticle with an aqueous solution, and agitating the combination to produce a dispersed sample of fluorescent nanoparticle. The present disclosure also includes a lyophilized composition prepared by the method comprising, lyophilizing a suspension comprising fluorescent particles, thereby forming the lyophilized composition of fluorescent nanoparticles, wherein the fluorescent nanoparticles are chromophoric polymer dots comprising a polymer. The present disclosure also includes a kit comprising a lyophilized composition comprising, a fluorescent nanoparticle, an aqueous solution suitable for dispersing the lyophilized composition, a set of instructions describing, combining the lyophilized composition and the aqueous solution of and agitating the combination such that the lyophilized composition becomes dispersed in the aqueous solution.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative cases, in which the principles of the disclosure are utilized, and the accompanying drawings of which:

FIG. 2A depicts the size distribution of chromophoric polymer dots before lyophilization. FIGS. 2B-2D provide size distributions for rehydrated chromophoric polymer dots after lyophilization with (B) 0%, (C) 1%, and (D) 10% sucrose.

FIG. 6A depicts a population of MCF-7 cells belonging to the active gate as shown by the side scatter versus forward scatter plot.

DETAILED DESCRIPTION

Figure 1:
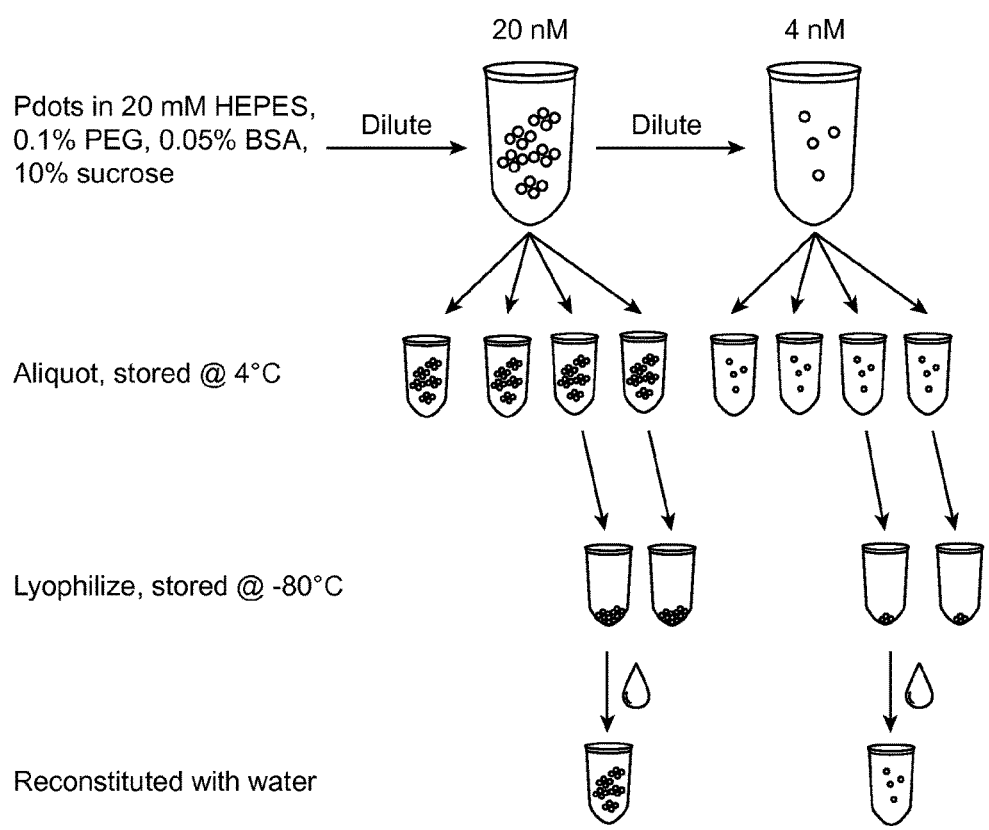
FIG. 1 shows a schematic depicting an experimental procedure, in accordance with some aspects of the present disclosure.

While preferred cases of the present disclosure have been shown and described herein, it is to be understood that the disclosure is not limited to the particular cases of the disclosure described below, as variations of the particular cases may be made and still fall within the scope of the appended claims. It is also to be understood that the terminology employed is for the purpose of describing particular cases of the disclosure, and is not intended to be limiting. Instead, the scope of the present disclosure is established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure provided herein.

Unless defined otherwise, all technical and scientific terms used herein have the same meaning as commonly understood to one of ordinary skill in the art to which this disclosure belongs. Although any methods, devices and materials similar or equivalent to those described herein can be used in the practice or testing of the disclosure, the preferred methods, devices and materials are now described.

As described further herein, the present disclosure relates to lyophilized compositions of a new class of fluorescent nanoparticles or chromophoric polymer dots that have unique properties. The present disclosure provides lyophilized chromophoric polymer dot compositions and related methods. This disclosure also provides methods of using such polymers, methods of synthesizing such polymers and kits containing such polymers.

As used herein, "polymer" is a molecule composed of at least two repeating structural units typically connected by covalent chemical bonds. The repeating structural unit may be one type of monomer, and the resulting polymer is a homopolymer. In some cases, the polymers can include two different types of monomers, or three different types of monomers, or more types of monomers. Examples of monomers for synthesizing conjugated polymers include, but not limit to, benzene, fluorene, benzothiadiazole; thiophen, BODIPY; porphyrin, peryene, squaraine, and their derivatives.

As used herein, "chromophoric polymer dots" are pi-conjugated species with luminescent properties. The chromophoric polymer dots comprise polymers with one or more repeating units, which can be combined in fixed, ordered, or random configurations and ratios. A repeating unit can be a monomer or a chemical motif that occurs throughout the polymer, such as an aromatic or heterocyclic unit. The polymers can be halogenated, for example, fluorinated, chlorinated, brominated, or iodinated. A polymer, a repeating unit, or a monomer can be halogenated at one or multiple sites. A halogenated polymer, for example, a fluorinated polymer, can provide greater levels of fluorescence than can a non-halogenated analogous polymer. Chromophoric polymer dot also refers to a structure including one or more conjugated polymers (e.g., semiconducting polymers) that have been collapsed into a stable sub-micron sized particle. Chromophoric polymer dots include fluorescent nanoparticles having at least one condensed conjugated polymer.

This disclosure also provides for variants of polymers. In some cases, a variant of a polymer is a conjugated polymer. Conjugated chromophoric polymer dots may also be referred to as chromophoric polymer dots. In some cases, halides (e.g., fluorine) are attached to or incorporated into the chromophoric polymer dot structure. The particle size of the chromophoric polymer dots may be comparable to that of a Qdot, for example, greater than 80% the size of a Qdot. The semiconducting polymers in chromophoric polymer dots may be present at a total volume that is at least 50% of the per-particle volume and preferably greater than 80%. The semiconducting polymers in chromophoric polymer dots may be present at a weight concentration that is at least 50% of the per-particle weight and preferably greater than 80%. Chromophoric polymer dots can possess a hydrophobic polymer interior. In some cases, a chromophoric polymer dot has a halide (e.g., fluorine) content of less than 50% by mass. In some cases, the weight concentration is greater than 40%, 50%, 60%, 70%, 80%, 90% or 99%. In some cases, the weight concentration is greater than about 40%, about 50%, about 60%, about 70%, about 80%, about 90% about or about 99%. In some cases, the weight concentration may be within the range of 40%-50%, 45%-55%, 50%-60%, 55%-65%, 60%-70%, 65%-75%, 70%-80%, 75%-85%, 80%-90%, 85%-95% or 90%-100%. In some cases, the weight concentration may be within the range of about 40%-50%, about 45%-55%, about 50%-60%, about 55%-65%, about 60%-70%, about 65%-75%, about 70%-80%, about 75%-85%, about 80%-90%, about 85%-95% or about 90%-100%.

As used herein, a chromophoric copolymer is represented by writing the identity of the major chromophoric species. For example, PFBT is a chromophoric polymer containing fluorene and benzothiazole units at a certain ratio. In some cases, a dash is used to indicate the percentage of the minor chromophoric species and then the identity of the minor chromophoric species. For example, PF-0.1 BT is a chromophoric copolymer containing 90% PF and 10% BT.

As used herein, the term "monosaccharide" refers to, e.g., molecules having the general formula: $C_x(H_2O)_y$, $x \geq 3$. Examples of monosaccharides can include, but are not limited to, glucose, fructose, galactose, xylose, ribose, and the like.

As used herein, the term "oligosaccharide" refers to, e.g., a short monosaccharide polymer that contains, e.g., between 2 to 30 monosaccharide units. An oligosaccharide can include, e.g., a "disaccharide" that refers to, e.g., molecules that are formed when two monosaccharides are joined together and, e.g., a molecule of water is removed. Examples of disaccharides can include, but are not limited to, sucrose, lactulose, lactose, maltose, trehalose, cellobiose, and the like. Other oligosaccharides can include, but are not limited to, trisaccharides (e.g., raffinose), tetrasaccharides (e.g., stachyose), and pentasaccharides (e.g., verbacose).

As used herein, the term "polysaccharide" refers to, e.g., a monosaccharide polymer beyond the length of the oligosaccharide, e.g., a polymer including more than 30 monosaccharide units.

As used herein, the term "sugar alcohol" refers to, e.g., a hydrogenated form of carbohydrate, whose carbonyl group (aldehyde or ketone, reducing sugar) has been reduced to a primary or secondary hydroxyl group. Sugar alcohols have the general formula $H(HCHO)_{n+1}H$. Example sugar alcohols can include, but are not limited to, alditols (e.g., xylitol, mannitol or sorbitol).

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together. As used herein, the term "heteroalkyl" refers to a straight or branched, saturated, aliphatic radical of carbon atoms, where at least one of the carbon atoms is replaced with a heteroatom, such as N, O or S. Additional heteroatoms can also be useful, including, but not limited to, B, Al, Si and P.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of $-(CH_2)_n-$, where n is 1, 2, 3, 4, 5 or 6. Alkylene groups include, but are not limited to, methylene, ethylene, propylene, isopropylene, butylene, isobutylene, sec-butylene, pentylene and hexylene.

The groups described herein can be substituted or unsubstituted. Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (CN), amino, sulfide, aldehyde, ester, ether, acid, hydroxyl or halide. Substituents can be a reactive group, such as but not limited to chloro, bromo, iodo, hydroxyl, or amino. Suitable substituents can be selected from: —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R'', —CN and —NO$_2$ in a number ranging from zero to (2m'+1), where m' is the total number of carbon atoms in such radical. R', R'' and R''' each independently refer to hydrogen, unsubstituted ($C_1$-$C_8$) alkyl and heteroalkyl, unsubstituted aryl, alkoxy or thioalkoxy groups, or aryl-($C_1$-$C_4$)alkyl groups. When R' and R'' are attached to the same nitrogen atom, they can be combined with the nitrogen atom to form a 5-, 6-, or 7-membered ring. For example, —NR'R'' is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "haloalkoxy" group.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4- pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups can be primary, secondary or tertiary. The alkyl amine can be further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the term "halogen" or "halide" refers to fluorine, chlorine, bromine and iodine. As used herein, the term "haloalkyl" refers to alkyl as defined above where some or all of the hydrogen atoms are substituted with halogen atoms. Halogen (halo) preferably represents chloro or fluoro, but may also be bromo or iodo. As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, and the like.

As used herein, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, C3-8 cycloalkyl includes cyclopropyl, cyclobutyl, cyclopentyl, cyclohexyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—.

As used herein, the term "heterocycloalkylene" refers to a heterocycloalkyl group, as defined above, linking at least two other groups. The two moieties linked to the heterocycloalkylene can be linked to the same atom or different atoms of the heterocycloalkylene.

As used herein, the term "aryl" refers to a monocyclic or fused bicyclic, tricyclic or greater, aromatic ring assembly containing 6 to 16 ring carbon atoms. For example, aryl may be phenyl, benzyl, azulenyl or naphthyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-C$_2$-C$_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g., methylenedioxy or ethylenedioxy. Oxy-C$_2$-C$_3$-alkylene is also a divalent substituent attached to two adjacent carbon atoms of phenyl, e.g., oxyethylene or oxypropylene. An example for oxy-C$_2$-C$_3$-alkylene-phenyl is 2,3-dihydrobenzofuran-5-yl.

Aryl groups can include, but are not limited to, naphthyl, phenyl or phenyl mono- or disubstituted by alkoxy, phenyl, halogen, alkyl or trifluoromethyl, phenyl or phenyl-mono- or disubstituted by alkoxy, halogen or trifluoromethyl, and in particular phenyl.

As used herein, the term "arylene" refers to an aryl group, as defined above, linking at least two other groups. The two moieties linked to the arylene are linked to different atoms of the arylene. Arylene groups include, but are not limited to, phenylene.

As used herein, the terms "alkoxy-aryl" or "aryloxy" refers to an aryl group, as defined above, where one of the moieties linked to the aryl is linked through an oxygen atom. Alkoxy-aryl groups include, but are not limited to, phenoxy (C$_6$H$_5$O—). The present disclosure also includes alkoxy-heteroaryl or heteroaryloxy groups.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g., alkyl, nitro or halogen. Suitable groups for the present disclosure can also include heteroarylene and heterarylene-oxy groups similar to the description above for arylene and arylene-oxy groups.

Similarly, aryl and heteroaryl groups described herein can be substituted or unsubstituted. Substituents for the aryl and heteroaryl groups are varied, such as alkyl, aryl, CN, amino, sulfide, aldehyde, ester, ether, acid, hydroxyl or halide. Substituents can be a reactive group, such as but not limited to chloro, bromo, iodo, hydroxyl, or amino. Substituents can be selected from: -halogen, —OR', —OC(O)R', —NR'R", —SR', —R', —CN, —NO₂, —CO₂R', —CONR'R", —C(O)R', —OC(O)NR'R", —NR"C(O)R', —NR"C(O)₂R', —NR'—C(O)NR"R''', —NH—C(NH₂)=NH, —NR'C(NH₂)=NH, —NH—C(NH₂)=NR', —S(O)R', —S(O)₂R', —S(O)₂NR'R", —N₃, —CH(Ph)₂, in a number ranging from zero to the total number of open valences on the aromatic ring system; and where R', R" and R''' are independently selected from hydrogen, (C₁-C₈) alkyl and heteroalkyl, unsubstituted aryl and heteroaryl, (unsubstituted aryl)-(C₁-C₄) alkyl, and (unsubstituted aryl)oxy-(C₁-C₄) alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some cases, the alkyl component can be absent. The aryl component is as defined above. Examples of alkyl-aryl groups include, but are not limited to, benzyl. The present disclosure also includes alkyl-heteroaryl groups.

As used herein, the term "alkenyl-aryl" refers to a radical having both an alkenyl component and an aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkenyl-aryl include ethenyl-phenyl, among others. The present disclosure also includes alkenyl-heteroaryl groups.

As used herein, the term "alkynyl-aryl" refers to a radical having both an alkynyl component and an aryl component, where the alkynyl component links the aryl component to the point of attachment. The alkynyl component is as defined above, except that the alkynyl component is at least divalent in order to link to the aryl component and to the point of attachment. The aryl component is as defined above. Examples of alkynyl-aryl include ethynyl-phenyl, among others. The present disclosure also includes alkynyl-heteroaryl groups.

Polymers for Polymer Dots

This disclosure provides for methods and compositions using polymers. A polymer is a molecule composed of at least 2 repeating structural units typically connected by covalent chemical bonds. The repeating structural unit may be one type of monomer, and the resulting polymer is a homopolymer. In some cases, the polymers can include two different types of monomers, or three different types of monomers, or more types of monomers. Examples of monomers for synthesizing conjugated polymers include, but not limit to, benzene, fluorene, benzothiadiazole; thiophen, BODIPY; porphyrin, peryene, squaraine, and their derivatives.

The chromophoric polymer dots can be formed using a variety of polymers. Non-limiting examples of semiconducting polymers include fluorene polymers (e.g., Poly(9,9-dihexylfluorenyl-2,7-diyl) (PDHF), Poly(9,9-dioctylfluorenyl-2,7-diyl) (PFO)), fluorene based copolymers (e.g., Poly[{9,9-dioctyl-2,7-divinylene-fluorenylene}-alt-co-{2-methoxy-5-(2-ethylhexyloxy)-1,4-phenylene}] (PFPV), Poly[(9,9-dioctylfluorenyl-2,7-diyl)-co-(1,4-benzo-{2,1,3}-thiadiazole)] (PFBT), Poly[(9,9-dioctylfluorenyl-2,7-diyl)-co-(4,7-Di-2-thienyl-2,1,3-benzothiadiazole)] (PFTBT), Poly[(9,9-dioctylfluorenyl-2,7-diyl)-9-co-(4,7-Di-2-thienyl-2,1,3-benzothiadiazole)] (PF-0.1TBT)), phenylene vinylene polymers (e.g., Poly[2-methoxy-5-(2-ethylhexyloxy)-1,4-phenylenevinylene] (MEH-PPV)), poly[2-methoxy-5-(2-ethylhexyloxy)-1,4-(1-cyanovinylene-1,4-phenylene)] (CN-PPV), BODIPY 570, BODIPY 590, BODIPY 690, and other polymers that are used to make narrow band chromophoric polymer dots (e.g., BODIPY-based chromophoric polymer dots) such as those described in PCT/US12/71767, which is herein incorporated by reference in its entirety). Other suitable polymers and chromophoric polymer dots are provided, e.g., in WO2011/057295, which is herein incorporated by reference in its entirety. As provided, e.g., in WO2011/057295, the polymers in the chromophoric polymer dots can be physically blended or chemically bonded (or chemically crosslinked). For example, the physically blended chromophoric polymer dots can include polymers that are blended in the chromophoric polymer dot and held together by non-covalent interactions. Chemically bonded chromophoric polymer dots can include polymers that are covalently attached to each other in the chromophoric polymer dot. The chemically bonded polymers can be covalently attached to each other prior to formation of the chromophoric polymer dots. In some cases, the polymers and chromophoric polymer dots can include those disclosed and claimed, e.g., in PCT/US11/56768. For example, the chromophoric polymer dots can include those that are directly functionalized and/or have low density functionalization.

A polymer of the disclosure can have a range of subunits, such as monomers or repeat units. The number of subunits in a polymer can be, for example, about 2 to about 100,000, about 2 to about 10,000, about 2 to about 1,000, about 2 to about 100, about 10 to about 100,000, about 10 to about 10,000, about 10 to about 1,000, about 100 to about 100,000, or about 100 to about 10,000. The number of subunits in a polymer can be, for example, 2 to 100,000, 2 to 10,000, 2 to 1,000, 2 to 100, 10 to 100,000, 10 to 10,000, 10 to 1,000, 100 to 100,000, or 100 to 10,000. The number of subunits in a polymer can be, for example, greater than 2, greater than 10, greater than 100, greater than 1,000, greater than 10,000; or greater than 100,000. The number of subunits in a polymer can be, for example, less than 2, less than 10, less than 100, less than 1,000, less than 10,000; or less than 100,000. The number of subunits in a polymer can be, for example, about 2, about 10, about 100, about 1,000, about 10,000; or about 100,000. The number of subunits in a polymer can be, for example, 2, 10, 100, 1,000, 10,000; or 100,000.

A polymer of the disclosure can have different kinds of subunits, for example, 2, 3, 4, 5, 6, 7, 8, 9, or 10 different kinds of subunits. An individual subunit can provide as percentage of the overall mass or a percentage of the number of units or monomers of the polymer, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. An individual subunit can provide as percentage of the overall mass or a percentage of the number of units or monomers of the polymer, for example, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or greater than 100%. An individual subunit can provide as percentage of the overall mass or a percentage of the number of units or monomers of the polymer, for example, less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, or less than 100%. An individual subunit can provide as percentage of the overall mass or a percentage of the number of units or monomers of the polymer, for example, 5%, 10%, 15%, 20%, 25%, 30%, 35%, 40%, 45%, 50%, 55%, 60%, 65%, 70%, 75%, 80%, 85%, 90%, 95%, or 100%.

Chromophoric Polymer Dots and Semiconducting Chromophoric Polymer Dots

This disclosure also provides for methods and compositions using polymers and variants thereof to form chromophoric polymer dots. Chromophoric polymer dots are a structure that includes one or more conjugated polymers (e.g., semiconducting polymers) that have been collapsed into a stable sub-micron sized particle. Chromophoric polymer dots include fluorescent nanoparticles having at least one condensed conjugated polymer.

The present disclosure provides chromophoric polymer dots that are semiconducting, non-semiconducting, or a combination thereof. Any polymer composition can be used according to the present disclosure so long as it is suitable for detecting proteins and peptides, such as for example, in the course of Western blot analysis, flow cytometry, histology or the like.

The present disclosure provides for chromophoric polymer dots having desirable surface chemistry and optical properties, making them particularly well suited for lyophilization according to the methods, compositions and kits described herein. The optical properties and degree of functionalization for a population of chromophoric polymer dots can be adjusted during production of the chromophoric polymer dots. In particular, the attributes of the chromophoric polymer dots can be adjusted as needed in order to tune a variety of photophysical properties (e.g., absorbance, emission brightness and/or the color of emission). In certain cases, the polymer dots provide unexpected brightness and/or photostability. Notably, in some cases, quenching of fluorescence is not increased due to particle formation. Furthermore, low, discrete numbers of functional groups on the surface of the polymer dots can reduce non-specific absorption of the chromophoric polymer dots to biologically relevant molecules and/or cells. It will be appreciated that polymer dots having high brightness and specific binding capabilities provide important cases to furthering areas of imaging and detection techniques for studying chemical and biological analytes and systems.

The chromophoric polymer dots used herein can be formed by any method known in the art for collapsing polymers, including without limitation, methods relying on precipitation, methods relying on the formation of emulsions (e.g., mini or micro emulsion), and methods relying on condensation.

In some cases, chromophoric polymer dots can be formed by precipitation. This technique involves the rapid addition (e.g., facilitated by sonication or vigorous stirring) of a dilute chromophoric polymer solution (e.g., chromophoric polymer dissolved in an organic solvent) into an excess volume of non-solvent (but miscible with the organic solvent), such as water or another physiologically relevant aqueous solution. For example, in some of the procedures described herein, the chromophoric polymer can be first dissolved into an organic solvent where the solubility is good (good solvent), such as THF (tetrahydrofuran), after which the dissolved polymer in THF is added to an excess volume of water or buffer solution, which is a poor solvent for the hydrophobic chromophoric polymers but which is miscible with the good solvent (THF). The resulting mixture is sonicated or vigorously stirred to assist the formation of chromophoric polymer dots, then the organic solvent is removed to leave behind well dispersed chromophoric nanoparticles. In using this procedure, the chromophoric polymer should be sufficiently hydrophobic to dissolve into the organic solvent (e.g., THF). The introduction of a high density of hydrophilic functional groups on side chains for coupling to biomolecules or high density of hydrophilic side chains will make the resulting polymer, in a fashion similar or identical to the behavior of polyelectrolytes, insoluble or poorly soluble in an organic solvent (e.g., THF).

In some cases, methods, compositions and kits are provided for the use of chromophoric polymer dots formed by other methods, including but not limited to various methods based on emulsions (e.g., mini or micro emulsion) or precipitations or condensations. Other polymers having hydrophobic functional groups can also be employed, in which the hydrophobic functional groups do not affect the collapse and stability of the chromophoric polymer dot. The hydrophobic functional groups on the surface of the nanoparticles can then be converted to hydrophilic functional groups (e.g., by post-functionalization) for bioconjugation or directly link the hydrophobic functional groups to biomolecules. This latter approach can work particularly well using functional groups that are both hydrophobic and clickable (i.e., chemical reactions that fall within the framework of click chemistry), including but not limited to alkyne, strained alkyne, azide, diene, alkene, cyclooctyne, and phosphine groups.

In some cases, methods, compositions and kits are provided for the use of functionalized chromophoric polymer dots that have been modified to form a single-molecule polymer dot that can be monovalent, bivalent, or multivalent. The modification is to remove some polymer molecules from the dot, but leave only one molecule that can have just one functional group, two or more functional groups. In one case, an engineered surface can be used to facilitate the modification. The engineered surface can have certain functional groups such as aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, and combinations thereof. In general, any other functional groups that are suitable for bioconjugation can be used. Such functional groups could be found by one of ordinary skill in the art, for example in Bioconjugate Techniques (Academic Press, New York, 1996 or later versions). The surface can be a flat surface such as a coverslip or a curved surface from any particles. The surfaces can be silica, metal, semiconducting, silicon, and different polymer surfaces. The functionalized multi-molecule chromophoric polymer dot described above is attached to the surface by only one chromophoric polymer molecule via any stable physical or chemical association. All the free molecules (except the one associated with the surface) in the chromophoric polymer dot can be removed, such as by washing the surface with an organic solvent, so that only the molecule associated with the surface is retained. Then the single-molecule chromophoric dot can be released from the surface by any physical or chemical methods. The resulting single-molecule dot could be monovalent, bivalent, or multivalent, depending on the number of functional groups in the original polymer molecule.

Polymer Dots

A number of semiconducting polymers are suitable for use with lyophilization according to the present disclosure. Semiconducting polymers have been developed with emission wavelengths ranging from UV to infrared, including the entire visible spectrum. In various cases, methods, compositions and kits are provided for the use of semiconducting polymers, including but not limited to: polyfluorene polymers including but not limited to poly(9,9-dihexylfluorenyl-2,7-diyl) (PDHF) and poly(9,9-dioctylfluorenyl-2,7-diyl) (PFO); fluorene-based copolymers, including but not limited to, poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), and poly[(9,9-dioctylfluorenyl-2,7-diyl)-co-(4,7-Di-2-thienyl-2,1,3-benzothiadiazole)] (PF-0.1TBT); phenylene vinylene polymers, including but not limited to, poly[2-methoxy-5-(2-ethylhexyloxy)-1,4-phenylenevinylene] (MEH-PPV) and poly[2-methoxy-5-(2-ethylhexyloxy)-1,4-(1-cyanovinylene-1,4-phenylene)] (CN-PPV); phenylene ethynylene polymers, including but not limited to, poly(2,5-di(3',7'-dimethyloctyl)phenylene-1,4-ethynylene (PPE). In some cases, chromophoric polymer dots can be used that contain a polystyrene-based, comb-like polymer. Non-limiting examples of polystyrene based comb-like polymers include, polystyrene graft acrylic acid, polystyrene graft ethylene oxide, polystyrene graft butyl alcohol, and the like.

In some cases, chromophoric polymer dots can be used that contain poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide, and the like.

In some cases, chromophoric polymer dots can be used that contain a comb-like polymer comprising carboxyl, amine, thiol, ester, succinimidyl ester, azide, alkyne, cyclooctyne, or phosphine groups.

In some cases, chromophoric polymer dots can be used that contain a polymer functionalized on the terminal monomeric unit, for example with a carboxyl, amine, thiol, ester, succinimidyl ester, azide, alkyne, cyclooctyne, phosphine, or similar functional group. Examples of polymers that can be used include, without limitation, poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

In some cases, chromophoric polymer dots can be used that contain a copolymer having one or more functionalized monomeric units, for example an amphiphilic polymer, including but not limited to: poly((meth)acrylic acid)-based copolymers such as: poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); polydiene-based copolymers such as: poly(butadiene(1,2 addition)-b-ethylene oxide), poly(butadiene(1,2 addition)-b-methylacrylic acid, poly(butadiene(1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly(isoprene-b-ethylene oxide), and poly (isoprene-b-N-methyl 2-vinyl pyridinium iodide); poly (ethylene oxide)-based copolymers such as: poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); polyisobutylene-based copolymers such as poly(isobutylene-b-acrylic acid), poly(isobutylene-b-ethylene oxide), poly(isobutylene-b-methacrylic acid); polystyrene based copolymers such as poly(styrene-b-acrylamide), poly(styrene-b-acrylic acid), poly(styrene-b-cesium acrylate), poly (styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); polysiloxane-based copolymers such as poly(dimethylsiloxane-b-acrylic acid), poly(dimethylsiloxane-b-ethylene oxide), poly(dimethylsiloxane-b-methacrylic acid); poly(ferrocenyldimethylsilane) based copolymers such as poly(ferrocenyldimethylsilane-b-ethylene oxide); poly(2-vinyl naphthalene)-based copolymers such as poly(2-vinyl naphthalene-b-acrylic acid), poly (vinyl pyridine and N-methyl vinyl pyridinium iodide)-based copolymers such as poly(2-vinyl pyridine-b-ethylene oxide), poly(2-vinyl pyridine-b-methyl acrylic acid), poly (N-methyl 2-vinyl pyridinium iodide-b-ethylene oxide), poly(N-methyl 4-vinyl pyridinium iodide-b-methyl methacrylate), poly(4-vinyl pyridine-b-ethylene oxide) PEO end functional OH; and poly(vinyl pyrrolidone)-based copolymers such as poly(vinyl pyrrolidone-b-D/L-lactide); and the like.

In some cases of the present disclosure, chromophoric polymer dots used for detection can comprise the polymer, CN-PPV, which is a bright, compact, and orange-emitting semiconducting polymer dot also known as, poly[2-methoxy-5-(2-ethylhexyloxy)-1,4-(1-cyanovinylene-1,4-phenylene)]. CN-PPV has superior fluorescence properties, such as a large absorption cross-section, high quantum yield, and a fast emission rate.

In some cases, the chromophoric polymer dot used for detecting proteins and peptides can comprises a polymer that consists essentially of CN-PPV. In some cases, the nanoparticle includes CN-PPV and at least one other material. For example, the CN-PPV can be mixed with a copolymer or other material that provides an additional functionality.

In some cases, the polymer dots used for the detection of proteins and peptides can include a semiconducting copolymer having at least two different chromophoric units. For example, a conjugated copolymer can contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophene unit, carbazole fluorene unit, boron-dipyrromethene unit, and derivatives thereof. The different chromophoric units can be segregated, as in a block copolymer, or intermingled. As used herein, a chromophoric copolymer is represented by writing the identity of the major chromophoric species. For example, PFBT is a chromophoric polymer containing fluorene and benzothiazole units at a certain ratio. In some cases, a dash is used to indicate the percentage of the minor chromophoric species and then the identity of the minor chromophoric species. For example, PF-0.1 BT is a chromophoric copolymer containing 90% PF and 10% BT.

In certain cases, the polymer dots can include a blend of semiconducting polymers. The blends can include any combination of homopolymers, copolymers, and oligomers. Polymer blends used to form polymer dots may be selected in order to tune the properties of the resulting polymer dots, for example, to achieve a desired excitation or emission spectra for the polymer dot.

In some cases, chromophoric polymer dots are pi-conjugated species with luminescent properties. The chromophoric polymer dots may comprise polymers with one or more repeating units, which can be combined in fixed, ordered, or random configurations and ratios. In some cases, a repeating unit can be a monomer or a chemical motif that occurs throughout the polymer, such as an aromatic or heterocyclic unit.

The polymers can be halogenated, for example, fluorinated, chlorinated, brominated, or iodinated. In some cases, a polymer, a repeating unit, or a monomer can be halogenated at one or multiple sites. A halogenated polymer, for example, a fluorinated polymer, can provide greater levels of fluorescence than can a non-halogenated analogous polymer.

The majority of organic polymers used for chromophoric polymer dots are insulators. When organic polymers have π-conjugated structures, electrons can move along the polymer backbone through overlaps in π-electron clouds by hopping, tunneling, and related mechanisms. In some cases, these π-conjugated polymers include wide-bandgap semiconductors, for example, semiconducting polymers.

In some cases, the chromophoric polymer dot used comprises polymers bearing units of small organic dye molecules, metal complexes, photochotochromic dye, and any combinations thereof, for example, optically inactive polymers such as polystyrene covalently linked or grafted with small organic dye, metal complexes, photochromic dyes and any combination thereof. These dyes or metal complexes may have protein sensing capability.

Chromophoric polymer dots comprising semiconducting polymers covalently linked with small organic dye molecules, metal complexes, photochromic dyes, and any combinations thereof as emissive units. Such emissive units can tune the emission color, increase the quantum yield, and improve the photostability of the chromophoric polymer dot.

Semiconducting polymers can exhibit a direct band gap, which leads to an efficient (allowed) absorption or emission at the band edge. Depending on the polymer species, a semiconducting polymer can exhibit strong fluorescence, which can be described in terms of semiconductor band theory. Upon photoexcitation, an electron is excited from the highest occupied energy band (the π band) to the lowest unoccupied energy band (the π* band), thus forming a bound state (excitors) of the excited electron and hole in the π band. The recombination of the excited electron with the hole results in a fluorescent photon. The wavelength of the absorbed light is determined by the π-π* energy gap and can be tuned by altering the molecular structure of the polymer.

Semiconducting polymers can have emission colors that span the full range of the visible spectrum. For example, fluorescent semiconducting polymers may include polyfluorene (such as PDHF and PFO), poly(phenylene ethynylene) (such as PPE), poly(phenylene vinylene) (such as MEH-PPV and CN-PPV), fluorene-based copolymers (such as PFPV, PFBT, and PF-DBT5), and BODIPY-based copolymers, and related derivatives.

In many cases, photogenerated electron-hole pairs can dissociate to form free carriers which migrate through the system. The free carriers can either combine to form triplets or deactivate by other nonradiative processes (unwanted processes for fluorescence). They can also be collected to generate electric current (desirable processes for photovoltaics).

In some cases, the chromophoric polymer dots can include a semiconducting copolymer having at least two different chromophoric units. For example, a conjugated copolymer may contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophene unit, carbazole fluorene unit, boron-dipyrromethene unit, and derivatives thereof. The different chromophoric units may be segregated, as in a block copolymer, or intermingled.

In certain cases, the chromophoric polymer dots can include a blend of semiconducting polymers. The blends may include any combination of homopolymers, copolymers, and oligomers. Polymer blends used to form chromophoric polymer dots may be selected in order to tune the properties of the resulting chromophoric polymer dots, for example, to achieve a desired excitation or emission spectra for the chromophoric polymer dot.

Sizes of the nanoparticles provided herein are defined in terms of a "critical dimension," which refers to the smallest dimension of the nanoparticle. Many nanoparticles are roughly spherical in shape, which results in the critical dimension being the radius or diameter of the spherical particle. While typical nanoparticles, such as nanospheres and nanocubes, are completely nanoscopic in size, not every dimension of a nanoparticle needs to be at the nanoscale. For example, a nano-cylinder may have a diameter on the nano-scale but a length on the micro-scale.

In some cases, the critical dimension of the chromophoric polymer dot used is 200 nm or less. In some cases, the critical dimension of the chromophoric polymer dot used is 180 nm or less. In some cases, the critical dimension is 170 nm or less. In some cases, the critical dimension is 160 nm or less. In some cases, the critical dimension is 150 nm or less. In some cases, the critical dimension is 155 nm or less. In some cases, the critical dimension is 150 nm or less. In some cases, the critical dimension is 145 nm or less. In some cases, the critical dimension is 140 nm or less. In some cases, the critical dimension is 135 nm or less. In some cases, the critical dimension is 130 nm or less. In some cases, the critical dimension is 125 nm or less. In some cases, the critical dimension is 120 nm or less. In some cases, the critical dimension is 115 nm or less. In some cases, the critical dimension is 110 nm or less. In some cases, the critical dimension is 105 nm or less. In some cases, the critical dimension is 100 nm or less. In some cases, the critical dimension is 95 nm or less. In some cases, the critical dimension is 90 nm or less. In some cases, the critical dimension is 85 nm or less. In some cases, the critical dimension is 80 nm or less. In some cases, the critical dimension is 75 nm or less. In some cases, the critical dimension is 70 nm or less. In some cases, the critical dimension is 65 nm or less. In some cases, the critical dimension is 60 nm or less. In some cases, the critical dimension is 55 nm or less. In some cases, the critical dimension is 50 nm or less. In some cases, the critical dimension is 45 nm or less. In some cases, the critical dimension is 40 nm or less. In some cases, the critical dimension is 35 nm or less. In some cases, the critical dimension is 30 nm or less. In some cases, the critical dimension is 25 nm or less. In some cases, the critical dimension is 20 nm or less. In some cases, the critical dimension is 15 nm or less. In some cases, the critical dimension is 10 nm or less. In some cases, the critical dimension is 5 nm or less.

In some cases, the critical dimension of the chromophoric polymer dot used is 200 nm or greater. In some cases, the critical dimension of the chromophoric polymer dot used is 180 or greater. In some cases, the critical dimension is 170 nm or greater. In some cases, the critical dimension is 160 nm or greater. In some cases, the critical dimension is 150 nm or greater. In some cases, the critical dimension is 155 nm or greater. In some cases, the critical dimension is 150 nm or greater. In some cases, the critical dimension is 145 nm or greater. In some cases, the critical dimension is 140 nm or greater. In some cases, the critical dimension is 135 nm or greater. In some cases, the critical dimension is 130 nm or greater. In some cases, the critical dimension is 125 nm or greater. In some cases, the critical dimension is 120 nm or greater. In some cases, the critical dimension is 115 nm or greater. In some cases, the critical dimension is 110 nm or greater. In some cases, the critical dimension is 105 nm or greater. In some cases, the critical dimension is 100 nm or greater. In some cases, the critical dimension is 95 nm or greater. In some cases, the critical dimension is 90 nm or greater. In some cases, the critical dimension is 85 nm or greater. In some cases, the critical dimension is 80 nm or greater. In some cases, the critical dimension is 75 nm or greater. In some cases, the critical dimension is 70 nm or greater. In some cases, the critical dimension is 65 nm or greater. In some cases, the critical dimension is 60 nm or greater. In some cases, the critical dimension is 55 nm or greater. In some cases, the critical dimension is 50 nm or greater. In some cases, the critical dimension is 45 nm or greater. In some cases, the critical dimension is 40 nm or greater. In some cases, the critical dimension is 35 nm or greater. In some cases, the critical dimension is 30 nm or greater. In some cases, the critical dimension is 25 nm or greater. In some cases, the critical dimension is 20 nm or greater. In some cases, the critical dimension is 15 nm or greater. In some cases, the critical dimension is 10 nm or greater. In some cases, the critical dimension is 5 nm or greater.

In some cases, the critical dimension of the chromophoric polymer dot used is about 200 nm. In some cases, the critical dimension of the chromophoric polymer dot used is about 180 nm. In some cases, the critical dimension is about 170 nm. In some cases, the critical dimension is about 160 nm. In some cases, the critical dimension is about 155 nm. In some cases, the critical dimension is about 150 nm. In some cases, the critical dimension is about 145 nm. In some cases, the critical dimension is about 140 nm. In some cases, the critical dimension is about 135 nm. In some cases, the critical dimension is about 130 nm. In some cases, the critical dimension is about 125 nm. In some cases, the critical dimension is about 120 nm. In some cases, the critical dimension is about 115 nm. In some cases, the critical dimension is about 110 nm. In some cases, the critical dimension is about 105 nm. In some cases, the critical dimension is about 100 nm. In some cases, the critical dimension is about 95 nm. In some cases, the critical dimension is about 90 nm. In some cases, the critical dimension is about 85. In some cases, the critical dimension is about 80 nm. In some cases, the critical dimension is about 75 nm. In some cases, the critical dimension is about 70 nm. In some cases, the critical dimension is about 65 nm. In some cases, the critical dimension is about 60 nm. In some cases, the critical dimension is about 55 nm. In some cases, the critical dimension is about 50 nm. In some cases, the critical dimension is about 45 nm. In some cases, the critical dimension is about 40 nm. In some cases, the critical dimension is about 35 nm. In some cases, the critical dimension is about 30 nm. In some cases, the critical dimension is about 25 nm. In some cases, the critical dimension is about 20 nm. In some cases, the critical dimension is about 15 nm. In some cases, the critical dimension is about 10 nm. In some cases, the critical dimension is about 5 nm.

In some cases, the chromophoric polymer dot used has a critical dimension greater than 1 nm and less than 1000 nm. In some cases, the chromophoric polymer dot used has a critical dimension greater than 10 nm and less than 1000 nm. In some cases, the chromophoric polymer dot used has a critical dimension greater than 20 nm and less than 1000 nm. In some cases, the chromophoric polymer dot used has a critical dimension greater than 30 nm and less than 1000 nm. In some cases, the chromophoric polymer dot used has a critical dimension greater than 40 nm and less than 1000 nm. In some cases, the chromophoric polymer dot used has a critical dimension greater than 50 nm and less than 1000 nm. In some cases, the chromophoric polymer dot used has a critical dimension greater than 1 nm and less than 100 nm. In some cases, the chromophoric polymer dot used has a critical dimension greater than 1 nm and less than 90 nm. In some cases, the chromophoric polymer dot used has a critical dimension greater than 1 nm and less than 80 nm. In some cases, the chromophoric polymer dot used has a critical dimension greater than 1 nm and less than 70 nm. In some cases, the chromophoric polymer dot used has a critical dimension greater than 1 nm and less than 60 nm. In some cases, the chromophoric polymer dot used has a critical dimension greater than 1 nm and less than 50 nm. In some cases, the chromophoric polymer dot used has a critical dimension greater than 1 nm and less than 40 nm. In some cases, the chromophoric polymer dot used has a critical dimension greater than 1 nm and less than 30 nm. In some cases, the chromophoric polymer dot used has a critical dimension greater than 1 nm and less than 20 nm. In some cases, the chromophoric polymer dot used has a critical dimension greater than 1 nm and less than 10 nm.

In some cases, the chromophoric polymer dot used has a critical dimension of about greater than about 1 nm and less than about 1000 nm. In some cases, the chromophoric polymer dot used has a critical dimension of about greater than about 10 nm and less than about 1000 nm. In some cases, the chromophoric polymer dot used has a critical dimension of about greater than about 20 nm and less than about 1000 nm. In some cases, the chromophoric polymer dot used has a critical dimension of about greater than about 30 nm and less than about 1000 nm. In some cases, the chromophoric polymer dot used has a critical dimension of about greater than about 40 nm and less than about 1000 nm. In some cases, the chromophoric polymer dot used has a critical dimension of about greater than about 50 nm and less than about 1000 nm. In some cases, the chromophoric polymer dot used has a critical dimension of about greater than about 1 nm and less than about 100 nm. In some cases, the chromophoric polymer dot used has a critical dimension of about greater than about 1 nm and less than about 90 nm. In some cases, the chromophoric polymer dot used has a critical dimension of about greater than about 1 nm and less than about 80 nm. In some cases, the chromophoric polymer dot used has a critical dimension of about greater than about 1 nm and less than about 70 nm. In some cases, the chromophoric polymer dot used has a critical dimension of about greater than about 1 nm and less than about 60 nm. In some cases, the chromophoric polymer dot used has a critical dimension of about greater than about 1 nm and less than about 50 nm. In some cases, the chromophoric polymer dot used has a critical dimension of about greater than about 1 nm and less than about 40 nm. In some cases, the chromophoric polymer dot used has a critical dimension of about greater than about 1 nm and less than about 30 nm. In some cases, the chromophoric polymer dot used has a critical dimension of about greater than about 1 nm and less than about 20 nm. In some cases, the chromophoric polymer dot used has a critical dimension of about greater than about 1 nm and less than about 10 nm.

The possible shape of the nanoparticle is essentially unlimited. However, in certain cases, the shape is selected from a sphere, a cylinder, an ellipsoid, a polyhedron, a prism, a rod, and a wire. The shape of the nanoparticle can contribute to the detection properties, as will be appreciated by those of skill in the art (e.g., nano-rods may have different optical properties than nano-spheres).

The nano-scale size of the nanoparticle is essential in order to bypass issues presented by large particle sizes. For example, when attaching nanoparticles to a target molecule (e.g., a protein) for photoluminescence imaging, relatively large particles have more surface area available for non-specific binding to molecules other than the target, or adsorption to a surface.

The provided nanoparticles are optimized for use as photo-luminescent reporters that can be attached to a target molecule as part of an analysis method, system or kit. The nanoparticles should be easily detectable using photoluminescence and should have specificity for their target molecules.

The optical properties, such as absorption wavelength, for a given chromophoric polymer dot can be tuned by modifying its composition and geometry. Semiconducting polymers have been developed with absorption wavelengths ranging from UV to infrared, including the entire visible spectrum. In some cases, chromophoric polymer dots having a peak absorption wavelength between 200 nm and 300 nm, 250 nm and 350 nm, 300 nm and 400 nm, 350 nm and 450 nm, between 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, or 900 nm and 1000 nm are used.

In other cases, chromophoric polymer dots having a peak absorption wavelength between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm are used.

Semiconducting polymers have been developed with emission wavelengths ranging from UV to infrared, including the entire visible spectrum. In some cases, chromophoric polymer dots having a peak emission wavelength between 200 nm and 300 nm, 250 nm and 350 nm, 300 nm and 400 nm, 350 nm and 450 nm, 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, 900 nm and 1000 nm, 950 nm and 1050 nm, 1000 nm and 1100 nm, 1150 nm and 1250 nm, or 1200 nm and 1300 nm are used.

In other cases, chromophoric polymer dots having a peak emission wavelength between about 200 nm and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, about 900 nm and about 1000 nm, about 950 nm and about 1050 nm, about 1000 nm and about 1100 nm, about 1150 nm and about 1250 nm, or about 1200 nm and about 1300 nm are used.

In some cases, the methods, compositions and kits provided will make use of chromophoric polymer dots with narrow-band emissions. Narrow-band emissions are advantageous for certain applications, including but not limited to multiplexing applications. The emission wavelength of the polymer dots can vary from ultraviolet to near infrared region. The full width at half maximum (FWHM) of the emission band is less than 70 nm. In some cases, the FWHM is less than 65 nm. In some cases, the FWHM is less than 60 nm. In some cases, the FWHM is less than 55 nm. In some cases, the FWHM is less than 50 nm. In some cases, the FWHM is less than 45 nm. In some cases, the FWHM is less than 40 nm. In some cases, the FWHM is less than 35 nm. In some cases, the FWHM is less than 30 nm. In some cases, the FWHM is less than 25 nm. In some cases, the FWHM is less than 20 nm. In some cases, the FWHM is less than 10 nm. In some cases, the FWHM of the polymer dots described herein can range between 5 nm to 70 nm, from 10 nm to 60 nm, from 20 nm to 50 nm, or from 30 nm to 45 nm.

In other cases, the methods, compositions and kits provided will make use of chromophoric polymer dots with narrow-band emissions. Narrow-band emissions are advantageous for certain applications, including but not limited to multiplexing applications. The emission wavelength of the polymer dots can vary from ultraviolet to near infrared region. The full width at half maximum (FWHM) of the emission band is less than 70 nm. In some cases, the FWHM is less than about 65 nm. In some cases, the FWHM is less than about 60 nm. In some cases, the FWHM is less than about 55 nm. In some cases, the FWHM is less than about 50 nm. In some cases, the FWHM is less than about 45 nm. In some cases, the FWHM is less than about 40 nm. In some cases, the FWHM is less than about 35 nm. In some cases, the FWHM is less than about 30 nm. In some cases, the FWHM is less than about 25 nm. In some cases, the FWHM is less than about 20 nm. In some cases, the FWHM is less than about 10 nm. In some cases, the FWHM of the polymer dots described herein can range between about 5 nm to about 70 nm, from about 10 nm to about 60 nm, from about 20 nm to about 50 nm, or from about 30 nm to about 45 nm.

In some cases, the narrow-band emissive polymers for making chromophoric polymer dots include boron-dipyrromethene (4,4-difluoro-4-bora-3a,4a-diaza-s-indacene, BODIPY) and or their derivatives, and/or other boron-containing monomers and their derivatives, as narrow-band monomers. BODIPY and other boron containing monomers and their derivatives include but are not limited to their alkyl derivatives, aryl derivatives, alkyne derivatives, aromatic derivatives, alkoxide derivatives, aza derivatives, BODIPY extended and other BODIPY derivatives. The narrow-band emissive polymers can also include any other monomers. The BODIPY-based-monomers can be energy acceptors and other monomers can be energy donors so that the final chromophoric polymer dots can exhibit narrow-band emissions. The narrowband emissive chromophoric polymers in good solvents may exhibit broad emissions or narrow emissions. A comprehensive description of chromophoric polymer dots with narrow-band emissions, including BODIPY and other boron containing monomers and their derivatives, is described in WO2013/101902, which is herein incorporated by reference in its entirety.

As will be appreciated by one of ordinary skill in the art, the various chemical terms defined herein can be used for describing chemical structures of the polymers and monomers of the present disclosure. For example, a variety of the monomer derivatives (e.g., BODIPY derivatives) can include a variety of the chemical substituents and groups described herein. For example, in some cases, derivatives of the various monomers can be substituted with hydrogen, deuterium, alkyl, aralkyl, aryl, alkoxy-aryl, N-dialkyl-4-phenyl, N-diphenyl-4-phenyl, N-dialkoxyphenyl-4-phenyl, amino, sulfide, aldehyde, ester, ether, acid, and/or hydroxyl.

The present disclosure can include polymer dots, e.g., narrow-band emissive chromophoric polymer dots. As described further herein, the present disclosure includes a wide variety of polymer dots that exhibit narrow band emission properties (e.g., a FWHM less than 70 nm). As described further herein, the variety of polymer dots of the present disclosure can include polymers that have a narrow band emissive unit (e.g., a narrow band monomer and/or a narrow band unit). For example, the present disclosure can include a homopolymer or heteropolymer including a narrow band monomer, such as BODIPY and/or BODIPY derivative monomer, a squaraine and/or squaraine derivative, a metal complex and/or metal complex derivative monomer, a porphyrin and/or porphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. A narrow band unit can be, e.g., a narrow band monomer or a fluorescent nanoparticle embedded in or attached to the polymer dot. The fluorescent nanoparticle can be, e.g., a quantum dot. A narrow band unit can also include a polymer or fluorescent dye molecule that gives a narrow emission in a polymer dot of the present disclosure.

A variety of other BODIPY derivatives can be used for the present disclosure. BODIPY and BODIPY derivatives can be polymerized to form polymers (e.g., homopolymers or heteropolymers) and/or can be attached (e.g., covalently attached) to a polymer backbone, sidechain and/or terminus. In some cases, the chromophoric polymer dots of the present disclosure can include a polymer that includes a narrow-band monomer having the structure of Formula (I):

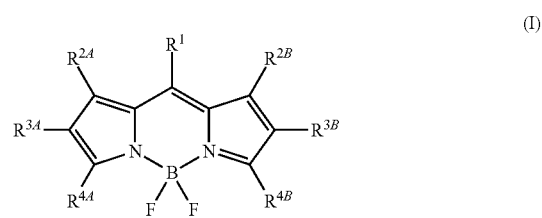

(I)

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —$(OCH_2CH_2)nOH$, n=1-50), phenyl, alkyl-(alkoxy-, aryl-, fluoroalkyl-, fluoroaryl-) substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$ or a combination thereof.

In some cases, the chromophoric polymer dots of the present disclosure can include a polymer that includes a narrow-band monomer having the structure of Formula (II):

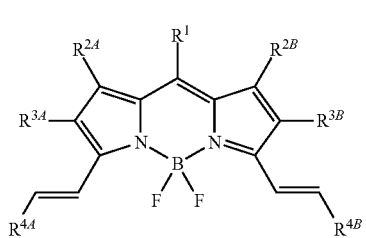

(II)

wherein each of $R^1$, $R^{2A}$, $R^{2B}$, $R^{3A}$, $R^{3B}$, $R^{4A}$ and a $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)nOH, n=1-50), phenyl, alkyl-(alkoxy-, aryl-, fluoroalkyl-, fluoroaryl-) substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$ or a combination thereof. The monomer can, for example, integrate with the backbone of the polymer by attachment to the $R^{3A}$ and $R^{3B}$ groups.

In some cases, the chromophoric polymer dots of the present disclosure can include a polymer that includes a narrow-band monomer having the structure of Formula (III):

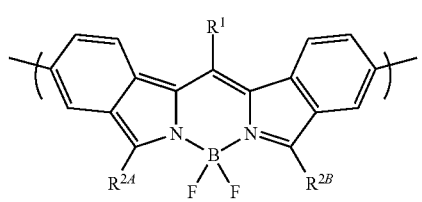

(III)

wherein each of $R^1$, $R^{2A}$ and $R^{2B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)nOH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkylsubstituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment, e.g., to $R^1$, $R^{2A}$, $R^{2B}$, or a combination thereof. The parentheses indicate points of attachment of the monomer to the backbone of the polymer.

In some cases, the chromophoric polymer dots of the present disclosure can include a polymer that includes a narrow-band monomer having the structure of Formula (IV):

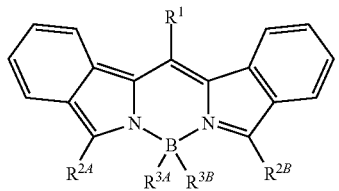

(IV)

wherein each of $R^1$, $R^{2A}$, $R^{2B}$, $R^{3A}$ and a $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)nOH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$ or a combination thereof.

In some cases, the chromophoric polymer dots of the present disclosure can include a polymer that includes a narrow-band monomer having the structure of Formula (V):

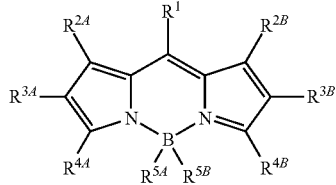

(V)

wherein each of $R^1$, $R^{2A}$, $R^{2B}$, $R^{3A}$, $R^{3B}$, $R^{4A}$, $R^{4B}$, $R^{5A}$ and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)nOH, n=1-50), phenyl, alkyl-(alkoxy-, aryl-, fluoroalkyl-, fluoroaryl-) substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, $R^{5A}$, $R^{5B}$, or a combination thereof. In certain cases, the narrow-band monomers can be integrated into the backbone by attachment to the $R^5A$ and $R^5B$ groups.

In some cases, the chromophoric polymer dots of the present disclosure can include a polymer that includes a narrow-band monomer having the structure of Formula (VI):

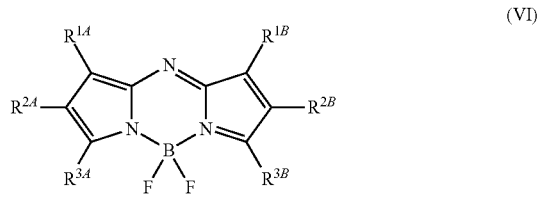

(VI)

wherein each of $R^1$, $R^{2A}$, $R^{2B}$, $R^{3A}$ and $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)nOH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzo-oxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$ or a combination thereof.

In some cases, the chromophoric polymer dots of the present disclosure can include a polymer that includes a narrow-band monomer having the structure of Formula (VII):

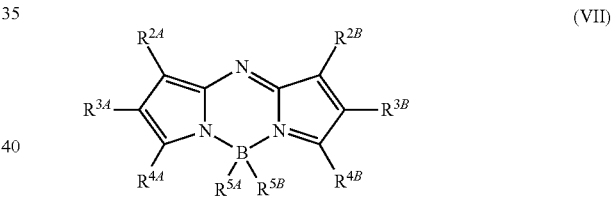

(VII)

wherein each of $R^{2A}$, $R^{2B}$, $R^{3A}$, $R^{3B}$, $R^{4A}$, $R^{4B}$, $R^{5A}$ and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)nOH, n=1-50), phenyl, alkyl-(alkoxy-, aryl-, fluoroalkyl-, fluoroaryl-) substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3 ',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl The narrow-band monomer can be integrated into a backbone of the polymer (e.g., polymerized in the polymer) and/or covalently attached to the backbone, a terminus, or a sidechain of the polymer) through at least one attachment $R^{2A}$, $R^{2B}$, $R^{3A}$, $R^{3B}$, $R^{4A}$, $R^{4B}$, $R^{5A}$, $R^{5B}$ or a combination thereof.

In some cases, the chromophoric polymer dots of the present disclosure can include a polymer that includes a narrow-band monomer having the structure of formula (VIII):

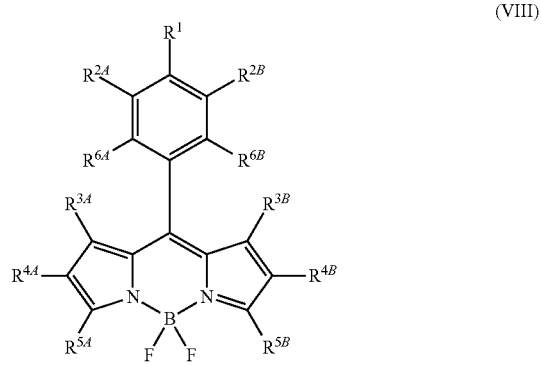

(VIII)

wherein each of $R^1$, $R^{2A}$, $R^{2B}$, $R^{3A}$, $R^{3B}$, $R^{4A}$, $R^{4B}$, $R^{5A}$, $R^{5B}$, $R^{6A}$ and $R^{6B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)nOH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-) substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl and wherein each of $R^5A$, $R^5B$, $R^6A$ and $R^6B$ are independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)nOH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-) substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer) through at least one attachment to $R^1$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$ or a combination thereof.

In some cases, the chromophoric polymer dots of the present disclosure can include a polymer that includes a narrow-band monomer having the structure of Formula (IX):

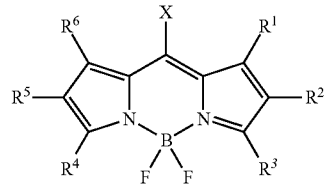

(IX)

wherein X has the structure of any one of Formulae (X), (XI), (XII), or (XIII) or their derivatives:

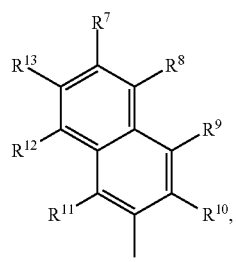

(X)

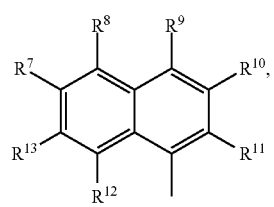

(XI)

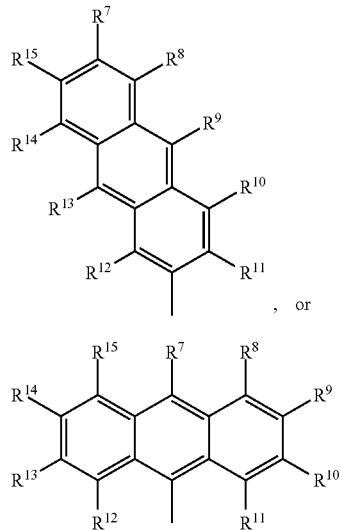

(XII)

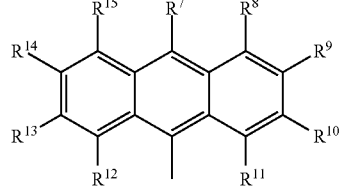

, or (XIII)

and wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in Formulae (X), (XI), (XII), and (XIII) is independently selected from the group consisting of hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-) substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary cases, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. When X represents naphthalene and its derivatives, the narrow-band monomer can be integrated into a backbone (e.g., polymerized in the polymer) and/or covalently attached to the backbone, a terminus, or a sidechain of the polymer) of the polymer through at least one attachment to $R^7$, $R^8$, $R^9$, $R^{10}$, $R^{11}$, $R^{12}$ or a combination thereof. When X represents anthracene and its derivatives, the narrow-band monomer can be integrated into a backbone of the polymer and/or covalently attached to the backbone, a terminus, or a sidechain of the polymer through at least one attachment to $R^7$, $R^8$, $R^9$, $R^{10}$, $R^{11}$, $R^{12}$, $R^{13}$, $R^{14}$, $R^{15}$ or a combination thereof.

A wide variety of polymer dots can be used, such as the examples described herein as well as others that are disclosed, e.g., in WO2011/057295 and WO2013/101902, each of which is incorporated by reference herein it its entirety and specifically with regard to the particular chromophoric polymer dot compositions and the respective methods of making them as described therein. As provided, e.g., in WO2011/057295, the polymers in the polymer dots can be physically blended or chemically bonded (or chemically crosslinked). For example, the physically blended polymer dots can include polymers that are blended in the polymer dot and held together by non-covalent interactions. Chemically bonded polymer dots can include polymers that are covalently attached to each other in the polymer dot. The chemically bonded polymers can be covalently attached to each other prior to formation of the polymer dots.

For example, the polymer dots can include those that are directly functionalized and/or have low density functionalization.

Conjugated Polymer Dots and Functionalized Polymer Dots

This disclosure also provides for methods, compositions and kits using polymer dots and compositions thereof. In some cases, a variant of a polymer is a conjugated polymer, also referred to herein as functionalized chromophoric polymer dots.

Electrons, holes, or electronic energy, can be conducted along the conjugated structure of the conjugated polymer. In some cases, a large portion of the polymer backbone can be conjugated. In some cases, the entire polymer backbone can be conjugated. In some cases, the polymer can include conjugated structures in their side chains or termini. In some cases, the conjugated polymer can have conducting properties, e.g., the polymer can conduct electricity. In some cases, the conjugated polymer can have semiconducting properties, e.g., the polymers can exhibit a direct band gap, leading to an efficient absorption or emission at the band edge. In some cases, the chromophoric polymer dots can be described as nanoparticles including at least one condensed (or collapsed) conjugated polymer (e.g., semiconducting polymer) to form the nanoparticle structure.

A polymer, or a dot comprising the polymer, can be conjugated to another moiety with properties useful for therapy, diagnosis, imaging, or research. For example, a polymer or a dot can be conjugated to an additional moiety through a linker. The linker can be hydrophilic or hydrophobic. Non-limiting examples of linkers include a chemical bond, a small molecule, such as an amino acid, a functional group, such as an ester, and amide, a carbamate, an ether, an alkylene group, an alkenylene group, and alkynylene group, or an arylene group, or a polymer, such as a polyether, a polyester, a polyamide, a polycarbamate, a polyaryl, a polystyrene, or a polyolefin. In some cases, the linker is polyethylene glycol or polystyrene polyethylene glycol.

In some cases, the polymer can be conjugated to a hydrophilic moiety, for example, a hydrophilic functional group. Non-limiting examples of hydrophilic functional groups include carboxyl groups, hydroxyl groups, amino groups, amido groups, sulfhydryl groups, sulfate groups phosphate groups, and any hydrogen bond donor or acceptor.

The polymer can be conjugated to a reactive moiety, for example, an acid anhydride, an acid halide, a nucleophile, an electrophile, an electron donor, an electron acceptor, an olefin, an alkyne, an acidic group, a basic group, an oxidizing group, a reducing group, an electron transfer agent, or a photochemically-reactive species. Non-limiting examples of acid anhydrides include maleic anhydride and succinic anhydride, either of which being substituted or unsubstituted.

In various cases, the present disclosure provides for the use of "functionalized" polymer dots, and particularly as a means for modifying a surface of the chromophoric polymer dot. As used herein, the term "functionalized" in the context of chromophoric polymer dots refers to chromophoric polymer dots that are linked (e.g., covalently bonded) to one or more functional groups. As used herein, the term "functional group" refers to any chemical unit that can be attached, such as by any stable physical or chemical association, to the chromophoric polymer, thereby altering the surface of the chromophoric polymer dot, e.g., rendering the surface available for conjugation (e.g., bioconjugation). The functional group can be covalently linked to a backbone, side chain, or one of the terminating units of the chromophoric polymer. The functional group can be, without limitation, any the following: a aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof. In general, any other functional groups that are suitable for bioconjugation may be used. Such functional groups could be found by one of ordinary skill in the art, for example in Bioconjugate Techniques (Academic Press, New York, 1996 or later versions), which is herein incorporated by reference in its entirety for all purposes.

In some cases, functional groups of the present disclosure are selected from aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof.

In some cases, methods, compositions and kits are provided for the use of chromophoric polymer dots that have been functionalized. According to the present disclosure, chromophoric polymer dots can be functionalized in any manner that renders them suitable for further modification, e.g., bioconjugation, or for subsequent use in the detection of proteins or peptides. For example, a functional group can be linked (e.g., covalently bonded) to the backbone, the side chain, or one of the terminal units of a chromophoric polymer. In some cases, a monovalent polymer dot can include a single polymer molecule that includes only one functional group, e.g., at one of two terminal units of the single linear polymer molecule. A bivalent polymer dot can include a single polymer molecule that includes two functional groups, e.g., at each of the two terminal units of the single linear polymer molecule. A trivalent polymer dot can include a single polymer molecule that includes three functional groups, e.g., attachment of functional groups only to the three terminal units of a three-arm branched polymer. Similarly, branched polymer can be used in preparing other multivalent polymer dots, e.g., that have functional groups attached at the terminal units of four-arm, five-arm, six-arm, and branched polymers with higher numbers of branches.

In some cases, advantages can arise from using polymer dots that include a single polymer molecule having at least one functional group at a terminal unit. For example, the attachment of only one functional group to a terminal unit of a chromophoric polymer can be well controlled in polymer synthesis. For example, a chemical unit comprising a functional group can serve as a polymerization initiator as well as a growth catalyst in polymer synthesis, and in this way each polymer molecule includes just one functional group at the terminus. Attachment of functional groups only to the two terminal units of a linear chromophoric polymer can also be well controlled in polymer synthesis. For example, a chemical unit comprising a functional group can be used as a capping agent to terminate the polymer growth in polymer synthesis, thereby resulting in each linear polymer molecule including only two functional groups in the two terminal units. Similarly, the attachment of functional groups for multivalent polymer dots can be well controlled in polymer synthesis, e.g., functional groups can only be added to the three terminal units of a three-arm branched polymer.

In various cases, the polymer dot comprises a functional group attached to the polymer dot. In certain cases, the functional group is selected from a hydrophobic functional group, a hydrophilic functional group, or a combination thereof. In some cases, the functional group is suitable for bioconjugation.

In certain cases, the functional group is selected from aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, or a combination thereof.

In various cases, the biomolecule is a protein. In further cases, the biomolecule is an antibody or an avidin. In some cases, halides (e.g., fluorine) are attached to or incorporated into the chromophoric polymer dot structure. The particle size of the chromophoric polymer dots may be comparable to that of a Qdot, for example, greater than 80% the size of a Qdot. The semiconducting polymers in chromophoric polymer dots may be present at a total volume that is at least 50% of the per-particle volume and preferably greater than 80%. The semiconducting polymers in chromophoric polymer dots may be present at a weight concentration that is at least 50% of the per-particle weight and preferably greater than 80%. Chromophoric polymer dots can possess a hydrophobic polymer interior. In some cases, a chromophoric polymer dot has a halide (e.g., fluorine) content of less than 50% by mass. In some cases, the weight concentration is greater than 40%, 50%, 60%, 70%, 80%, 90% or 99%. In some cases, the weight concentration may be within the range of 40%-50%, 45%-55%, 50%-60%, 55%-65%, 60%-70%, 65%-75%, 70%-80%, 75%-85%, 80%-90%, 85%-95% or 90%-100%.

The particle size of the chromophoric polymer dots may be comparable to that of a Qdot, for example, greater than about 80% the size of a Qdot. The semiconducting polymers in chromophoric polymer dots may be present at a total volume that is at least 50% of the per-particle volume and preferably greater than about 80%. The semiconducting polymers in chromophoric polymer dots may be present at a weight concentration that is at least 50% of the per-particle weight and preferably greater than about 80%. Chromophoric polymer dots can possess a hydrophobic polymer interior. In some cases, a chromophoric polymer dot has a halide (e.g., fluorine) content of less than about 50% by mass. In some cases, the weight concentration is greater than about 40%, 50%, 60%, 70%, 80%, 90% or 99%. In some cases, the weight concentration may be within the range of about 40%-about 50%, about 45%-about 55%, about 50%-about 60%, about 55%-about 65%, about 60%-about 70%, about 65%-about 75%, about 70%-about 80%, about 75%-about 85%, about 80%-about 90%, about 85%-about 95% or about 90%-about 100%.

Bioconjugates of Polymer Dots

In various cases, the polymer dots of the present disclosure can be bioconjugated to facilitate the detection of proteins or peptides. In some cases, methods, compositions and kits are provided for the use of chromophoric polymer dots conjugated to biomolecules, such as for example, functionalization of chromophoric polymer dots wherein the biomolecule is attached to the chromophoric polymer dot either directly or indirectly by functional groups.

The term "biomolecule" is used to describe a synthetic or naturally occurring protein, glycoprotein, peptide, amino acid, metabolite, drug, toxin, nuclear acid, nucleotide, carbohydrate, sugar, lipid, fatty acid and the like. Chromophoric polymer dots conjugated to biomolecules are sometimes referred to herein as "bioconjugates." Bioconjugates can also include functionalized chromophoric polymer dots associated with biological particles such as viruses, bacteria, cells, and naturally occurring or synthetic vesicles such as liposomes. The functionalized chromophoric polymer dots can include one or more functional groups that are formed from the chromophoric polymer with one or two terminating functional groups, or low density side-chain functional groups.

In certain cases, the bioconjugates comprise a monovalent chromophoric polymer dot and a biomolecule, wherein the biomolecule is attached to the polymer dot either directly or indirectly by a functional group. The bioconjugates can also comprise monovalent chromophoric polymer dots associated with biological particles such as viruses, bacteria, cells, and naturally occurring or synthetic vesicles such as liposomes.

In some cases, the lyophilized chromophoric polymer dot compositions can include functionalized chromophoric polymer dots. The functionalized chromophoric polymer dots can have at least one functional group available for conjugation (e.g., bioconjugation). In some case, the lyophilized chromophoric polymer dot compositions can include a chromophoric polymer dot/biomolecule conjugate, wherein the biomolecule comprises a protein, an antibody, a nucleic acid molecule, a lipid, a peptide, an aptamer, and/or a drug. The biomolecule can be attached to the chromophoric polymer dot by any stable physical or chemical association.

In some cases of the present disclosure, the biomolecule is attached to the functional group of a monovalent chromophoric polymer dot via a covalent bond. For example, if the functional group of the polymer dot is a carboxyl group, a protein biomolecule can be directly attached to the polymer dot by cross-linking the carboxyl group with an amine group of the protein molecule.

In various cases of the present disclosure cross-linking agents can be utilized to facilitate bioconjugation of chromophoric polymer dots. As used herein, the term "cross-linking agent" is used to describe a compound or moiety that is capable of forming a chemical bond between molecular groups on similar or dissimilar molecules so as to covalently bond together the molecules. Examples of common cross-linking agents are known in the art. See, for example, Bioconjugate Techniques (Academic Press, New York, 1996 or later versions). Indirect attachment of the biomolecule to monovalent chromophoric polymer dots can occur through the use of "linker" molecules, for example, avidin, streptavidin, neutravidin, biotin or a like molecule.

In some cases, the polymer can be conjugated to a biomolecule, for example, a peptide, protein, an aptamer, an antibody, an enzyme, carbohydrate, nucleic acid, deoxyribonucleic acid, ribonucleic acid, or lipid. In some cases, a chromophoric polymer dot can be conjugated to a small molecule, a drug, a biomimetic, a pharmaceutical compound, an isotope, a radioisotope, or a chemical. In some cases, a polymer or dot is conjugated to streptavidin. In some cases, a polymer or dot is conjugated to biotin, or indirectly linked to biotin through streptavidin. In some cases, a polymer or dot is conjugated to a tag such as hemagglutanin (HA), vesicular stomatitis virus (VSV), glutathione 5-transferase (GST), histadine, more than one histadine, six histadines (6×His) or c-myc.

In some cases, methods, compositions and kits are provided for analysis of a target molecule (e.g., a protein) using polymer dots conjugated to biomolecules that specifically bind to the target.

In some cases, fluorescent chromophoric polymer dots are conjugated to one or more molecules that provide a function or other benefit, including without limitation, binding affinity for a target molecule.

In some cases, the target molecule is a protein of interest, and the biomolecule conjugated to a chromophoric polymer dot is a primary antibody that specifically binds to the target protein.

In other cases, the target molecule is a protein of interest bound to a primary antibody for said protein, and the biomolecule conjugated to a chromophoric polymer dot is a secondary antibody that specifically binds to the primary antibody.

As used herein, the term "biotin" refers to any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone.

As used herein, the term "avidin" refers to any biotin-binding protein other than an immunoglobulin that binds biotin including both natural proteins and recombinant and genetically engineered proteins. The term includes the two common biotin-binding proteins known as "egg white" or "avian" avidin and "streptavidin." Egg white or avian avidin, commonly referred to simply as avidin, is a protein that is a constituent of egg white and forms a noncovalent complex with biotin. Streptavidin is an avidin protein isolated from the actinobacterium *Streptomyces avidinii* and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin, and crosslinked avidin.

In some cases, fluorescent chromophoric polymer dots may be conjugated to one or more molecules that alter other properties of the chromophoric polymer dots, such as their size, fluorescence, hydrophobicity, non-specific binding or adsorption properties, and the like.

In some cases, conjugation of biomolecules to chromophoric polymer dots can include attachment of a functional group, including but not limited to attachment of carboxyl groups to chromophoric polymer dots. In some cases, carboxyl groups can be reacted to N-hydroxysuccinimide (NHS) in the presence of a carbodiimide such as 1-ethyl-3-[3-dimethylaminopropyl]carbodiimide hydrochloride (EDC) to produce amine-reactive esters of carboxylate groups for crosslinking with primary amine groups present on certain biomolecules.

In some cases, carboxylated chromophoric polymer dots are conjugated to a biomolecule, such as a protein, by mixing of the chromophoric polymer dots and the biomolecules, e.g., in a HEPES buffer (20 mM, pH=7.4) solution containing 0.1% PEG (MW3350). Formation of a peptide bond between the carboxyl groups on chromophoric polymer dots and the amine groups of the biomolecule can be catalyzed by EDC. However, due to the intrinsically hydrophobic nature of the chromophoric polymer dots, biomolecules tend to nonspecifically adsorb onto the particle surface. In some cases, Triton X-100 and/or bovine serum albumin (BSA) are introduced to reduce non-specific adsorption of a biomolecule onto the surface of a chromophoric polymer dot.

In some cases, a polymer dot may be conjugated to one or more of a plurality of labels. For example, the polymer dot may be conjugated to a labeling agent, such as a fluorescent labels (e.g., fluorescent dyes). In certain cases, the fluorescent label can have emission characteristics that are desired for a particular application. For example, the fluorescent label can be a fluorescent dye that has a emission wavelength maximum between a range of 500 nm to 1100 nm, between a range of 600 nm to 1000 nm, between a range of 600 to 800 nm, between a range of 650 nm to 850 nm, or between a range of 700 nm to 800 nm. For another example, the fluorescent label can be a fluorescent dye that has a emission wavelength maximum between a range of about 500 nm to about 1100 nm, between a range of about 600 nm to about 1000 nm, between a range of about 600 nm to about 800 nm, between a range of about 650 nm to about 850 nm, or between a range of about 700 nm to about 800 nm. One of ordinary skill in the art will appreciate the various dyes that can be used as detectable labels and that have the emission characteristics above.

Non limiting examples of fluorescent dyes that could be used as a conjugating molecule in the present disclosure include rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine, cyanine, indocarbocyanine, oxacarbocyanine, thiacarbocyanine, merocyanine, a cyanine dye (e.g., cyanine 2, cyanine 3, cyanine 3.5, cyanine 5, cyanine 5.5, cyanine 7), oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, xanthene dyes, sulfonated xanthenes dyes, Alexa Fluors (e.g., Alexa Fluor 594, Alexa Fluor 633, Alexa Fluor 647, Alexa Fluor 700), auramine, crystal violet, malachite green, tetrapyrrole derivatives, porphyrin, phtalocyanine, and bilirubin. In some cases, the dyes can be near-infrared dyes including, e.g., Cy5.5, IRdye 800, DyLight 750 or indocyanine green (ICG). In some cases, near infrared dyes can include a cyanine dye (e.g., cyanine 2, cyanine 3, cyanine 3.5, cyanine 5, cyanine 5.5, cyanine 7). In certain cases, the detectable label can include xanthene dyes or sulfonated xanthenes dyes, such as Alexa Fluors (e.g., Alexa Fluor 594, Alexa Fluor 633, Alexa Fluor 647, Alexa Fluor 700).

In some cases, polymer dots may be conjugated to peptides, often the peptides may be be conjugated to detectable labels. The detectable labels can be fluorescent labels (e.g., fluorescent dyes). In certain cases, the fluorescent label can have emission characteristics that are desired for a particular application. For example, the fluorescent label can be a fluorescent dye that has a emission wavelength maximum between a range of 500 nm to 1100 nm, between a range of 600 nm to 1000 nm, between a range of 600 to 800 nm, between a range of 650 nm to 850 nm, or between a range of 700 nm to 800 nm. For another example, the fluorescent label can be a fluorescent dye that has a emission wavelength maximum between a range of about 500 nm to about 1100 nm, between a range of about 600 nm to about 1000 nm, between a range of about 600 to about 800 nm, between a range of about 650 nm to about 850 nm, or between a range of about 700 nm to about 800 nm. One of ordinary skill in the art will appreciate the various dyes that can be used as detectable labels and that have the emission characteristics above.

Non limiting examples of fluorescent dyes that could be used as a conjugating molecule in the present disclosure include rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine, cyanine, indocarbocyanine, oxacarbocyanine, thiacarbocyanine, merocyanine, a cyanine dye (e.g., cyanine 2, cyanine 3, cyanine 3.5, cyanine 5, cyanine 5.5, cyanine 7), oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, xanthene dyes, sulfonated xanthenes dyes, Alexa Fluors (e.g., Alexa Fluor 594, Alexa Fluor 633, Alexa Fluor 647, Alexa Fluor 700), auramine, crystal violet, malachite green, tetrapyrrole derivatives, porphyrin, phtalocyanine, and bilirubin. In some cases, the dyes can be near-infrared dyes including, e.g., Cy5.5, IRdye 800, DyLight 750 or indocyanine green (ICG). In some cases, near infrared dyes can include a cyanine dye (e.g., cyanine 2, cyanine 3, cyanine 3.5, cyanine 5, cyanine 5.5, cyanine 7). In certain cases, the detectable label can include xanthene dyes or sulfonated xanthenes dyes, such as Alexa Fluors (e.g., Alexa Fluor 594, Alexa Fluor 633, Alexa Fluor 647, Alexa Fluor 700). If an antibody to the dye could be found the conjugated dyes could be used both as a tracking, detecting or visualizing marker and as a retrieval handle.

The peptides in the libraries of the present disclosure can also be conjugated to biotin. In addition of extension of half-life, biotin could also act as an affinity handle for retrieval of the peptides from tissues or other locations. In one case, the peptides can be conjugated, e.g., to a biotinidase resistant biotin with a PEG linker (e.g., NHS-dPEG4-Biotinidase resistant biotin). In some cases, fluorescent biotin conjugates that can act both as a detectable label and an affinity handle can be used. Non limiting examples of commercially available fluorescent biotin conjugates include Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, alexa fluor 488 biocytin, alexa flour 546, alexa fluor 549, lucifer yellow cadaverine biotin-X, Lucifer yellow biocytin, Oregon green 488 biocytin, biotin-rhodamine and tetramethylrhodamine biocytin. In some other examples, the conjugates could include chemiluminescent compounds, colloidal metals, luminescent compounds, enzymes, radioisotopes, and paramagnetic labels.

In addition to the examples described herein, in some cases other strategies and methods for conjugation of biomolecules to chromophoric polymer dots can be used, including those disclosed, e.g., in WO2011/057295 and WO2013/101902. Other strategies and methods for conjugation of biomolecules to chromophoric polymer dots can be found by one of ordinary skill in the art, for example in Bioconjugate Techniques (Academic Press, New York, 1996 or later versions).

Lyophilization Agents

The term "lyoprotectant," as used herein refers to a substance present in a lyophilized preparation. Typically it is present prior to the lyophilization process and persists in the resulting lyophilized preparation. Typically a lyoprotectant is added after the formation of the particles. If a concentration step is present, e.g., between formation of the particles and lyophilization, a lyoprotectant can be added before or after the concentration step. It can be used to protect nanoparticles, liposomes, and/or micelles during lyophilization, for example to reduce or prevent aggregation, particle collapse and/or other types of damage. In an aspect, the lyoprotectant is a cryoprotectant.

In an aspect, the lyoprotectant is a carbohydrate. The term "carbohydrate," as used herein refers to and encompasses monosaccharides, disaccharides, oligosaccharides and polysaccharides.

In an aspect, the lyoprotectant is a monosaccharide. The term "monosaccharide," as used herein refers to a single carbohydrate unit (e.g., a simple sugar) that can not be hydrolyzed to simpler carbohydrate units. Exemplary monosaccharide lyoprotectants include glucose, fructose, galactose, xylose, ribose and the like.

In an aspect, the lyoprotectant is a disaccharide. The term "disaccharide," as used herein refers to a compound or a chemical moiety formed by 2 monosaccharide units that are bonded together through a glycosidic linkage, for example through 1-4 linkages or 1-6 linkages. A disaccharide may be hydrolyzed into two monosaccharides. Exemplary disaccharide lyoprotectants include sucrose, trehalose, lactose, maltose and the like.

In an aspect, the lyoprotectant is an oligosaccharide. The term "oligosaccharide" as used herein refers to a compound or a chemical moiety formed by 3 to about 15, preferably 3 to about 10 monosaccharide units that are bonded together through glycosidic linkages, for example through 1-4 linkages or 1-6 linkages, to form a linear, branched or cyclic structure. Exemplary oligosaccharide lyoprotectants include cyclodextrins, raffinose, melezitose, maltotriose, stachyose acarbose, and the like. An oligosaccharide can be oxidized or reduced.

In an aspect, the lyoprotectant is a cyclic oligosaccharide. The term "cyclic oligosaccharide," as used herein refers to a compound or a chemical moiety formed by 3 to about 15, preferably 6, 7, 8, 9, or 10 monosaccharide units that are bonded together through glycosidic linkages, for example through 1-4 linkages or 1-6 linkages, to form a cyclic structure. Exemplary cyclic oligosaccharide lyoprotectants include cyclic oligosaccharides that are discrete compounds, such as α-cyclodextrin, β-cyclodextrin, or γ-cyclodextrin.

Other exemplary cyclic oligosaccharide lyoprotectants include compounds which include a cyclodextrin moiety in a larger molecular structure, such as a polymer that contains a cyclic oligosaccharide moiety. A cyclic oligosaccharide can be oxidized or reduced, for example, oxidized to dicarbonyl forms. The term "cyclodextrin moiety," as used herein refers to cyclodextrin (e.g., an α, -β-, or γ-cyclodextrin) radical that is incorporated into, or a part of, a larger molecular structure, such as a polymer. A cyclodextrin moiety can be bonded to one or more other moieties directly, or through an optional linker A cyclodextrin moiety can be oxidized or reduced, for example, oxidized to dicarbonyl forms.

Carbohydrate lyoprotectants, e.g., cyclic oligosaccharide lyoprotectants, can be derivatized carbohydrates. For example, in an aspect, the lyoprotectant is a derivatized cyclic oligosaccharide, e.g., a derivatized cyclodextrin, e.g., 2 hydroxy propyl-β-cyclodextrin, e.g., partially etherified cyclodextrins (e.g., partially etherified β-cyclodextrins) disclosed in U.S. Pat. No. 6,407,079, the contents of which are incorporated herein by this reference. Another example of a derivatized cyclodextran is β-cyclodextran sulfobutylether sodium.

An exemplary lyoprotectant is a polysaccharide. The term "polysaccharide," as used herein refers to a compound or a chemical moiety formed by at least 16 monosaccharide units that are bonded together through glycosidic linkages, for example through 1-4 linkages or 1-6 linkages, to form a linear, branched or cyclic structure, and includes polymers that comprise polysaccharides as part of their backbone structure. In backbones, the polysaccharide can be linear or cyclic. Exemplary polysaccharide lyoprotectants include glycogen, amylase, cellulose, dextran, maltodextrin and the like.

The term "derivatized carbohydrate," refers to an entity which differs from the subject non-derivatized carbohydrate by at least one atom. For example, instead of the —OH present on a non-derivatized carbohydrate the derivatized carbohydrate can have —OX, wherein X is an element other than H. Derivatives may be obtained through chemical functionalization and/or substitution or through de novo synthesis. The term "derivative" implies no process-based limitation.

A particle described herein may be prepared for dry storage via lyophilization, commonly known as freeze-drying. Lyophilization is a process which extracts water from a solution to form a granular solid or powder. The process is carried out by freezing the solution and subsequently extracting any water or moisture by sublimation under vacuum. Advantages of lyophilization include maintenance of substance quality and minimization of therapeutic compound degradation. Lyophilization may be particularly useful for developing pharmaceutical drug products that are reconstituted and administered to a patient by injection, for example parenteral drug products. Alternatively, lyophilization is useful for developing oral drug products, especially fast melts or flash dissolve formulations.

Lyophilization may take place in the presence of a lyoprotectant, e.g., a lyoprotectant described herein. In some aspects, the lyoprotectant is a carbohydrate (e.g., a carbohydrate described herein, such as, e.g., sucrose, cyclodextrin or a derivative of cyclodextrin (e.g. 2-hydroxypropyl-β-cyclodextrin)), salt, PEG, PVP or crown ether. Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β,α-trehalose, α,β-trehalose, sophorose, laminaribiose, gentiobiose, turanose, maltulose, palatinose, gentiobiulose, mannobiase, melibiose, melibiulose, rutinose, rutinulose, and xylobiose. Reconstitution shows equivalent DLS size distributions when compared to the stalling suspension. However, laser diffraction can detect particles of >10 μm in size in some reconstituted solutions. Further, SPOS also may detect >10 μm sized particles at a concentration above that of the FDA guidelines (104-105 particles/mL for >10 μm particles). A lyoprotectant comprising a cyclic oligosaccharide, may inhibit the rate of intermolecular aggregation of particles that include hydrophilic polymers such as PEG during their lyophilization and/or storage, and therefore, provide for extended shelf-life. Without wishing to be limited by theory, the mechanism for the cyclic oligosaccharide to prevent particle aggregation may be due to the cyclic oligosaccharide reducing or preventing the crystallization of the compound present in the particles during lyophilization. This may occur through the formation of an inclusion complex between a cyclic oligosaccharide and the compound. The inside cavity of cyclodextrin is lipophilic, while the outside of the cyclodextrin is hydrophilic. These properties may allow for the formation of inclusion complexes with other components of the particles described herein.

The present disclosure features liquid formulations and lyophilized preparations that comprise a cyclic oligosaccharide. In some aspects, the liquid formulation or lyophilized preparation can comprise at least two carbohydrates, e.g., a cyclic oligosaccharide (e.g., a cyclodextran or derivative thereof) and a non-cyclic oligosaccharide (e.g., a non-cyclic oligosaccharide less than about 10, 8, 6, 4 monosaccharides in length, e.g., a monosaccharide or disaccharide). In some aspects, the liquid formulations also comprise a reconstitution reagent.

Examples of suitable cyclic oligosaccharides, include, but are not limited to, α-cyclodextrins, β-cyclodextrins, such as 2-hydroxypropyl-β-cyclodextrins, β-cyclodextrin sulfobutylethers sodiums, γ-cyclodextrins, any derivative thereof, and any combination thereof.

In certain aspects, the cyclic carbohydrate, e.g., cyclic oligosaccharide, may be included in a larger molecular structure such as a polymer. Suitable polymers are disclosed herein with respect to the polymer composition of the particle. In such aspects, the cyclic oligosaccharide may be incorporated within a backbone of the polymer. See, e.g., U.S. Pat. Nos. 7,270,808 and 7,091,192, which disclose exemplary polymers that contain cyclodextrin moieties in the polymer backbone that can be used in accordance with the invention. The entire teachings of U.S. Pat. Nos. 7,270,808 and 7,091,192 are incorporated herein by reference. In some aspects, the cyclic oligosaccharide may contain at least one oxidized occurrence.

The cyclic oligosaccharide may be present in varying amounts in the formulations described herein. In certain aspects, the cyclic oligosaccharide to liquid formulation ratio is in the range of from about 0.75:1 to about 3:1 by weight. In preferred aspects, the cyclic oligosaccharide to total polymer ratio is in the range of from about 0.75:1 to about 3:1 by weight.

In preferred aspects, the formulation contains two or more carbohydrates, e.g., a cyclic oligosaccharide and a non-cyclic carbohydrate, e.g., a non-cyclic oligosaccharide, e.g., a non-cyclic oligosaccharide having 10, 8, 6, 4 or less monosaccharide units. As described herein, including a non-cyclic carbohydrate, e.g., a non-cyclic oligosaccharide, into a liquid formulation that is to be lyophilized can promote uptake of water by the resulting lyophilized preparation, and promote disintegration of the lyophilized preparation.

In preferred aspects, the lyophilized or liquid formulation comprises a cyclic oligosaccharide, such as an α-cyclodextrin, β-cyclodextrin, γ-cyclodextrin, any derivative thereof, and any combination thereof, and a non-cyclic oligosaccharide, e.g., a non-cyclic oligosaccharide described herein. In some preferred aspects, the lyoprotectant comprises a cyclic oligosaccharide, such as an α-cyclodextrin, β-cyclodextrin, γ-cyclodextrin, any derivative thereof, and any combination thereof, and the non-cyclic oligosaccharide is a disaccharide, such as sucrose, lactose, maltose, trehalose, and derivatives thereof, and a monosaccharide, such as glucose. In one preferred aspect, the lyoprotectant comprises a β-cyclodextrin or derivative thereof, such as 2-hydroxypropyl-β-cyclodextrin or β-cyclodextrin sulfobutylether; and the non-cyclic oligosaccharide is a disaccharide, such as sucrose. The β-cyclodextrin or derivative thereof and the non-cyclic oligosaccharide can be present in any suitable relative amounts. Preferably, the ratio of cyclic oligosaccharide to non-cyclic oligosaccharide (w/w) is from about 0.5:1.5 to about 1.5:0.5, and more preferably from 0.7:1.3 to 1.3:0.7. In some examples, the ratio of cyclic oligosaccharide to non-cyclic oligosaccharide (w/w) is 0.7:1.3, 1:0.7, 1:1, 1.3:1 or 1.3:0.7. When the liquid or lyophilized formulation comprises a particle described herein, the ratio of cyclic oligosaccharide plus non-cyclic oligosaccharide to polymer (w/w) is from about 1:1 to about 10:1, and preferably, from about 1.1 to about 3:1.

The present disclosure relates in part to the use of one or more ionic halide salts as an additional lyoprotectant to a sugar, such as sucrose, trehalose or mixtures thereof. Sugars may include disaccharides, monosaccharides, trisaccharides, and/or polysaccharides, and may include other excipients e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one aspect, about 1 to about 15 weight percent sucrose may be used with an ionic halide salt. In one aspect, the lyophilized pharmaceutical composition may comprise about 10 to about 100 mM sodium chloride. In another aspect, the lyophilized pharmaceutical composition may comprise about 100 to about 500 mM of divalent ionic chloride salt, such as calcium chloride or zinc chloride. In yet another aspect, the suspension to be lyophilized may further comprise a cyclodextrin, for example, about 1 to about 25 weight percent of cyclodextrin may be used.

Suitable cyclodextrin may include α-cyclodextrin, β-cyclodextrin γ-cyclodextrin, ear mixtures thereof. Exemplary cyclodextrins contemplated for use in the compositions disclosed herein include hydroxypropyl-β-cyclodextrin (HPβCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, cyclodextrin, glocosyl-β-cyclodextrin, and maltosyl-β-cyclodextrin In some aspects, a composition suitable for lyophilization is described herein, including polymer dots disclosed herein and a compound suitable for lyophilization, a sugar such as a monosaccharide, a disaccharide, or a polysaccharide. For example, the compound may be sucrose, glucose, manitol, tetrahelose, maltose or hydroxypropyl cyclodextran. In some aspects, one compound may be included in the composition. In other aspects, more than one compound may be included in the composition, for example, two compounds, three compounds, four compounds, five compounds, six compounds, seven compounds, eight compounds, nine compounds ten compounds or more than ten compounds may be included in the composition. In some aspects, the compound suitable for lyophilization may be in a solution comprising a diluent. For example, the solution may be water, a buffer, a solvent or the like.

In some aspects, the solution may comprise sucrose at greater than 0% w/v, greater than 1% w/v greater than 2% w/v, greater than 3% w/v, greater than 4% w/v, greater than 5% w/v, greater than 6% w/v, greater than 7% w/v, greater than 8% w/v, greater than 9% w/v, greater than 10% w/v, greater than 15% w/v, greater than 20% w/v, greater than 25% w/v, greater than 30% w/v, greater than 35% w/v, greater than 40% w/v, greater than 45% w/v, greater than 50% w/v, greater than 55% w/v or greater than 60% w/v. In some aspects, the solution may comprise sucrose at less than 0% w/v, less than 1% w/v, less than 2% w/v, less than 3% w/v, less than 4% w/v, less than 5% w/v, less than 6% w/v, less than 7% w/v, less than 8% v/v, less than 9% w/v, less than 10% w/v, less than 15% w/v, less than 20% w/v, less than 25% w/v, less than 30% w/v, less than 35% W/v, less than 40% w/v, less than 45% w/v, less than 50% w/v, less than 55% w/v or less than 60% w/v. In some aspects, the solution may comprise sucrose at about 0% w/v, about 1% w/v, about 2% w/v, about 3% w/v, about 4% w/v, about 5% w/v, about 6% w/v, about 7% about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise sucrose at 0% w/v, 1% w/v 2% w/v, 3% w/v, 4% w/v, 5% w/v-6% w/v, 7% w/v, 8% w/v, 9% w/v, 10% w/v, 15% w/v, 20% w/v, 25% w/v, 30% w/v, than 35% w/v, 40% w/v, 45% w/v, 50% w/v, 55% w/v or 60% w/v. In some aspects, the solution may comprise sucrose in the range of 0% w/v-10% w/v, 5% w/v 15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v-60% w/v. In some aspects, the solution may comprise sucrose in the range of about 0% w/v-about 10% w/v, about 5% w/v-about 15% w/v, about 5% w/v-about 20% w/v, about 10% w/v-about 30% w/v, about 15% w/v-about 30% w/v, about 15% w/v-about 40% w/v, about 20% w/v-about 50% w/v, about 25% w/v-about 60% w/v or 30% w/v-about 60% w/v.

In some aspects, the solution may comprise glucose at greater than 0% w/v, greater than 1% w/v, greater than 2% w/v, greater than 3% w/v, greater than 4% w/v, greater than 5% greater than 6% w/v, greater than 7% w/v, greater than 8% w/v, greater than 9% w/v, greater than 10% w/v, greater than 15% w/v, greater than 20% w/v, greater than 25% w/v, greater than 30% w/v, greater than 35% w/v, greater than 40% w/v, greater than 45% w/v, greater than 50% w/v, greater than 55% w/v or greater than 60% w/v. In some aspects, the solution may comprise glucose at less than 0% w/v, less than 1% w/v, less than 2% w/v, less than 3% w/v, less than 4% w/v, less than 5% w/v less than 6% w/v, less than 7% w/v, less than 8% w/v, less than 9% w/v, less than 10% w/v, less than 15% w/v, less than 20% w/v, less than 25% w/v, less than 30% w/v, less than 35% w/v, less than 40% w/v, less than 45% w/v, less than 50% w/v, less than 55% w/v or less than 60% w/v. In some aspects, the solution may comprise glucose at about 0% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise glucose at 0% w/v, 1% w/v, 2% w/v, 3% w/v, 4% w/v, 5% w/v, 6% w/v, 7% w/v, 8% w/v, 9% w/v, 10% w/v, 15% w/v, 20% w/v, 25% w/v, 30% w/v, than 35% w/v, 40% w/v, 45% w/v, 50% w/v, 55% w/v or 60% w/v. In some aspects, the solution may comprise glucose in the range of 0% w/v-10% w/v, 5% w/v-15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v-60% w/v. In some aspects, the solution may comprise glucose in the range of about 0% w/v-about 10% w/v, about 5% w/v-about 15% w/v, about 5% w/v-about 20% w/v, about 10% w/v-about 30% w/v, about 15% w/v-about 30% w/v, about 15% w/v-about 40% w/v, about 20% w/v-about 50% w/v, about 25% w/v-about 60% w/v or 30% w/v-about 60% w/v.

In some aspects, the solution may comprise mannitol at greater than 0% w/v, greater than 1% w/v greater than 2% w/v, greater than 3% w/v, greater than 4% w/v greater than 5% w/v, greater than 6% w/v, greater than 7% w/v, greater than 8% w/v, greater than 9% w/v, greater than 10% w/v, greater than 15% w/v, greater than 20% w/v, greater than 25% w/v greater than 30% w/v, greater than 35% w/v, greater than 40% w/v, greater than 45% w/v, greater than 50% w/v, greater than 55% w/v or greater than 60% w/v. In some aspects, the solution may comprise mannitol at less than 0% w/v, less than 1% w/v, less than 2% w/v, less than 3% w/v, less than 4% w/v, less than 5% w/v, less than 6% w/v, less than 7% w/v, less than 8% w/v, less than 9% w/v, less than 10% w/v, less than 15% w/v, less than 20% w/v less than 25% w/v, less than 30% w/v, less than 35% w/v, less than 40% w/v, less than 45% w/v, less than 50% w/v, less than 55% w/v or less than 60% w/v. In some aspects, the solution may comprise mannitol at about 0% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise mannitol at 0% w/v, 1% w/v, 2% w/v, 3% w/v, 4% w/v, 5% w/v, 6% w/v, 7% w/v, 8% w/v, 9% w/v, 10% w/v, 15% w/v, 20% w/v, 25% w/v, 30% w/v, than 35% w/v, 40% w/v, 45% w/v, 50% w/v, 55% w/v or 60% w/v. In some aspects, the solution may comprise mannitol in the range of 0% w/v-10% w/v, 5% w/v-15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v-60% w/v. In some aspects, the solution may comprise mannitol in the range of about 0% w/v-about 10% w/v, about 5% w/v-about 15% about 5% w/v-about 20% w/v, about 10% w/v-about 30% w/v, about 15% w/v-about 30% w/v, about 1% w/v-about 40% w/v, about 20% w/v-about 50% w/v, about 25% w/v-about 60% w/v or 30% w/v-about 60% w/v.

In some aspects, the solution may comprise tetrahelose at greater than 0% w/v, greater than 1% w/v, greater than 2% greater than 3% greater than 4% w/v, greater than 5% w/v greater than 6% w/v, greater than 7% w/v, greater than 8% w/v, greater than 9% w/v, greater than 10% w/v, greater than 15% w/v, greater than 20% w/v, greater than 25% w/v, greater than 30% greater than 35% w/v, greater than 40% w/v greater than 45% w/v, greater than 50% w/v, greater than 55% w/v or greater than 60% w/v. In some aspects, the solution may comprise tetrahelose at less than 0% w/v, less than 1% w/v less than 2% w/v, less than 3% w/v, less than 4% w/v, less than 5% w/v, less than 6% w/v, less than 7% w/v, less than 8% w/v, less than 9% w/v, less than 10% w/v, less than 15% w/v, less than 20% w/v, less than 25% w/v, less than 30% w/v, less than 35% w/v, less than 40% w/v, less than 45% w/v, less than 50% w/v, less than 55% w/v or less than 60% w/v. In some aspects, the solution may comprise tetrahelose at about 0% w/v, about 1% w/v, about 2% w/v, about 3% w/v, about 4% w/v, about 5% w/v, about 6% w/v, about 7% w/v, about 8% w/v, about 9% % iv, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise tetrahelose at 0% w/v, 1% w/v, 2% w/v, 3% w/v, 4% w/v, 5% w/v, 6% w/v, 7% 8% w/v, 9% w/v, 10% w/v, 15% w/v, 20% w/v, 25% w/v, 30% w/v, than 35% w/v, 40% w/v, 45% w/v, 50% w/v, 55% w/v or 60% w/v. In some aspects, the solution may comprise tetrahelose in the range of 0% w/v-10% w/v, 5% w/v-15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v-60% w/v. In some aspects, the solution may comprise tetrahelose in the range of about 0% w/v-about 10% w/v, about 5% w/v-about 15% w/v, about 5% w/v-about 20% w/v, about 10% w/v-about 30% w/v, about 15% w/v-about 30% w/v, about 15% w/v-about 40% w/v, about 20% w/v-about 50% w/v, about 25% w/v-about 60% w/v or 30% w/v-about 60% w/v.

In some aspects, the solution may comprise maltose at greater than 0% w/v, greater than 1% w/v, greater than 2% w/v, greater than 3% w/v, greater than 4% w/v, greater than 5% w/v, greater than 6% w/v, greater than 7% w/v, greater than 8% w/v, greater than 9% w/v, greater than 10% w/v, greater than 15% w/v, greater than 20% w/v, greater than 25% w/v, greater than 30% w/v, greater than 35% w/v, greater than 40% w/v, greater than 45% w/v, greater than 50% greater than 55% w/v or greater than 60% w/v. In some aspects, the solution may comprise maltose at less than 0% w/v, less than 1% w/v, less than 2% w/v, less than 3% w/v, less than 4% w/v, less than 5% w/v, less than 6% w/v, less than 7% w/v, less than 8% w/v, less than 9% w/v, less than 10% w/v, less than 15% w/v, less than 20% w/v, less than 25% w/v, less than 30% w/v, less than 35% w/v, less than 40% w/v, less than 45% w/v, less than 50% w/v, less than 55% w/v or less than 60% w/v. In some aspects, the solution may comprise maltose at about 0% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise maltose at 0% w/v, 1% w/v, 2% w/v, 3% w/v, 4% w/v, 5% w/v, 6% w/v, 7% w/v, 8% w/v, 9% w/v, 10% w/v, 15% w/v, 20% w/v, 25% w/v, 30% w/v, than 35% w/v, 40% w/v, 45% w/v, 50% w/v, 55% w/v or 60% w/v. In some aspects, the solution may comprise maltose in the range of 0% w/v-10% w/v, 5% w/v-15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v-60% w/v. In some aspects, the solution may comprise maltose in the range of about 0% w/v-about 10% w/v, about 5% w/v-about 15% w/v, about 5% w/v-about 20% w/v, about 10% w/v-about 30% w/v, about 15% w/v-about 30% w/v, about 15% w/v-about 40% w/v, about 20% w/v-about 50% w/v, about 25% w/v-about 60% w/v or 30% w/v-about 60% w/v.

In some aspects, the solution may comprise hydroxypropyl cyclodextran at greater than 0% w/v, greater than 1% w/v, greater than 2% w/v, greater than 3% w/v, greater than 4% w/v, greater than 5% w/v, greater than 6% w/v, greater than 7% w/v, greater than 8% w/v, greater than 9% w/v, greater than 10% w/v greater than 15% w/v, greater than 20% w/v, greater than 25% w/v, greater than 30% w/v, greater than 35% w/v, greater than 40% w/v, greater than 45% w/v, greater than 50% w/v, greater than 55% w/v or greater than 60% w/v. In some aspects, the solution may comprise hydroxypropyl cyclodextran at less than 0% w/v, less than 1% less than 2% w/v, less than 3% w/v less than 4% w/v, less than 5% w/v, less than 6% w/v, less than 7% w/v, less than 8% w/v, less than 9% w/v, less than 10% w/v, less than 15% w/v, less than 20% w/v, less than 25% w/v, less than 30% w/v, less than 35% w/v, less than 40% w/v less than 45% less than 50% w/v, less than 55% w/v or less than 60% w/v. In some aspects, the solution may comprise hydroxypropyl cyclodextran at about 0% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise hydroxypropyl cyclodextran at 0% w/v, 1% w/v, 2% w/v, 3% w/v, 4% w/v, 5% w/v, 6% w/v, 7% w/v, 8% w/v, 9% w/v, 10% w/v, 15% w/v, 20% w/v, 25% w/v, 30% w/v, than 35% w/v, 40% w/v, 45% w/v, 50% w/v, 55% w/v or 60% w/v. In some aspects, the solution may comprise hydroxypropyl cyclodextran in the range of 0% w/v-10% w/v, 5% w/v-15% w/v, 5% w/v-20% w/v, 10% w/v-30% w/v, 15% w/v-30% w/v, 15%) w/v-40% w/v, 20% w/v-50% w/v, 25% w/v-60% w/v or 30% w/v-60% w/v. In some aspects, the solution may comprise hydroxypropyl cyclodextran in the range of about 0% w/v-about 10% w/v, about 5% w/v-about 15% w/v, about 5% w/v-about 20% w/v, about 10% w/v-about 30% w/v, about 15% w/v-about 30% w/v, about 15% w/v-about 40% w/v, about 20% w/v-about 50% w/v, about 25% w/v-about 60% w/v or 30% w/v-about 60% w/v.

In some aspects, the solution may comprise sucrose and trehalose at greater than 0% w/v, greater than 1% w/v, greater than 2% w/v, greater than 3% w/v greater than 4% w/v greater than 5% w/v, greater than 6% w/v, greater than 7% w/v, greater than 8% w/v, greater than 9% w/v, greater than 10% w/v, greater than 15% w/v, greater than 20% w/v, greater than 25% w/v, greater than 30% w/v, greater than 35% w/v, greater than 40% w/v, greater than 45% w/v, greater than 50% w/v, greater than 55% w/v or greater than 60% w/v. In some aspects, the solution may comprise sucrose and trehalose at less than 0% w/v, less than 1% w/v, less than 2% w/v, less than 3% w/v less than 4% w/v, less than 5% w/v, less than 6%); w/v, less than 7% w/v, less than 8% less than 9% w/v, less than 10% w/v, less than 15% w/v, less than 20% w/v, less than 25% w/v, less than 30% w/v, less than 35% w/v, less than 40% w/v, less than 45% w/v, less than 50% w/v, less than 55% w/v or less than 60% w/v. In some aspects, the solution may comprise sucrose and trehalose at about 0% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise sucrose and trehalose at 0% w/v, 1% w/v, 2% w/v, 3% w/v, 4% w/v, 5% w/v, 6% w/v, 7% w/v, 8% w/v, 9% w/v, 10% w/v, 15% w/v, 20% w/v, 25% w/v, 30% w/v, than 35% w/v, 40% w/v, 45% w/v, 50% w/v, 55%); w/v or 60% w/v. In some aspects, the solution may comprise sucrose and trehalose in the range of 0% w/v-10% w/v, 5% w/v-15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v-60% w/v. In some aspects, the solution may comprise Sucrose and trehalose in the range of about 0% w/v-about 10% w/v, about 5% w/v-about 15% w/v, about 5% w/v-about 20% w/v, about 10% w/v-about 30% w/v, about 15% w/v-about 30% w/v, about 15% w/v-about 40% w/v, about 20% w/v-about 50% w/v, about 25% w/v-about 60% w/v or 30% w/v-about 60% w/v.

In some aspects, the solution may comprise sucrose and maltose at greater than 0% w/v, greater than 1% w/v, greater than 2% w/v, greater than 3% w/v, greater than 4% w/v, greater than 5% w/v, greater than 6% w/v, greater than 7% w/v, greater than 8% w/v, greater than 9% w/v, greater than 10% w/v greater than 15% w/v greater than 20% w/v, greater than 25% w/v, greater than 30% w/v, greater than 35% w/v, greater than 40% w/v, greater than 45% w/v, greater than 50% w/v, greater than 55% w/v or greater than 60% w/v. In some aspects, the solution may comprise sucrose and maltose at less than 0% w/v, less than 1% w/v, less than 2% w/v, less than 3% w/v, less than 4% w/v, less than 5% w/v, less than 6% w/v, less than 7% w/v, less than 8% w/v, less than 9% w/v, less than 10% w/v, less than 15% w/v, less than 20% w/v, less than 25% w/v, less than 30% w/v, less than 35% w/v, less than 40% w/v less than 45% w/v, less than 50% w/v, less than 55% w/v or less than 60% w/v. In some aspects, the solution may comprise sucrose and maltose at about 0% w/v, about 1% w/v, about 2% w/v, about 3% w, about 4% v/v, about 5% w/v, about 6% w/v, about 7% w/v, about 8% w/v, about 9% v/v, about 10% about 15% w/v, about 20% about 25% w/v, about 30% w/v, about 35% w/v, about 40% w/v, about 45% w/v, about 50% about 55% w/v or about 60% w/v. In some aspects, the solution may comprise sucrose and maltose at 0% w/v, 1% w/v, 2% w/v, 3% w/v, 4% w/v, 5% w/v, 6% w/v, 7% w/v, 8% w/v, 9% w, 10% w/v, 15% w/v, 20% w/v, w/v, 30% w/v, than 35% w/v, 40% w/v, 45% w/v, 50% w/v, 55% w/v or 60% w/v. In some aspects, the solution may comprise sucrose and maltose in the range of 0% w/v-0% w/v, 5% w/v-15% w/v, 5% w/v-20% w/v-10% w/v-30% w/v, 15% w/v-30% w/v-15% w/v-40% w/v, 20% w/v-50% w/v, 25% w/v-60% w/v or 30% w/v-60% w/v. In some aspects, the solution may comprise sucrose and maltose in the range of about 0%-about 10% w/v, about 5% w/v-about 15% w/v, about 5% w/v-about 20% w/v, about 10% w/v-about 30% w/v, about 15% w/v-about 30% w/v, about 15% w/v-about 40% w/v-about 20% w/v-about 50% w/v, about 25% w/v-about 60% w/v or 30% w/v-about 60% w/v.

In some aspects, the solution may comprise sucrose and glucose at greater than 0% w/v, greater than 1% w/v, greater than 2% w/v, greater than 3% w/v, greater than 4% w/v, greater than 5% w/v, greater than 6% w/v, greater than 7% w/v, greater than 8% w/v, greater than 9% w/v, greater than 10% greater than 15% w/v, greater than 20% w/v, greater than 25% w/v, greater than 30% w/v, greater than 35% w/v, greater than 40% w/v, greater than 45% w/v, greater than 50% w/v, greater than 55% w/v or greater than 60% w/v. In some aspects, the solution may comprise sucrose and glucose at less than 0% w/v, less than 1% w/v, less than 2% w/v, less than 3% w/v, less than 4% w/v, less than 5% w/v, less than 6% less than 7% w/v, less than 8% w/v less than 9% w/v, less than 10% w/v, less than 15% w/v, less than 20% w/v, less than 25% w/v, less than 30% w/v, less than 35% w/v, less than 40% w/v, less than 45% w/v, less than 50% w/v, less than 55% w/v or less than 60% w/v. In some aspects, the solution may comprise sucrose and glucose at about 0% w/v, about 1% w/v, about 2% w/v, about 3% w/v, about 4% w/v, about 5% w/v, about 6% w/v, about 7% w/v, about 8% w/v, about 9% w/v, about 10% w/v, about 15% about 20% w/v, about 25% w/v, about 30% w/v, about 35% w/v, about 40% w/v, about 45% w/v, about 50% w/v, about 55% w/v or about 60% w/v. In some aspects, the solution may comprise sucrose and glucose at 0% w/v, 1% w/v, 2% w/v, 3% w/v, 4% w/v, 5% w/v, 6% w/v, 7% w/v, 8% w/v, 9% w/v, 10% w/v, 15% w/v, 20% w/v, 25% w/v, 30% w/v, than 35% w/v, 40% w/v, 45% 50% w/v, 55% w/v or 60% w/v. In some aspects, the solution may comprise sucrose and glucose inure range of 0% w/v-10% w/v, 5% w/v-15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v-60% w/v. In some aspects, the solution may comprise sucrose and glucose in the range of about 0% w/v-about 10% w/v, about 5% w/v-about 15% w/v, about 5% w/v-about 20% w/v, about 10% w/v-about 30% w/v, about 15% w/v-about 30% w/v, about 15% w/v-about 40% w/v, about 20% w/v-about 50% w/v, about 25% w/v-about 60% w/v or 30% w/v-about 60% w/v.

In some aspects, the solution may comprise sucrose and mannitol at greater than 0% w/v, greater than 1% w/v, greater than 2% w/v, greater than 3% w/v, greater than 4% w/v greater than 5% greater than 6% w/v, greater than 7% w/v, greater than 8% w/v, greater than 9% w/v, greater than 10% w/v, greater than 15% w/v, greater than 20% w/v, greater than 25% w/v, greater than 30% w/v, greater than 35% w/v, greater than 40% w/v, greater than 45% w/v, greater than 50% w/v, greater than 55% w/v or greater than 60% w/v. In some aspects, the solution may comprise sucrose and mannitol at less than 0% w/v, less than 1% w/v, less than 2% w/v, less than 3% w/v, less than 4% w/v, less than 5% w/v, less than 6% w/v, less than 7% w/v, less than 8% w/v, less than 9% w/v, less than 10% w/v, less than 15% w/v, less than 20% w/v, less than 25% w/v, less than 30% w/v, less than 35% w/v, less than 40% w/v, less than 45% w/v, less than 50% w/v, less than 55% w/v or less than 60% w/v. In some aspects, the solution may comprise sucrose and mannitol at about 0% w/v, about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise sucrose and mannitol at 0% w/v, 1% w/v, 2% w/v, 3% w/v, 4%, 5% w/v, 6% w/v, 7% w/v, 8% w/v, 9% w/v, 10% w/v, 15% w/v, 20% w/v, 25% w/v, 30% w/v, than 35% w/v, 40% w/v, 45% w/v, 50% w/v, 55% w/v or 60% w/v. In some aspects, the solution may comprise sucrose and mannitol in the range of 0% w/v-10% w/v, 5% w/v-15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v-60% w/v. In some aspects, the solution may comprise Sucrose and mannitol in the range of about 0% w/v-about 10% w/v, about 5% w/v-about 15% w/v, about 5% w/v-about 20% w/v, about 10% w/v, about 30% w/v, about 15% w/v-about 30% w/v, about 15% w/v-about 40% w/v, about 20% w/v-about 50% w/v, about 25% w/v-about 60% w/v or 30% w/v-about 60% w/v.

In some aspects, the solution may comprise bovine serum album at greater than 0% w/v, greater than 1% w/v, greater than 2% w/v, greater than 3% w/v, greater than 4% w/v, greater than 5% w/v, greater than 6% w/v, greater than 7% w/v, greater than 8% w/v, greater than 9% w/v, greater than 10% w/v, greater than 15% w/v, greater than 20% w/v, greater than 25% w/v, greater than 30% w/v, greater than 35% w/v, greater than 40% w/v, greater than 45% w/v, greater than 50% w/v, greater than 55% w/v or greater than 60% w/v. In some aspects, the solution may comprise bovine serum albumin at less than 0% w/v, less than 1% w/v, less than 2% w/v, less than 3% w/v, less than 4% w/v, less than 5% w/v, less than 6% w/v, less than 7% w/v, less than 8% w/v, less than 9% w/v, less than 10% w/v, less than 15% w/v, less than 20% w/v, less than 25% w/v, less than 30% w/v, less than 35% w/v less than 40% w/v, less than 45% w/v, less than 50% w/v, less than 55% w/v or less than 60% w/v. In some aspects, the solution may comprise bovine serum albumin at about 0% w/v, about 1% w/v, about 2% v/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise bovine serum albumin at 0% w/v, 1% w/v, 2% w/v, 3% w/v, 4% w/v, 5% w/v, 6% w/v, 7% w/v, 8% w/v, 9% w/v, 10% w/v, 15% w/v, 20% w/v, 25% w/v, 30% w/v, than 35% w/v, 40% w/v, 45% w/v, 50% w/v, 55% w/v or 60% w/v. In some aspects, the solution may comprise bovine serum albumin in the range of 0% w/v-10% w/v, 5% w/v-15% w/v, 5% w/v-20% w/v, 10% w/v-30% w/v, 15% w/v-30% w/v, 15% w/v-40% w/v, 20% w/v-50% w/v, 25% w/v-60% w/v or 30% w/v 60% w/v. In some aspects, the solution may comprise bovine serum albumin in the range of about 0% w/v-about 10% w/v, about 5% w/v-about 15% w/v, about 5% w/v-about 20% w/v, about 10% w/v-about 30% w/v, about 15% w/v-about 30% w/v, about 15% w/v-about 40% w/v, about 20% w/v-about 50% w/v, about 25% w/v-about 60% w/v, or 30% w/v about 60% w/v.

In some aspects, the solution may comprise mannitol, trehalose, hydroxypropyl cyclodextran and bovine serum albumin at greater than 0% w/v greater than 1% w/v greater than 2% w/v, greater than 3% w/v, greater than 4% w/v, greater than 5% w/v, greater than 6% w/v, greater than 7% w/v, greater than 8% w/v, greater than 9% w/v, greater than 10% w/v, greater than 15% w/v, greater than 20% w/v, greater than 25% w/v, greater than 30% w/v, greater than 35% w/v, greater than 40% w/v greater than 45% w/v, greater than 50% w/v, greater than 55% w/v or greater than 60% w/v. In some aspects, the solution may comprise mannitol, trehalose, hydroxypropyl cyclodextran and bovine serum albumin at less than 0% w/v, less than 1% w/v less than 2% w/v, less than 3% w/v, less than 4% w/v, less than 5% w/v, less than 6% WV, less than 7% w/v, less than 8% w/v, less than 9% w/v less than 10% w/v, less than 15% less than 20% w/v, less than 25% w/v, less than 30% w/v, less than 35% w/v, less than 40% w/v, less than 45% w/v, less than 50% w/v, less than 55% w/v or less than 60% w/v. In some aspects, the solution may comprise mannitol, trehalose, hydroxypropyl cyclodextran and bovine serum albumin at about 0% w/v, about 1% w/v about 2% w/v, about 3% w/v, about 4% w/v, about 5% w/v, about 6% w/v, about 7% w/v, about 8% w/v, about 9% w/v, about 10% w/v, about 15% w/v, about 20% w/v, about 25% w/v, about 30% w/v, about 35% w/v, about 40% w/v, about 45% w/v, about 50% w/v, about 55% w/v or about 60% w/v. In some aspects, the solution may comprise mannitol, trehalose, hydroxypropyl cyclodextran and bovine serum albumin at 0% w/v, 1% w/v, 2% w/v, 3% w/v, 4% w/v, 5% w/v, 6% w/v, 7% w/v, 8% w/v, 9% w/v, 10% w/v, 15% w/v-20% w/v, 25% w/v, 10% w/v, than 35% w/v, 40% w/v, 45% w/v, 50% w/v, 55% w/v or 60% w/v. In some aspects, the solution may comprise mannitol, trehalose, hydroxypropyl cyclodextran and bovine serum albumin in the range of 0% w/v-10% w/v, 5% w/v-15% w/v, 5% w/v-20% w/v, 10% w/v-30% W/V, 15% w/v-30% w/v-15% w/v-40% w/v, 20% w/v-50% w/v, 25% w/v-60% w/v, or 30% w/v-60% w/v. In some aspects, the solution may comprise mannitol, trehalose, hydroxypropyl cyclodextran and bovine serum albumin in the range of about 0% w/v-about 10% w/v, about 5% w/v-about 15% w/v, about 5% w/v-about 20% w/v, about 10% w/v-about 30% w/v-about 15% w/v-about 30% w/v, about 15% w/v-about 40% w/v, about 20% w/v-about 50% w/v, about 25% w/v-about 60% w/v or 30% w/v about 60% w/v.

Described herein is a polymer dot formulation comprising a plurality of disclosed polymer dots, sucrose, an ionic halide, and water. In some aspects, the composition of the polymer dots/sucrose/water/ionic halide may be 3-40%/10-40%/20-95%/0.1-10% (w/w/w/w) or 5-10%/10-15%/80-90%/1-10% (w/w/w/w). In some aspects, the composition of the polymer dots/sucrose/water/ionic halide may be about 3-40%/10-40%/20-95%/0.1-10% (w/w/w/w) or about 5-10%/10-15%/80-90%/1-10% (w/w/w/w). In some aspects, the composition of the polymer dots/sucrose/Water may be 3-40%/10-40%/20-95%/(w/w/w) or 5-10%%10-15%/80-90% (w/w/w). In some aspects, the composition of the polymer dots/sucrose/water/ionic halide may be about 3-40%/10-40%/20-95% (w/w/w) or about 5-10%/10-15%/80-90% (w/w/w). In some aspects, the solution may comprise ionic halide at greater than 0 mM, greater than 1 mM, greater than 2 mM, greater than 3 mM, greater than 4 mM, greater than 5 mM, greater than 6 mM greater than 7 mM, greater than 8 mM, greater than 9 mM, greater than 10 mM, greater than 15 mM, greater than 20 mM, greater than 25 mM, greater than 30 mM, greater than 35 mM, greater than 40 mM, greater than 45 mM, greater than 50 mM, greater than 55 mM, greater than 60 mM, greater than 65 mM, greater than 70 mM, greater than 75 greater than 80 nM, greater than 85 mM, greater than 90 mM, greater than 95 mM, greater than 100 mM, greater than 110 mM, greater than 120 mM, greater than 130 mM, greater than 140 mM, greater than 150 mM, greater than 160 mM, greater than 170 mM, greater than 180 mM, greater than 190 mM or greater than 200 mM. In some aspects, the solution may comprise ionic halide at less than 0 mM, less than 1 mM, less than 2 mM, less than 3 mM, less than 4 mM, less than 5 mM, less than 6 mM, less than 7 mM, less than 8 mM, less than 9 mM, less than 10 mM, less than 15 mM, less than 20 mM, less than 25 mM, less than 30 mM, less than 35 mM, less than 40 mM, less than 45 mM, less than 50 mM, less than 55 mM, less than 60 mM less than 65 mM, less than 70 mM, less than 75 mM, less than 80 nM, less than 85 mM, less than 90 mM, less than 95 mM, less than 100 mM, less than 110 mM, less than 120 mM less than 130 mM, less than 140 mM, less than 150 mM, less than 160 mM, less than 170 mM, less than 180 mM, less than 190 mM or less than 200 mM. In some aspects, the solution may comprise ionic halide at about 0 mM, about 1 mM, about 2 mM, about 3 mM, about 4 mM, about 5 mM, about 6 mM about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM about 65 mM, about 70 mM, about 75 mM, about 80 nM, about 85 mM, about 90 mM, about 95 mM, about 100 mM, about 110 mM, about 120 mM, about 130 mM, about 140 mM about 150 mM about 160 mM about 170 mM, about 180 mM, about 190 mM or about 200 mM, In some aspects, the solution may comprise ionic halide at 0 mM, 1 mM, 2 mM 3 mM, 4 mM, 5 mM, 6 mM, 7 mM, 8 mM 9 mM, 10 mM, 15 mM, 20 mM, 25 mM 30 mM, 35 mM, 40 mM, 45 mM, 50 mM, 55 mM, 60 mM about 65 mM, 70 mM, 75 mM, 80 mM, 85 mM, g 90 mM, 95 mM, 100 mM, 110 mM, 120 mM, 130 mM, 140 mM, 150 mM, 160 mM, 170 mM, 180 mM, 190 mM or 200 mM. In some aspects, the solution may comprise ionic halide in the range of 0 mM-10 mM 5 mM-15 mM, 5 mM-20 mM, 10 mM-30 mM, 15 mM-30 mM, 15 mM-40 mM, 20 mM-50 mM, 25 mM-60 mM, 30 mM-60 mM, 40 mM-80 mM, 50 mM-100 mM, 60 mM-120 mM, 70 mM-130 mM, 80 mM-140 mM, 90 mM-150 mM, 100 mM-160 mM, 110 mM-170 mM, 120 mM-180 mM, 130 mM-190 mM or 140 mM-200 mM, In some aspects, the solution may comprise ionic halide in the range of about 0 mM-about 10 mM, about 5 mM-about 15 mM, about 5 mM-about 20 mM, about 10 mM-about 30 mM, about 15 mM-about 30 mM, about 15 mM-about 40 mM, about 20 mM-about 50 mM, about 25 mM-about 60 mM, 30 mM-about 60 mM, 40 mM-80 mM, about 50 mM-100 mM, about 60 mM-120 mM, about 70 mM-130 mM, about 80 mM-140 mM, about 90 mM-150 mM, about 100 mM-160 mM, about 110 mM-170 mM, about 120 mM-180 mM, about 130 mM-190 mM or 140 mM-200 mM.

In some aspects, the solution may comprise sodium chloride at greater than 0 mM, greater than 1 mM, greater than 2 mM, greater than 3 mM, greater than 4 mM, greater than 5 mM, greater than 6 mM, greater than 7 mM, greater than 8 mM, greater than 9 mM, greater than 10 mM, greater than 15 mM, greater than 20 mM, greater than 25 mM, greater than 30 mM, greater than 35 mM, greater than 40 mM, greater than 45 mM, greater than 50 mM, greater than 55 mM, greater than 60 mM, greater than 65 mM, greater than 70 mM, greater than 75 mM, greater than 80 nM, greater than 85 mM, greater than 90 mM, greater than 95 mM, greater than 100 mM, greater than 110 mM, greater than 120 mM, greater than 130 mM, greater than 140 mM, greater than 150 mM, greater than 160 mM, greater than 170 mM, greater than 180 mM, greater than 190 mM or greater than 200 mM. In some aspects, the solution may comprise sodium chloride at less than 0 mM, less than 1 mM, less than 2 mM, less than 3 mM less than 4 mM, less than 5 mM, less than 6 mM, less than 7 mM, less than 8 mM, less than 9 mM, less than 10 mM less than 15 mM, less than 20 mM, less than 25 mM, less than 30 mM, less than 35 mM, less than 40 mM, less than 45 mM, less than 50 mM, less than 55 mM, less than 60 mM less than 65 mM, less than 70 mM, less than 75 mM, less than 80 nM, less than 85 mM less than 90 mM, less than 95 mM, less than 100 mM, less than 110 mM, less than 120 mM, less than 130 mM, less than 140 mM, less than 150 mM, less than 160 mM, less than 170 mM, less than 180 mM, less than 190 mM or less than 200 mM. In some aspects, the solution may comprise sodium chloride at about 0 mM, about 1 mM, about 2 mM, about 3 mM about 4 mM about 5 mM about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM about 65 mM, about 70 mM about 75 mM, about 80 nM, about 85 mM, about 90 mM, about 95 mM, about 100 mM, about 110 mM, about 120 mM, about 130 mM about 140 mM, about 150 mM, about 160 mM, about 170 mM, about 180 mM, about 190 mM or about 200 mM. In some aspects, the solution may comprise sodium chloride at 0 mM, 1 mM, 2 mM, 3 mM, 4 mM, 5 mM, 6 mM, 7 mM, 8 mM, 9 mM, 10 mM, 15 mM, 20 mM, 25 mM, 30 mM, 35 mM, 40 mM, 45 mM, 50 mM, 55 mM, 60 mM about 65 mM, 70 mM, 75 mM, 80 mM, 85 mM, g 90 mM, 95 mM, 100 mM, 110 mM, 120 mM, 130 mM, 140 mM, 150 mM, 160 mM, 170 mM, 180 mM, 190 mM or 200 mM. In some aspects, the solution may comprise sodium chloride in the range of 0 mM-10 mM, 5 mM-15 mM, 5 mM-20 mM, 10 mM-30 mM, 15 mM-30 mM, 15 mM-40 mM, 20 mM-50 mM, 25 mM-60 mM, 40 mM-80 mM, 50 mM-100 mM, 60 mM-120 mM, 70 mM-130 mM, 80 mM-140 mM, 90 mM-150 mM, 100 mM-160 mM, 110 mM-170 mM, 120 mM-180 mM, 130 mM-190 mM or 140 mM-200 mM. In some aspects, the solution may comprise sodium chloride in the range of about 0 mM-about 10 mM, about 5 mM-about 15 mM, about 5 mM-about 20 mM, about 10 mM-about 30 mM, about 15 mM-about 30 mM, about 15 mM-about 40 mM, about 20 mM-about 50 mM, about 25 mM-about 60 mM, 30 mM-about 60 mM, 40 mM-80 mM, about 50 mM-100 mM, about 60 mM-120 mM, about 70 mM-130 mM-about 80 mM-140 mM about 90 mM-150 mM, about 100 mM-160 mM, about 110 mM-170 mM, about 20 mM-180 mM, about 130 mM-190 until or 140 mM-200 mM.

In some aspects, the solution may comprise magnesium chloride at greater than 0 mM, greater than 1 mM, greater than 2 mM, greater than 3 mM, greater than 4 mM, greater than 5 mM, greater than 6 mM, greater than 7 mM, greater than 8 mM, greater than 9 mM, greater than 10 mM, greater than 15 mM, greater than 20 until, greater than 25 mM, greater than 30 mM, greater than 35 mM, greater than 40 mM, greater than 45 mM, greater than 50 mM, greater than 55 mM, greater than 60 mM, greater than 65 mM, greater than 70 mM, greater than 75 mM, greater than 80 nM, greater than 85 mM, greater than 90 mM, greater than 95 mM, greater than 100 mM, greater than 110 mM, greater than 120 mM, greater than 130 mM, greater than 140 mM, greater than 150 mM, greater than 160 mM, greater than 170 mM, greater than 180 mM, greater than 190 mM or greater than 200 mM. In some aspects, the solution may comprise magnesium chloride at less than 0 mM, less than 1 mM, less than 2 mM, less than 3 mM, less than 4 mM, less than 5 mM, less than 6 mM, less than 7 mM, less than 8 mM less than 9 mM less than 10 mM, less than 15 mM, less than 20 mM less than 25 mM, less than 30 mM less than 35 mM, less than 40 mM, less than 45 mM, less than 50 mM, less than 55 mM, less than 60 mM less than 65 mM, less than 70 mM, less than 75 mM, less than 80 nM, less than 85 mM, less than 90 mM, less than 95 mM, less than 100 mM, less than 110 mM, less than 120 mM, less than 130 mM, less than 140 mM, less than 150 mM, less than 160 mM, less than 170 mM, less than 180 mM, less than 190 mM or less than 200 mM. In some aspects, the solution may comprise magnesium chloride at about 0 mM, about 1 mM, about 2 mM, about 3 mM, about 4 mM about 5 mM, about 6 mM, about 7 mM, about 8 mM, about 9 mM about 10 mM, about 15 mM, about 20 mM about 25 mM, about 30 mM, about 35 mM, about 40 mM, about 45 mM, about 50 mM, about 55 mM, about 60 mM about 65 mM, about 70 mM, about 75 mM, about 80 nM, about 85 mM, about 90 mM, about 95 mM, about 100 mM, about 110 mM, about 120 mM, about 130 mM, about 140 mM, about 150 mM, about 160 mM about 170 mM, about 180 mM, about 190 mM or about 200 mM. In some aspects, the solution may comprise magnesium chloride at 0 mM, 1 mM, 2 mM, 3 mM, 4 mM, 5 mM, 6 mM, 7 mM, 8 mM 9 mM, 10 mM, 15 mM, 20 mM, 25 mM, 30 mM, 35 mM, 40 mM, 45 mM, 50 mM, 55 mM, 60 mM about 65 mM, 70 mM, 75 mM, 80 nM, 85 mM, g 90 mM, 95 mM, 100 mM, 110 mM, 120 mM, 130 mM, 140 mM, 150 mM, 160 mM, 170 mM, 180 mM, 190 or 200 mM. In some aspects, the solution may comprise magnesium chloride in the range of 0 mM-10 mM, 5 mM-15 mM, 5 mM-20 mM, 10 mM-30 mM, 15 mM-30 mM, 15 mM-40 mM, 20 mM-50 mM, 25 mM-60 mM, 30 mM-60 mM, 40 mM-80 mM, 50 mM-100 mM, 60 mM-120 mM, 70 mM-130 mM, 80 mM-140 mM, 90 mM-150 mM, 100 mM-160 mM, 110 mM-170 mM, 120 mM-180 mM, 130 mM-190 mM or 140 mM-200 mM. In some aspects, the solution may comprise magnesium chloride in the range of about 0 mM-about 10 mM, about 5 mM-about 15 mM, about 5 mM-about 20 mM, about 10 mM-about 30 mM, about 15 mM-about 30 mM, about 15 mM-about 40 mM, about 20 mM-about 50 mM, about 25 mM-about 60 mM, 30 mM-about 60 mM, 40 mM-80 mM, about 50 mM-100 mM, about 60 mM-120 mM, about 70 mM-130 mM, about 80 mM-140 mM, about 90 mM-150 mM, about 100 mM-160 mM, about 110 mM-170 mM, about 120 mM-180 mM, about 130 mM-190 mM or 140 mM-200 mM In some aspects, the polymer-agent conjugate, particle or composition is provided in lyophilized form and is reconstituted prior to administration to a subject. The lyophilized polymer-agent conjugate, particle or composition can be reconstituted by a diluent solution, such as a salt or saline solution, e.g., a sodium chloride solution having a pH between 6 and 9, lactated Ringer's injection solution, or a commercially available diluent, such as PLASMA-INTE, A Injection pH 7.4® (Baxter, Deerfield, Ill.).

In some aspects, a lyophilized formulation includes a lyoprotectant or stabilizer to maintain physical and chemical stability by protecting the particle and active from damage from crystal formation and the fusion process during freeze-drying. The lyoprotectant or stabilizer can be one or more of polyethylene glycol (PEG), a PEG lipid conjugate (e.g., PEG-ceramide or D-alpha-tocopheryl polyethylene glycol 1000 succinate), poly(vinyl alcohol) (PVA), poly(vinylpyrrolidone) (PVP), polyoxyethylene esters, poloxamers, polysorbates, polyoxyethylene esters, lecithins, saccharides, oligosaccharides, polysaccharides, carbohydrates, cyclodextrans (e.g. 2-hydroxypropyl-β-cyclodextrin) and polyols (e.g., trehalose, mannitol, sorbitol, lactose, sucrose, glucose and dextran), salts and crown ethers.

In certain aspects, the lyophilized preparations may be reconstituted with a reconstitution reagent. In some aspects, a suitable reconstitution reagent may be any physiologically acceptable liquid. Suitable reconstitution reagents include, but are not limited to, water, 5% Dextrose Injection, Lactated Ringer's and Dextrose Injection, or a mixture of equal parts by volume of Dehydrated Alcohol, USP and a nonionic surfactant, such as a polyoxyethylated castor oil surfactant available from GAF Corporation, Mount Olive, N.J., under the trademark, Cremophor EL. To minimize the amount of surfactant in the reconstituted solution, only a sufficient amount of the vehicle may be provided to form a solution of the lyophilized preparation. Once dissolution of the lyophilized preparation is achieved, the resulting solution may be further diluted prior to injection with a suitable parenteral diluent. Such diluents are well known to those of ordinary skill in the art. These diluents are generally available in clinical facilities. Examples of typical diluents include, but are not limited to, Lactated Ringer's Injection, 5% Dextrose Injection, Sterile Water for Injection, and the like. However, because of its narrow pH range, pH 6.0 to 7.5, Lactated Ringer's Injection is most typical. Per 100 mL, Lactated Ringer's Injection contains Sodium Chloride USP 0.6 g, Sodium Lactate 0.31 g, Potassium chloride USP 0.03 g and Calcium Chloride.sub.2H.sub.20 USP 0.02 g. The osmolarity is 275 mOsmol/L, which is very close to isotonicity.

Accordingly, a liquid formulation can be a resuspended or rehydrated lyophilized preparation in a suitable reconstitution reagent. Suitable reconstitution reagents include physiologically acceptable carriers, e.g., a physiologically acceptable liquids as described herein. Preferably, resuspension or rehydration of the lyophilized preparations forms a solution or suspension of particles which have substantially the same properties (e.g., average particle diameter, size distribution, polydispersity, drug concentration) and morphology of the original particles in the liquid formulation of the present invention before lyophilization, and further maintains the therapeutic agent to polymer ratio of the original liquid formulation before lyophilization. In certain aspects, about 50% to about 100%, preferably about 80% to about 100%, of the particles in the resuspended or rehydrated lyophilized preparation maintain the size distribution and/or drug to polymer ratio of the particles in the original liquid formulation. Preferably, the properties and polydispersity of the particles in the formulation produced by resuspending a lyophilized preparation do not differ from the properties, and polydispersity of the particles in the original solution or suspension prior to lyophilization by more than about 5%, more than about 10%, more than about 15%, more than about 20%, more than about 15%, more than about 30%, more than about 35%, more than about 40%, more than about 45%, or more than about 50%.

Preferably liquid formulations of this aspect contain particles, and are characterized by a higher polymer concentration (the concentration of polymer(s) that form the particle) than can be lyophilized and resuspended using either a lyoprotectant that comprises one or more carbohydrates (e.g., a cyclic oligosaccharide and/or a non-cyclic oligosaccharide). For example, the polymer concentration can be at least about 20 mg/mL, at least about 25 mg/mL, at least about 30 mg/mL, at least about 31 mg/mL, at least about 32 mg/mL, at least about 33 mg/mL, at least about 34 mg/mL, at least about 35 mg/mL, at least about 36 mg/mL, at least about 37 mg/mL, at least about 38 mg/mL, at least about 39 mg/mL, at least about 40 mg/mL, at least about 45 mg/mL, at least about 50 mg/mL, at least about 55 mg/mL, at least about 60 mg/mL, at least about 65 mg/mL, at least about 70 mg/mL, at least about 75 mg/mL, at least about 80 mg/mL, at least about 85 mg/mL, at least about 90 mg/mL, at least about 95 mg/mL, are at least about 100 mg/mL. For example, the liquid formulation can be a reconstituted lyophilized preparation.

Lyophilization of Polymer Dots

The present disclosure is in part based on the surprising discovery that chromophoric polymer dots can be lyophilized and stored while still retaining optical properties, colloidal stability, and, for chromophoric polymer dot bioconjugates, cell-targeting capability during storage. While not being limited to any particular theory, it is thought that during lyophilization, lyoprotectant molecules can form a surface layer, and diffuse into the chromophoric polymer dot and or chromophoric polymer dot shell as water is driven out of the particle. As a result, the colloidal stability and photophysical properties of the particles can be retained, and in some cases, improved after lyophilization and being reconstituted into a solution after storage.

The lyophilized compositions and methods described herein can provide several useful results for compositions and methods relating to chromophoric polymer dots. In some cases, the presence of lyoprotectant molecules in chromophoric polymer dot and or chromophoric polymer dot shells can, e.g., reduce chain-chain interactions. As described further herein, the reduced chain-chain interactions may increase fluorescence quantum yield and narrow the emission bandwidth of previously lyophilized chromophoric polymer dots compared to unlyophilized chromophoric polymer dots.

For example, by using flow cytometry, lyophilized chromophoric polymer dot bioconjugates retained biological targeting properties during the labeling of cells. In one example, cells labeled with lyophilized chromophoric polymer dot bioconjugates composed of PFBT, which were stored for 6 months at −80° C., were ~22% brighter than those labeled with identical but unlyophilized chromophoric polymer dot bioconjugates. Lyophilization may be a useful approach for storing and shipping chromophoric polymer dot bioconjugates, an important practical consideration for ensuring chromophoric polymer dots are widely adopted for use in biomedical research.

The process of lyophilization can be performed in a variety of ways that are generally well known in the art. Lyophilization can, e.g., include a dehydration process used to preserve the chromophoric polymer dots described herein and to, e.g., make them more convenient for transport. Lyophilization generally works by freezing the chromophoric polymer dots and then, e.g., reducing the surrounding pressure to allow the frozen water in the material to sublimate directly from the solid phase to the gas phase.

The present disclosure further includes methods for preparing lyophilized chromophoric polymer dot compositions. The methods can include lyophilizing the chromophoric polymer dots in a variety of solutions described herein. Lyophilizing the chromophoric polymer dots in solution can include freezing the chromophoric polymer dot solutions at any suitable temperature to produce a lyophilized chromophoric polymer dot composition.

The present disclosure includes methods for lyophilizing the chromophoric polymer dots to form lyophilized chromophoric polymer dot compositions. The lyophilizing can include freezing the chromophoric polymer dots in aqueous solutions that include a variety of constituents described herein. Freezing can be performed at a variety of temperatures. For example, the chromophoric polymer dots compositions can be lyophilized by freezing at temperatures at or below about −10° C., at or below about −20° C., at or below about −30° C., at or below about −40° C., at or below about −50° C., at or below about −60° C., at or below about −70° C. or at or below about −80° C. Freezing can be performed at a variety of temperatures. For example, the chromophoric polymer dots compositions can be lyophilized by freezing at temperatures at or below −10° C., at or below −20° C., at or below −30° C., at or below −40° C., at or below −50° C., at or below −60° C., at or below −70° C. or at or below −80° C.

The concentrations of the chromophoric polymer dots in the solutions prior to lyophilization can also vary over a wide range. In certain cases, the concentration of the chromophoric polymer dots in the solutions prior to lyophilization can depend on the size of the chromophoric polymer dots. Smaller chromophoric polymer dots can have a higher concentration than larger chromophoric polymer dots. In some cases, the chromophoric polymer dots can be present in the solution prior to lyophilization in the millimolar, micromolar, nanomolar, or picomolar range. In some cases, the chromophoric polymer dots can be present between about 1 nM-100 µM, between about 100 nM-1 µM, between about 100 nM-750 nM, between about 100 nM-500 nM, between about 1 nM-500 nM, 1-100 nM, between about 1-75 nM, between about 1-50 nM, between about 1-25 nM, between about 1-20 nM, between about 1-15 nM, between about 1-10 nM, or between about 1-5 nM. In some cases, the chromophoric polymer dots can be present between 1 nM-100 µM, between 100 nM-1 µM, between 100 nM-750 nM, between 100 nM-500 nM, between 1 nM-500 nM, 1-100 nM, between 1-75 nM, between 1-50 nM, between 1-25 nM, between 1-20 nM, between 1-15 nM, between 1-10 nM, or between 1-5 nM.

In some cases, the methods, e.g., can include providing a solution including chromophoric polymer dots in combination with other constituents, and freezing the solution at a desired temperature, e.g., at about −80° C. or −20° C. for a period of time.

In some cases, the present disclosure includes method of producing a lyophilized composition including chromophoric polymer dot with reactive functional groups. The reactive functional groups can include amine reactive functional group such as succinimidyl ester, sulfhydryl reactive functional group such as maleimide, or reactive functional group for click chemistry such as alkyne, azide, strained alkyne, cyclooctyne, and phosphine groups.

In some cases, the methods can include, e.g., (a) combining (i) a solution of conjugated polymer with reactive functional groups in good solvent with (ii) a poor solvent, followed by evaporation of the poor solvent, thereby forming a first suspension comprising the chromophoric polymer dots; and (b) lyophilizing the suspension, thereby forming the lyophilized composition of chromophoric polymer dots with reactive functional groups, wherein the chromophoric polymer dots are fluorescent nanoparticles including at least one condensed conjugated polymer.

Good solvents can include, e.g., a solvent in which the conjugated polymer is soluble without forming a chromophoric polymer dot. Poor solvents can include, e.g., a solvent in which the conjugated polymer is poorly soluble and thereby forms chromophoric polymer dots after introduction into the poor solvent.

The lyophilization methods above can be used, e.g., to produce amine-reactive chromophoric polymer dots such as chromophoric polymer dots with succinimidyl ester. These chromophoric polymer dots, e.g., can be directly mixed with a biomolecule (e.g., a protein) to form chromophoric polymer dot bioconjugates. In some cases, EDC/NHS can be used to activate a chromophoric polymer dot-COOH to form chromophoric polymer dot-NHS, after which lyophilization can be performed. In certain cases, NHS-terminated conjugated polymer can be synthesized, injected into a solution of methanol or ethanol to form chromophoric polymer dots.

The chromophoric polymer dots can then be lyophilized to produce lyophilized chromophoric polymer dot-NHS.

The lyophilized compositions can include a variety of lyophilization agents (e.g., cryoprotectants and/or lyoprotectants). The constituents can include molecules that are soluble in water, e.g., at a concentration sufficient to provide lyophilization of the chromophoric polymer dots. In some cases, carbohydrates may be used as cryoprotectants. Examples of carbohydrates can include monosaccharides, oligosaccharides (e.g., disaccharides), and polysaccharides, as well as compounds derived from monosaccharides, oligosaccharides, and polysaccharides.

In some cases, the lyophilized chromophoric polymer dot compositions can include a variety of constituents, such as, but not limited to, a monosaccharide, an oligosaccharide (e.g., a disaccharide), and/or a polysaccharide. Sugar alcohols and/or other suitable cryoprotectants and/or lyoprotectants can be used.

The constituents added to facilitate lyophilization (e.g., cryoprotectants and/or lyoprotectants), e.g., can be present in a chromophoric polymer dot solution prior to lyophilization at concentrations ranging between about 1% to about 50%, between about 5% to about 40%, between about 10% to about 30%, between about 1% and about 20%, and between about 10% and about 20%. In some cases, the concentrations may range between 1% and 50%, between 5% and 40%, between 10% and 30%, between 1% and 20%, and between 10% and 20%. In some cases, the constituents added to facilitate lyophilization (e.g., cryoprotectants and/or lyoprotectants), e.g., can be present in a chromophoric polymer dot solution prior to lyophilization at concentrations ranging between 1% to 50%, between 5% to 40%, between 10% to 30%, between 1% and 20%, and between 10% and 20%. In some cases, the concentrations may range between 1% and 50%, between 5% and 40%, between 10% and 30%, between 1% and 20%, and between 10% and 20%. In some cases, several different types (e.g., two or more) of cryoprotectants and/or lyoprotectants can be present at the same or different concentrations in the chromophoric polymer dots solutions prior to lyophilization.

In some cases, a monosaccharide can be a molecule having the general formula: $C_x(H_2O)y$, $x \leq 3$. Examples of monosaccharides can include, but are not limited to, glucose, fructose, galactose, xylose, ribose, and the like.

In some cases, an oligosaccharide can be a short monosaccharide polymer that contains, e.g., between 2 to 30 monosaccharide units. An oligosaccharide can include, e.g., a disaccharide that refers to, e.g., molecules that are formed when two monosaccharides are joined together and, e.g., a molecule of water is removed. Examples of disaccharides can include, but are not limited to, sucrose, lactulose, lactose, maltose, trehalose, cellobiose, and the like. Other oligosaccharides can include, but are not limited to, trisaccharides (e.g., raffinose), tetrasaccharides (e.g., stachyose), and pentasaccharides (e.g., verbacose).

A variety of concentration ranges can be used for the disaccharides. The disaccharides, e.g., can be present in a chromophoric polymer dot solution prior to lyophilization at concentrations ranging between about 1% to about 50%, between about 5% to about 40%, between about 10% to about 30%, between about 1% and about 20%, and between about 10% and about 20%. In some cases, the disaccharides, e.g., can be present in a chromophoric polymer dot solution prior to lyophilization at concentrations ranging between 1% to 50%, between 5% and 40%, between 10% and 30%, between 1% and 20%, and between 10% and 20%. In some cases, e.g., sucrose can be present in a chromophoric polymer dot solution prior to lyophilization at between about 10% w/v to about 20% w/v. In some cases, e.g., sucrose can be present in a chromophoric polymer dot solution prior to lyophilization at between 10% w/v and 20% w/v. Concentrations of the various disaccharides can be optimized using the techniques described herein. For example, a chromophoric polymer dot solution can be prepared, lyophilized, resuspended, and then the properties (e.g., size) of the chromophoric polymer dots can be analyzed to confirm that no aggregation occurred due to lyophilization. In some cases, the disaccharides, e.g., can be present in a chromophoric polymer dot solution prior to lyophilization at concentrations ranging between 1% and 50%, between 5% and 40%, between 10% and 30%, between 1% and 20%, and between 10% and 20%. In some cases, e.g., sucrose can be present in a chromophoric polymer dot solution prior to lyophilization at between 10% w/v to 20% w/v. Concentrations of the various disaccharides can be optimized using the techniques described herein.

In one case, the present disclosure includes lyophilized chromophoric polymer dot compositions including a disaccharide, such as, but not limited to, sucrose, trehalose, maltose, lactose, and any acceptable salt or hydrated forms. In some cases, one type of disaccharide is used (e.g., sucrose). In certain cases, at least two types of disaccharide can be used (e.g., trehalose and sucrose). The disaccharide(s) can be added to a solution of chromophoric polymer dots prior to lyophilization.

In some cases, the concentration of the disaccharide(s) in the solution can vary over a wide range that can be tailored through known techniques to produce useful lyophilized chromophoric polymer dot compositions that when reconstituted provide chromophoric polymer dots having about the same particle diameter.

In some cases, a polysaccharide can be a monosaccharide polymer beyond the length of and oligosaccharide, e.g., a polymer including more than 30 monosaccharide units described above.

Sugar alcohols may also be used with the lyophilized compositions provided herein. For example, sugar alcohol can be a hydrogenated form of carbohydrate, whose carbonyl group (aldehyde or ketone, reducing sugar) has been reduced to a primary or secondary hydroxyl group. Sugar alcohols have the general formula $H(HCHO)_{n+1}H$. Example sugar alcohols can include, but are not limited to, alditols (e.g., xylitol, mannitol or sorbitol) and the like.

The present disclosure further includes other cryoprotectants and/or lyoprotectants that can be used in the lyophilized compositions provided herein. Example lyoprotectants can include, e.g., glycine, hydroxypropyl-β-cyclodextrin, gelatin and aerosil.

Other constituents can also be included in the solutions and lyophilized compositions described herein. For example, polyethylene glycol or other water soluble polymers can be used. Buffers (e.g., Tris, HEPES, and other known buffers) and salts (e.g., NaCl) can also be used.

In some cases, the present disclosure includes methods of producing a lyophilized composition including lyophilizing a suspension of chromophoric polymer dots, thereby forming the lyophilized composition of chromophoric polymer dots, wherein the chromophoric polymer dots are fluorescent nanoparticles including at least one condensed conjugated polymer. In some cases, the methods can include, e.g., (a) combining (i) a liquid including chromophoric polymer dots with (ii) a first aqueous solution, thereby forming a first suspension comprising the chromophoric polymer dots; and (b) lyophilizing the suspension, thereby forming the lyophilized composition of chromophoric polymer dots, wherein the chromophoric polymer dots are fluorescent nanoparticles including at least one condensed conjugated polymer.

In an exemplary case, the compositions described herein can include a lyophilized composition comprising fluorescent nanoparticles, the fluorescent nanoparticles comprising at least one condensed conjugated polymer, often comprising a carbohydrate. For example, the carbohydrate may comprise a monosaccharide, a disaccharide, an oligosaccharide, a polysaccharide, or a combination thereof, often comprising a disaccharide. For example, the disaccharide may be selected from the group consisting of sucrose, trehalose dihydrate, maltose monohydrate, and lactose monohydrate, often the disaccharide is sucrose. For example, sucrose may be present between about 10% w/v and 20% w/v. In some cases, the disaccharide is present between about 1% w/v and 50% w/v. In other cases, the disaccharide is present between about 10% w/v and 20% w/v. For example, sucrose may be present between 10% w/v and 20% w/v. For example, sucrose may be present between 10% w/v and 20% w/v. In some cases, the disaccharide is present between 1% w/v and 50% w/v. In other cases, the disaccharide is present between 10% w/v and 20% w/v. For example, sucrose may be present between 10% w/v and 20% w/v. In some cases, the disaccharide is present between 1% w/v and 50% w/v. In other cases, the disaccharide is present between 10% w/v and 20% w/v.

In some cases, the composition may comprise an alditol, hydroxypropyl-cyclodextrin, BSA, or a combination thereof.

The compositions described herein may include fluorescent nanoparticles that may be conjugated to a biomolecule. Often, the biomolecule comprises a protein, an antibody, a nucleic acid molecule, a lipid, a peptide, an aptamer, a drug, or a combination thereof. For example, the biomolecule comprises streptavidin.

In some cases, the compositions described herein may comprise fluorescent nanoparticles that may comprise similar or increased quantum yield when dispersed in an aqueous solution as compared to the fluorescent nanoparticles prior to lyophilization. In some cases, the quantum yield of lyophilized chromophoric polymer dots can be similar to unlyophilized chromophoric polymer dots. For example, the quantum yield of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the quantum yield of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. Often, the fluorescent nanoparticles comprise a similar particle diameter when dispersed in an aqueous solution as compared to the particle diameter of fluorescent nanoparticles prior to lyophilization. In some cases, the particle diameter of lyophilized chromophoric polymer dots can be similar to unlyophilized chromophoric polymer dots. For example, the particle diameter of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the particle diameter of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots.

In some cases, the compositions described herein may be at least one condensed conjugated polymer comprises a semiconducting polymer. Often, the one condensed conjugated polymer is selected from the group consisting of a fluorene polymer, a flourene-based polymer or copolymer, a phenylene vinylene polymer or copolymer, a phenylene ethynylene polymer or copolymer, a BODIPY-based polymer or copolymer. For example, the at least one condensed conjugated polymer is selected from the group consisting of poly(9,9-dihexylfluorenyl-2,7-diyl) (PDHF), Poly(9,9-dioctylfluorenyl-2,7-diyl) (PFO), poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-Di-2-thienyl-2,1,3-benzothiadiazole)] (PF-0.1TBT)), and poly[2-methoxy-5-(2-ethylhexyloxy)-1,4-phenylenevinylene] (MEH-PPV), poly[2-methoxy-5-(2-ethylhexyloxy)-1,4-(1-cyanovinylene-1,4-phenylene)] (CN-PPV), BODIPY 570, BODIPY 590, and BODIPY 690.

Often, the fluorescent nanoparticles include a plurality of polymers, for example, the fluorescent nanoparticles comprise a polymer, wherein the polymer includes a plurality of polymers. In some cases, at least 50% of the plurality of polymers includes conjugated polymers.

In some cases, the compositions described herein may comprise fluorescent nanoparticles have an average diameter of less than about 30 nm as measured by dynamic light scattering. In some cases, the quantum yield of the fluorescent particles after dispersion in a solution is higher than the unlyophilized fluorescent particles. In some cases, the full width half maximum of the emission bandwidth of the fluorescent particles after dispersion in a solution is narrower than the full width half maximum emission bandwidth of the unlyophilized fluorescent particles.

In an exemplary case, the compositions described herein may comprise a lyophilized composition comprising fluorescent nanoparticles, wherein the fluorescent nanoparticles are lyophilized. Often, the compositions may comprise a carbohydrate. For example, the carbohydrate comprises a monosaccharide, a disaccharide, an oligosaccharide, a polysaccharide, or a combination thereof. In a preferred case, the compositions may comprise a disaccharide, for example, the disaccharide may be present between about 1% w/v and 50% w/v or between about 10% w/v and 20% w/v. For example, the disaccharide is selected from the group consisting of sucrose, trehalose dihydrate, maltose monohydrate, and lactose monohydrate. Often, the disaccharide is sucrose, for example, sucrose is present between about 10% w/v and 20% w/v. In another preferred case, the compositions may comprise a disaccharide, for example, the disaccharide may be present between 1% w/v and 50% w/v or between 10% w/v and 20% w/v. For example, the disaccharide is selected from the group consisting of sucrose, trehalose dihydrate, maltose monohydrate, and lactose monohydrate. Often, the disaccharide is sucrose, for example, sucrose is present between 10% w/v and 20% w/v.

The compositions may further comprise an alditol, hydroxypropyl-cyclodextrin, BSA, or a combination thereof.

In some cases, the compositions described herein may comprise fluorescent nanoparticles that may be conjugated to a biomolecule. For example, the biomolecule comprises a protein, an antibody, a nucleic acid molecule, a lipid, a peptide, an aptamer, a drug, or a combination thereof, often, the biomolecule comprises streptavidin.

In some cases, the compositions described herein may comprise fluorescent nanoparticles that may comprise similar or increased quantum yield when dispersed in an aqueous solution as compared to the fluorescent nanoparticles prior to lyophilization. In some cases, the quantum yield of lyophilized chromophoric polymer dots can be similar to unlyophilized chromophoric polymer dots. For example, the quantum yield of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the quantum yield of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. Often, the fluorescent nanoparticles comprise a similar particle diameter when dispersed in an aqueous solution as compared to the particle diameter of fluorescent nanoparticles prior to lyophilization. In some cases, the particle diameter of lyophilized chromophoric polymer dots can be similar to unlyophilized chromophoric polymer dots. For example, the particle diameter of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the particle diameter of lyophilized chromophoric polymer dots can be about 80%, about 85%, about 90%, about 91%, about 92%, about 93%, about 94%, about 95%, about 96%, about 97%, about 98%, about 99% or 100% similar to unlyophilized chromophoric polymer dots.

In some cases, the compositions may include at least one condensed conjugated polymer comprises a semiconducting polymer. Often, the at least one condensed conjugated polymer is selected from the group consisting of a fluorene polymer, a flourene-based polymer or copolymer, a phenylene vinylene polymer or copolymer, a phenylene ethynylene polymer or copolymer, a BODIPY-based polymer or copolymer. For example, the at least one condensed conjugated polymer is selected from the group consisting of poly(9,9-dihexylfluorenyl-2,7-diyl) (PDHF), Poly(9,9-dioctylfluorenyl-2,7-diyl) (PFO), poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-Di-2-thienyl-2,1,3-benzothiadiazole)] (PF-0.1TBT)), and poly[2-methoxy-5-(2-ethylhexyloxy)-1,4-phenylenevinylene] (MEH-PPV), poly[2-methoxy-5-(2-ethylhexyloxy)-1,4-(1-cyanovinylene-1,4-phenylene)] (CN-PPV), BODIPY 570, BODIPY 590, and BODIPY 690.

Often, the fluorescent nanoparticles include a plurality of polymers. For example, the fluorescent nanoparticles may comprise a polymer, wherein the polymer includes a plurality of polymers. In some cases, at least 50% of the plurality of polymers includes conjugated polymers.

The compositions described herein may further comprise fluorescent nanoparticles that may have an average diameter of less than about 30 nm as measured by dynamic light scattering. In some cases, the quantum yield of the fluorescent particles after dispersion in a solution is higher than the unlyophilized fluorescent particles. In some cases, the full width half maximum of the emission bandwidth of the fluorescent particles after dispersion in a solution is narrower than the full width half maximum emission bandwidth of the unlyophilized fluorescent particles.

The compositions described herein may further include lyophilized composition of fluorescent nanoparticles prepared by any one of the methods and/or the kits described herein. In some cases, a lyophilized composition may be prepared by the method comprising lyophilizing a suspension comprising fluorescent particles, thereby forming the lyophilized composition of fluorescent nanoparticles, wherein the fluorescent nanoparticles are chromophoric polymer dots comprising a polymer.

In some cases, the lyophilized composition of the methods of lyophilizing may comprise freezing the suspension at a temperature below about −10° C., below about −20° C., below about −30° C., or below about −40° C. In an exemplary case, lyophilizing may comprise freezing the suspension at a temperature at or around −80° C.

The composition may further include, before lyophilizing, combining (i) a liquid comprising fluorescent nanoparticles with (ii) a first aqueous solution, thereby forming the suspension comprising fluorescent nanoparticles. Often, the method further comprises combining (i) a liquid comprising a fluorescent nanoparticle with (ii) a first aqueous solution, thereby forming the suspension comprising fluorescent nanoparticles.

In some cases, the first aqueous solution comprises a lyophilization agent. For example, the lyophilization agent may be a carbohydrate. In some cases, the carbohydrate may comprise a monosaccharide, a disaccharide, an oligosaccharide, a polysaccharide, or a combination thereof. For example, the carbohydrate may be selected from a monosaccharide, a disaccharide, an oligosaccharide, a polysaccharide, or a combination thereof. Often, the suspension comprises a disaccharide, for example, the disaccharide may be present between about 10% w/v and 20% w/v or the disaccharide may be present between about 1% w/v and 50% w/v. In some cases, the disaccharide may be selected from the group consisting of sucrose, trehalose dihydrate, maltose monohydrate, and lactose monohydrate. For example, the disaccharide is sucrose. In some cases, sucrose may be present between about 10% w/v and 20% w/v.

The composition may further include an alditol, hydroxypropyl-cyclodextrin, bovine serum albumin or a combination thereof. In some cases, the lyophilized composition may further be mixed with a second aqueous solution, thereby forming a second suspension comprising the fluorescent nanoparticles dispersed in the second aqueous solution. Often, the dispersed fluorescent nanoparticles in the second aqueous solution have a similar or increased quantum yield as compared to unlyophilized fluorescent nanoparticles. For example, the dispersed fluorescent nanoparticles in the second aqueous solution have a similar particle diameter as compared to the particle diameter unlyophilized fluorescent nanoparticles. In some cases, the dispersed fluorescent nanoparticles have an average diameter of less than about 30 nm as measured by dynamic light scattering.

The composition may further include a polymer that comprises a semiconducting polymer. Often, the polymer is selected from the group consisting of a fluorene polymer, a flourene-based polymer, a phenylene vinylene polymer, and a phenylene ethynylene polymer. For example, the polymer is selected from the group consisting of poly(9,9-dihexyl-fluorenyl-2,7-diyl) (PDHF), Poly(9,9-dioctylfluorenyl-2,7-diyl) (PFO), poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-Di-2-thienyl-2,1,3-benzothiadiazole)] (PF-0.1TBT)), and poly[2-methoxy-5-(2-ethylhexyloxy)-1,4-phenylenevinylene] (MEH-PPV), poly[2-methoxy-5-(2-ethylhexyloxy)-1,4-(1-cyanovinylene-1,4-phenylene)] (CN-PPV), BODIPY 570, BODIPY 590, and BODIPY 690.

In some cases, the compositions may have a quantum yield of the fluorescent particles after dispersion in a solution is higher than the unlyophilized fluorescent particles. In some cases, the full width half maximum of the emission bandwidth of the fluorescent particles after dispersion in a solution is narrower than the full width half maximum emission bandwidth of the unlyophilized fluorescent particles.

The lyophilized compositions described herein may comprise fluorescent nanoparticles which further comprise at least one condensed conjugated polymer. In some cases, the polymer is a condensed conjugated polymer. In some cases, the fluorescent nanoparticles comprise semiconducting polymers. In other cases, the fluorescent polymer comprises a BODIPY derivative. For example, the BODIPY derivative has the structure of Formula (I):

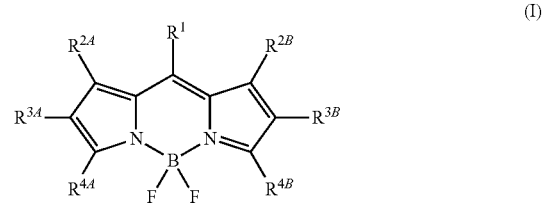

wherein each of $R^1$, $R^{2A}$, $R^{2B}$, $R^{3A}$, $R^{4A}$ and $R^{4B}$ is independently selected from hydrogen, alkyl, aralkyl, aryl, and alkoxy-aryl, and wherein the BODIPY derivative is integrated into the chromophoric polymer by attachment to $R^1$, $R^{2A}$, $R^{2B}$, $R^{3A}$, $R^{4A}$ and $R^{4B}$, or a combination thereof.

In some cases, the lyophilized composition comprising the fluorescent nanoparticles may have an average diameter of between 1 nm and 100 nm as measured by dynamic light scattering. For example, the fluorescent nanoparticles have an average diameter of less than about 100 nm as measured by dynamic light scattering. For another example, the fluorescent nanoparticles have an average diameter of less than about 100 nm, about 90 nm, about 80 nm, about 70 nm, about 60 nm, about 50 nm, about 40 nm, about 30 nm, about 20 nm, less than about 10 nm, less than about 5 nm or less than about 1 nm as measured by dynamic light scattering. For example, the fluorescent nanoparticles have an average diameter of less than 100 nm as measured by dynamic light scattering. For another example, the fluorescent nanoparticles have an average diameter of less than 100 nm, 90 nm, 80 nm, 70 nm, 60 nm, 50 nm, 40 nm, 30 nm, 20 nm, less than 10 nm or less than 5 nm or less than 1 nm as measured by dynamic light scattering. For example, the fluorescent nanoparticles have an average diameter of about 100 nm as measured by dynamic light scattering. For another example, the fluorescent nanoparticles have an average diameter of about 100 nm, 90 nm, 80 nm, 70 nm, 60 nm, 50 nm, 40 nm, 30 nm, 20 nm, 10 nm, 5 nm or about 1 nm as measured by dynamic light scattering. For example, the fluorescent nanoparticles have an average diameter of 100 nm as measured by dynamic light scattering. For another example, the fluorescent nanoparticles have an average diameter of 100 nm, 90 nm, 80 nm, 70 nm, 60 nm, 50 nm, 40 nm, 30 nm, 20 nm, 10 nm, 5 nm or 1 nm as measured by dynamic light scattering.

For another example, the fluorescent nanoparticles have an average diameter of less than about 100 nm-less than about 80 nm, less than about 90 nm-less than about 70 nm, less than about 80 nm-less than about 60 nm, less than about 70 nm-less than about 50 nm, less than about 60 nm-less than about 40 nm, less than about 50 nm-less than about 30 nm, less than about 40 nm-less than about 20 nm, less than about 30 nm-less than about 10 nm, less than about 20 nm-less than about 1 nm, less than about 30 nm-less than about 5 nm, less than about 10 nm-less than about 5 nm, less than about 10 nm-less than about 1 nm as measured by dynamic light scattering. For another example, the fluorescent nanoparticles have an average diameter of less than 100 nm-less than 80 nm, less than 90 nm-less than 70 nm, less than 80 nm-less than 60 nm, less than 70 nm-less than 50 nm, less than 60 nm-less than 40 nm, less than 50 nm-less than 30 nm, less than 40 nm-less than 20 nm, less than 30 nm-less than 10 nm, less than 20 nm-less than 1 nm, less than 30 nm-less than 5 nm, less than 10 nm-less than 5 nm, less than 10 nm-less than 1 nm as measured by dynamic light scattering. For another example, the fluorescent nanoparticles have an average diameter of about 100 nm-about 80 nm, about 90 nm-about 70 nm, about 80 nm-about 60 nm, about 70 nm-about 50 nm, about 60 nm-about 40 nm, about 50 nm-about 30 nm, about 40 nm-about 20 nm, about 30 nm-about 10 nm, about 20 nm-about 1 nm, about 30 nm-about 5 nm, about 10 nm-about 5 nm, about 10 nm-about 1 nm as measured by dynamic light scattering. For another example, the fluorescent nanoparticles have an average diameter of 100 nm-80 nm, 90 nm-70 nm, 80 nm-60 nm, 70 nm-50 nm, 60 nm-40 nm, 50 nm-30 nm, 40 nm-20 nm, 30 nm-10 nm, 20 nm-1 nm, 30 nm-5 nm, 10 nm-5 nm, 10 nm-1 nm as measured by dynamic light scattering.

In some cases, the at least one condensed conjugated polymer is conjugated to a biomolecule. Often, the biomolecule comprises a protein, an antibody, a nucleic acid molecule, a lipid, a peptide, an aptamer, a drug, or a combination thereof. For example, the biomolecule may comprise streptavidin. For another example, the biomolecule may comprise an aptamer. For another example, the biomolecule may comprise a nucleic acid. For another example, the biomolecule may comprise an antibody.

The methods described herein may include a method of producing a lyophilized composition, comprising lyophilizing a suspension comprising fluorescent particles, thereby forming the lyophilized composition of fluorescent nanoparticles, wherein the fluorescent nanoparticles are chromophoric polymer dots each including at least one condensed conjugated polymer. Often, lyophilizing comprises freezing the suspension at a temperature below about −10° C., below about −20° C., below about −30° C., or below about −40° C. In some cases, lyophilizing comprises freezing the suspension at a temperature at or around −80° C. Often, lyophilizing comprises freezing the suspension at a temperature below −10° C., below −20° C., below −30° C., or below −40° C. In some cases, lyophilizing comprises freezing the suspension at a temperature at or around −80° C.

In some cases, the methods described herein may further include, before lyophilizing, combining (i) a liquid comprising fluorescent nanoparticles with (ii) a first aqueous solution, thereby forming the suspension comprising fluorescent nanoparticles. In some cases, the methods described herein may further include combining (i) a liquid comprising a fluorescent nanoparticle with (ii) a first aqueous solution, thereby forming the suspension comprising fluorescent nanoparticles. Often, the aqueous solution comprises a lyophilization agent. In some cases, the suspension comprises a carbohydrate, often the carbohydrate comprises a monosaccharide, a disaccharide, an oligosaccharide, a polysaccharide, or a combination thereof. For example, the carbohydrate is selected from a monosaccharide, a disaccharide, an oligosaccharide, a polysaccharide, or a combination thereof. In some cases, the disaccharide may be selected from the group consisting of sucrose, trehalose dihydrate, maltose monohydrate, and lactose monohydrate.

In some cases, the suspension includes an alditol, hydroxypropyl-cyclodextrin, bovine serum albumin or a combination thereof. Often, the suspension comprises a disaccharide, for example, the disaccharide may be present between about 1% w/v and 50% w/v, or may be present between about 10% w/v and 20% w/v. For example, the disaccharide is sucrose, for example, the sucrose may be present between about 10% w/v and 20% w/v. Often, the suspension comprises a disaccharide, for example, the disaccharide may be present between 1% w/v and 50% w/v, or may be present between 10% w/v and 20% w/v. For example, the disaccharide is sucrose, for example, the sucrose may be present between 10% w/v and 20% w/v.

In some cases, the methods described herein may further comprise mixing the lyophilized composition with a second aqueous solution, thereby forming a second suspension comprising the fluorescent nanoparticles dispersed in the second aqueous solution. Often, the dispersed fluorescent nanoparticles in the second aqueous solution have a similar or increased quantum yield as compared to unlyophilized fluorescent nanoparticles. Often, the dispersed fluorescent nanoparticles in the second aqueous solution have a similar particle diameter as compared to the particle diameter unlyophilized fluorescent nanoparticles. In some cases, the compositions described herein may comprise fluorescent nanoparticles that may comprise similar or increased quantum yield when dispersed in an aqueous solution as compared to the fluorescent nanoparticles prior to lyophilization. In some cases, the quantum yield of lyophilized chromophoric polymer dots can be similar to unlyophilized chromophoric polymer dots. For example, the quantum yield of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the quantum yield of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. Often, the fluorescent nanoparticles comprise a similar particle diameter when dispersed in an aqueous solution as compared to the particle diameter of fluorescent nanoparticles prior to lyophilization. In some cases, the particle diameter of lyophilized chromophoric polymer dots can be similar to unlyophilized chromophoric polymer dots. For example, the particle diameter of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the particle diameter of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. In some cases, the dispersed fluorescent nanoparticles have an average diameter of less than about 30 nm as measured by dynamic light scattering.

The methods described herein may further comprise at least one condensed conjugated polymer comprises a semiconducting polymer. Often, the at least one condensed conjugated polymer is selected from the group consisting of a fluorene polymer, a flourene-based polymer, a phenylene vinylene polymer, and a phenylene ethynylene polymer. For example, at least one condensed conjugated polymer is selected from the group consisting of poly(9,9-dihexylfluorenyl-2,7-diyl) (PDHF), Poly(9,9-dioctylfluorenyl-2,7-diyl) (PFO), poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-Di-2-thienyl-2,1,3-benzothiadiazole)] (PF-0.1TBT)), and poly[2-methoxy-5-(2-ethylhexyloxy)-1,4-phenylenevinylene] (MEH-PPV), poly[2-methoxy-5-(2-ethylhexyloxy)-1,4-(1-cyanovinylene-1,4-phenylene)] (CN-PPV), BODIPY 570, BODIPY 590, and BODIPY 690.

In some cases, the quantum yield of the fluorescent particles after dispersion in a solution is higher than the unlyophilized fluorescent particles. Often, the full width half maximum of the emission bandwidth of the fluorescent particles after dispersion in a solution is narrower than the full width half maximum emission bandwidth of the unlyophilized fluorescent particles.

The methods described herein may include a method of producing a lyophilized composition comprising lyophilizing a suspension comprising fluorescent particles, thereby forming the lyophilized composition of fluorescent nanoparticles, wherein the fluorescent nanoparticles are chromophoric polymer dots comprising a polymer.

Often, lyophilizing comprises freezing the suspension at a temperature below about −10° C., below about −20° C., below about −30° C., or below about −40° C. In some cases, lyophilizing comprises freezing the suspension at a temperature at or around −80° C. Often, lyophilizing comprises freezing the suspension at a temperature below −10° C., below −20° C., below −30° C., or below −40° C. In some cases, lyophilizing comprises freezing the suspension at a temperature at or around −80° C.

In some cases, the methods described herein may further include, before lyophilizing, combining (i) a liquid comprising fluorescent nanoparticles with (ii) a first aqueous solution, thereby forming the suspension comprising fluorescent nanoparticles. In some cases, the methods described herein may further include combining (i) a liquid comprising a fluorescent nanoparticle with (ii) a first aqueous solution, thereby forming the suspension comprising fluorescent nanoparticles. Often, the aqueous solution comprises a lyophilization agent. In some cases, the suspension comprises a carbohydrate, often the carbohydrate comprises a monosaccharide, a disaccharide, an oligosaccharide, a polysaccharide, or a combination thereof. For example, the carbohydrate is selected from a monosaccharide, a disaccharide, an oligosaccharide, a polysaccharide, or a combination thereof. In some cases, the disaccharide may be selected from the group consisting of sucrose, trehalose dihydrate, maltose monohydrate, and lactose monohydrate.

In some cases, the suspension includes an alditol, hydroxypropyl-cyclodextrin, bovine serum albumin or a combination thereof. Often, the suspension comprises a disaccharide, for example, the disaccharide may be present between about 1% w/v and 50% w/v, or may be present between about 10% w/v and 20% w/v. For example, the disaccharide is sucrose, for example, the sucrose may be present between about 10% w/v and 20% w/v. In some cases, the suspension includes an alditol, hydroxypropyl-cyclodextrin, bovine serum albumin or a combination thereof. Often, the suspension comprises a disaccharide, for example, the disaccharide may be present between 1% w/v and 50% w/v, or may be present between 10% w/v and 20% w/v. For example, the disaccharide is sucrose, for example, the sucrose may be present between 10% w/v and 20% w/v.

In some cases, the methods described herein may further comprise mixing the lyophilized composition with a second aqueous solution, thereby forming a second suspension comprising the fluorescent nanoparticles dispersed in the second aqueous solution. Often, the dispersed fluorescent nanoparticles in the second aqueous solution have a similar or increased quantum yield as compared to unlyophilized fluorescent nanoparticles. Often, the dispersed fluorescent nanoparticles in the second aqueous solution have a similar particle diameter as compared to the particle diameter unlyophilized fluorescent nanoparticles. In some cases, the compositions described herein may comprise fluorescent nanoparticles that may comprise similar or increased quantum yield when dispersed in an aqueous solution as compared to the fluorescent nanoparticles prior to lyophilization. In some cases, the quantum yield of lyophilized chromophoric polymer dots can be similar to unlyophilized chromophoric polymer dots. For example, the quantum yield of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the quantum yield of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. Often, the fluorescent nanoparticles comprise a similar particle diameter when dispersed in an aqueous solution as compared to the particle diameter of fluorescent nanoparticles prior to lyophilization. In some cases, the particle diameter of lyophilized chromophoric polymer dots can be similar to unlyophilized chromophoric polymer dots. For example, the particle diameter of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the particle diameter of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. In some cases, the dispersed fluorescent nanoparticles have an average diameter of less than about 30 nm as measured by dynamic light scattering.

The methods described herein may further comprise at least one condensed conjugated polymer comprises a semiconducting polymer. Often, the at least one condensed conjugated polymer is selected from the group consisting of a fluorene polymer, a flourene-based polymer, a phenylene vinylene polymer, and a phenylene ethynylene polymer. For example, at least one condensed conjugated polymer is selected from the group consisting of poly(9,9-dihexylfluorenyl-2,7-diyl) (PDHF), Poly(9,9-dioctylfluorenyl-2,7-diyl) (PFO), poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4- benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-Di-2-thienyl-2,1,3-benzothiadiazole)] (PF-0.1TBT)), and poly[2-methoxy-5-(2-ethylhexyloxy)-1,4-phenylenevinylene] (MEH-PPV), poly[2-methoxy-5-(2-ethylhexyloxy)-1,4-(1-cyanovinylene-1,4-phenylene)] (CN-PPV), BODIPY 570, BODIPY 590, and BODIPY 690.

In some cases, the method may include the quantum yield of the fluorescent particles after dispersion in a solution is higher than the unlyophilized fluorescent particles. Often, the full width half maximum of the emission bandwidth of the fluorescent particles after dispersion in a solution is narrower than the full width half maximum emission bandwidth of the unlyophilized fluorescent particles.

The methods described herein may further include a method for dispersing a lyophilized of nanoparticle comprising combining a lyophilized composition comprising a fluorescent nanoparticle with an aqueous solution; and agitating the combination above to produce a dispersed sample of fluorescent nanoparticle. Often, the polymer comprises a semiconducting polymer. In some cases, the polymer is selected from the group consisting of a fluorene polymer, a flourene-based polymer, a phenylene vinylene polymer, and a phenylene ethynylene polymer. For example, the polymer is selected from the group consisting of poly(9,9-dihexyl-fluorenyl-2,7-diyl) (PDHF), Poly(9,9-dioctylfluorenyl-2,7-diyl) (PFO), poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-Di-2-thienyl-2,1,3-benzothiadiazole)] (PF-0.1TBT)), and poly[2-methoxy-5-(2-ethylhexyloxy)-1,4-phenylenevinylene] (MEH-PPV), poly[2-methoxy-5-(2-ethylhexyloxy)-1,4-(1-cyanovinylene-1,4-phenylene)] (CN-PPV), BODIPY 570, BODIPY 590, and BODIPY 690.

In some cases, the methods may include a polymer that may comprise a BODIPY derivative. Often, the BODIPY derivative may have the structure of Formula (I):

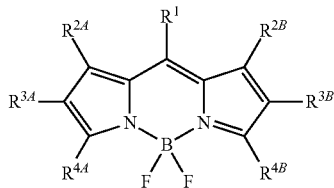

(I)

wherein each of $R^1$, $R^{2A}$, $R^{2B}$, $R^{3A}$, $R^{4A}$ and $R^{4B}$ is independently selected from hydrogen, alkyl, aralkyl, aryl, and alkoxy-aryl, and wherein the BODIPY derivative is integrated into the chromophoric polymer by attachment to $R^1$, $R^{2A}$, $R^{2B}$, $R^{3A}$, $R^{4A}$ and $R^{4B}$, or a combination thereof.

In some cases, the at least one condensed conjugated polymer is conjugated to a biomolecule. Often, the biomolecule comprises a protein, an antibody, a nucleic acid molecule, a lipid, a peptide, an aptamer, a drug, or a combination thereof. For example, the biomolecule may comprise streptavidin. For another example, the biomolecule may comprise an aptamer. For another example, the biomolecule may comprise a nucleic acid. For another example, the biomolecule may comprise an antibody.

In some cases, the methods may further comprise fluorescent nanoparticles that may have an average diameter of between 30 nm and 100 nm as measured by dynamic light scattering. For example, the fluorescent nanoparticles have an average diameter of less than about 100 nm as measured by dynamic light scattering.

Storage of Lyophilized Polymer Dots and Dispersion of Lyophilized Polymer Dots

The methods, kits and compositions of lyophilized chromophoric polymer dots described herein include the ability to store the chromophoric polymer dots for long periods of time. After the storage of the chromophoric polymer dots over long periods of time as lyophilized chromophoric polymer dot compositions, the chromophoric polymer dots can be redispersed in solution and used for a variety of purposes. In some cases, the chromophoric polymer dots, e.g., can be redispersed without aggregation, thereby having a similar size (e.g., particle diameter) characteristics of the chromophoric polymer dots prior to lyophilization. In some cases, the compositions described herein may comprise fluorescent nanoparticles that may comprise similar or increased quantum yield when dispersed in an aqueous solution as compared to the fluorescent nanoparticles prior to lyophilization. In some cases, the quantum yield of lyophilized chromophoric polymer dots can be similar to unlyophilized chromophoric polymer dots. For example, the particle diameter of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the particle diameter of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots.

In some cases, storage periods can include, but are not limited to, longer than one day, longer than one week, longer than one month, longer than two months, longer than three months, longer than six months, or longer than one year. In some cases, the storage period can range from about one day to about one year, from about one day to about six months, from about one day to about three months, from about one day to about two months, or from about one day to about one month.

The lyophilized compositions, kits and methods can provide several useful results for chromophoric polymer dots. For example, by using flow cytometry, lyophilized chromophoric polymer dot bioconjugates retained their biological targeting properties and were able to effectively label cells. In one example, cells labeled with lyophilized chromophoric polymer dot bioconjugates composed of PFBT, which were stored for 6 months at −80° C., were ~22% brighter than those labeled with identical but unlyophilized chromophoric polymer dot bioconjugates. These results among others indicate lyophilization can be a useful approach for storing and shipping chromophoric polymer dot bioconjugates, which is an important practical consideration for ensuring chromophoric polymer dots are widely adopted in biomedical research.

The lyophilized compositions, kits and methods can provide several useful results for maintaining the colloidal stability of the lyophilized compositions of chromophoric polymer dots compared to unlyophilized chromophoric polymer dots.

Properties of Lyophilized Polymer Dots

Chromophoric polymer dots are fluorescent polymer-based particles and can contain a hydrophobic core and thus potentially may aggregate if water is driven from the core of the chromophoric polymer dots. A polymer of the disclosure can aggregate with a suitable hydrophobic compound, thereby forming a complex in water held together by favorable hydrophobic interactions. Non-limiting examples of hydrophobic groups that can interact with a polymer of the disclosure include polystyrenes, polyaryls, polyolefins, peptides, hydrocarbons, and halogenated hydrocarbons, such as fluorocarbons.

A hydrophobic group can be connected to another group. The aggregation of the polymer and the hydrophobic compound thus attaches the connected other group to the chromophoric polymer dot. The other group can be a hydrophilic group, for example, polyethylene glycol, a carboxylic acid or a salt thereof. Non-limiting examples of compounds have a hydrophobic part that aggregates with a chromophoric polymer dot, connected to a hydrophilic group include polystyrene polyethylene glycol carboxylic acid, or a salt thereof (PSPEGCOOH), polystyrene maelic anhydride (PSMA), and polystyrene polyethylene glycol (PSPEG).

Organic conjugated polymers and oligomers can be metallic upon heavy doping, a term derived from inorganic semiconductor chemistry. The doping in a conjugated polymer can include an oxidation or a reduction of the π-electronic system and is called p-doping and n-doping, respectively.

The chromophoric polymer dots provided herein may be formed by any method known in the art for collapsing polymers, including without limitation, methods relying on precipitation, methods relying on the formation of emulsions (e.g., mini or micro emulsion), and methods relying on condensation. In some cases, the chromophoric polymer dots described herein can be formed by nanoprecipitation.

The lyophilized compositions and methods described herein can improve the photophysical properties of the chromophoric polymer dots through the process of lyophilization. For example, chromophoric polymer dots can contain a hydrophobic core and thus the chain conformation may change if water is driven from the system. In the case of using lyoprotectants during lyophilization, lyoprotectant molecules can form a surface layer, and diffuse into the chromophoric polymer dot shell as water is driven out, therefore reducing polymer chain-chain interactions. As a result, the photophysical properties of the chromophoric polymer dots can be improved after lyophilization and reconstitution into a solution after storage.

The present disclosure includes a lyophilized composition including fluorescent nanoparticles, the fluorescent nanoparticles comprising at least one condensed conjugated polymer. The various conjugated polymers (e.g., semiconducting polymers) are described further herein. In some cases, the fluorescent nanoparticles may have optical properties. In some cases, fluorescence quantum yield can be increased. In some cases, the fluorescence emission bandwidth can be reduced. In some cases, the cell labeling brightness can be increased.

In certain cases, when the chromophoric polymer dots in the lyophilized compositions are reconstituted, the optical properties are similar or improved in comparison to the chromophoric polymer dots in the solution prior to lyophilization. For example, the optical properties of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the optical properties of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots.

For example, after lyophilization in combination with a disaccharide, the chromophoric polymer dots can unexpectedly exhibit a similar or increased quantum yield.

Quantum Yield.

In some cases, the fluorescence quantum yield of chromophoric polymer dots is improved by the process of lyophilization. The quantum yield, for example, can be the ratio of photons emitted relative to the photons absorbed by a molecule. Often the percentage of the quantum yield can be measured by the fraction that relaxes by emitting photon over the total number that relaxes to the ground state. In some cases, when a chromophoric polymer dot is excited to an excited state, it can relax down to the ground state by emitting a photon or not. Often, the composition may comprise a lyophilized chromophoric polymer dot wherein the lyophilized chromophoric polymer dot has a quantum yield that is greater than a quantum yield of an analogous chromophoric polymer dot that was never lyophilized. For example, the quantum yield of the chromophoric polymer dot that was lyophilized is greater than one-fold higher than a quantum yield of an analogous chromophoric polymer dot that was never lyophilized.

In some cases, the quantum yield of lyophilized chromophoric polymer dots can be similar to unlyophilized chromophoric polymer dots. For example, the quantum yield of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the quantum yield of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. For example, greater than the quantum yield of lyophilized chromophoric polymer dots can be 80%, greater than 85%, greater than 90%, greater than 91%, greater than 92%, greater than 93%, greater than 94%, greater than 95%, greater than 96%, greater than 97%, greater than 98%, greater than 99% or 100% similar to unlyophilized chromophoric polymer dots. For example, greater than about the quantum yield of lyophilized chromophoric polymer dots can be 80%, greater than about 85%, greater than about 90%, greater than about 91%, greater than about 92%, greater than about 93%, greater than about 94%, greater than about 95%, greater than about 96%, greater than about 97%, greater than about 98%, greater than about 99% or greater than about 100% similar to unlyophilized chromophoric polymer dots.

In some cases, the lyophilized chromophoric polymer dots have a fluorescence quantum yield that equal to or is higher than that of the unlyophilized chromophoric polymer dots. In some cases, the lyophilized chromophoric polymer dots have a fluorescence quantum yield that is 1.5 times higher than that of the unlyophilized chromophoric polymer dots. In some cases, the lyophilized chromophoric polymer dots have a fluorescence quantum yield that is 2 times higher than that of the unlyophilized chromophoric polymer dots. In some cases, the lyophilized chromophoric polymer dots have a fluorescence quantum yield that is 2.5 times higher than that of the unlyophilized chromophoric polymer dots. In some cases, the lyophilized chromophoric polymer dots have a fluorescence quantum yield that is 3 times higher than that of the unlyophilized chromophoric polymer dots. In some cases, the lyophilized chromophoric polymer dots have a fluorescence quantum yield that is 3.5 times higher than that of the unlyophilized chromophoric polymer dots. In some cases, the lyophilized chromophoric polymer dots have a fluorescence quantum yield that is 4 times higher than that of the unlyophilized chromophoric polymer dots. In some cases, the lyophilized chromophoric polymer dots have a fluorescence quantum yield that is 4.5 times higher than that of the unlyophilized chromophoric polymer dots. In some cases, the lyophilized chromophoric polymer dots have a fluorescence quantum yield that is 5 times higher than that of the unlyophilized chromophoric polymer dots. In some cases, the lyophilized chromophoric polymer dots have a fluorescence quantum yield that is more than 5 times higher than that of the unlyophilized chromophoric polymer dots.

In some cases, chromophoric polymer dots may be lyophilized. In some cases, lyophilized chromophoric polymer dots may have a quantum yield greater than or equal to about 40%, 30%, 20%, 10%, or 1% of the quantum yield of unlyophilized chromophoric polymer dots. In some cases, the quantum yield of the lyophilized chromophoric polymer dot may be greater than 30%, 20%, 10%, or 1% of the quantum yield of unlyophilized chromophoric polymer dots. In some cases, the lyophilized chromophoric polymer dot may have a quantum yield within the following ranges, 1-10%, 5-15%, 10-20%, 15-25%, 20-30% or greater than 30% of the quantum yield of unlyophilized chromophoric polymer dots.

Absorption Wavelength.

Lyophilized chromophoric polymer dots may have a wide range of absorption wavelengths compared to unlyophilized chromophoric polymer dots. In some cases, lyophilized chromophoric polymer dots may have an absorption wavelength less than or equal to about 1000 nm, about 900 nm, about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, lyophilized chromophoric polymer dots may have an absorption wavelength less than or equal to 1000 nm, 900 nm, 800 nm, 750 nm, 700 nm, 650 nm, 600 nm, 550 nm, 500 nm, 450 nm, 400 nm, 350 nm, 300 nm, 250 nm, 200 nm, 150 nm, or 100 nm. In some cases, the lyophilized chromophoric polymer dot may have an absorption wavelength within the following ranges, 100-300 nm, 200-400 nm, 300 nm-500 nm, 400 nm-600 nm, 500-700 nm-600 nm-800 nm or 800 nm-1000 nm. In some cases, about the lyophilized chromophoric polymer dot may have an absorption wavelength within the following ranges, about 100-300 nm, about 200-400 nm, about 300 nm-500 nm, about 400 nm-600 nm, about 500-700 nm-600 nm-800 nm or 800 nm-1000 nm. In some cases, the absorption wavelength of the lyophilized chromophoric polymer dot may be 405 nm, 450 nm, 488, 532 nm, 633 nm or 700 nm.

In some cases, the absorption wavelength of lyophilized chromophoric polymer dots can be similar to unlyophilized chromophoric polymer dots. For example, the absorption wavelength of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the absorption wavelength of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. For example, greater than the absorption wavelength of lyophilized chromophoric polymer dots can be greater than 80%, greater than 85%, greater than 90%, greater than 91%, greater than 92%, greater than 93%, greater than 94%, greater than 95%, greater than 96%, greater than 97%, greater than 98%, greater than 99% or 100% similar to unlyophilized chromophoric polymer dots. For example, greater than about the absorption wavelength of lyophilized chromophoric polymer dots can be greater than about 80%, greater than about 85%, greater than about 90%, greater than about 91%, greater than about 92%, greater than about 93%, greater than about 94%, greater than about 95%, greater than about 96%, greater than about 97%, greater than about 98%, greater than about 99% or 100% similar to unlyophilized chromophoric polymer dots.

Photoluminescence Wavelength.

Lyophilized chromophoric polymer dots may have a wide range of photoluminescence wavelengths compared to unlyophilized chromophoric polymer dots. In some cases, lyophilized chromophoric polymer dots may have a photoluminescence less than or equal to about 1000 nm, about 900 nm, about 800 nm, about 750 nm, about 700 nm, about 650 nm, about 600 nm, about 550 nm, about 500 nm, 450 nm, about 400 nm, about 350 nm, about 300 nm, about 250 nm, about 200 nm, about 150 nm, or about 100 nm. In some cases, lyophilized chromophoric polymer dots may have a photoluminescence less than or equal to 1000 nm, 900 nm, 800 nm, 750 nm, 700 nm, 650 nm, 600 nm, 550 nm, 500 nm, 450 nm, 400 nm, 350 nm, 300 nm, 250 nm, 200 nm, 150 nm, or 100 nm. In some cases, the lyophilized chromophoric polymer dot may have a photoluminescence within the following ranges, 100-300 nm, 200-400 nm, 300 nm-500 nm, 400 nm-600 nm, 500-700 nm, 600 nm-800 nm or 800 nm-1000 nm. In some cases, about the lyophilized chromophoric polymer dot may have a photoluminescence within the following ranges, about 100-300 nm, about 200-400 nm, about 300 nm-500 nm, about 400 nm-600 nm, about 500-700 nm, about 600 nm-800 nm or 800 nm-1000 nm. In some cases, the photoluminescence of the lyophilized chromophoric polymer dot may be 405 nm, 450 nm, 488, 532 nm, 633 nm or 700 nm.

In some cases, the photoluminesence wavelength of lyophilized chromophoric polymer dots can be similar to unlyophilized chromophoric polymer dots. For example, the photoluminesence wavelength of lyophilized chromophoric polymer dots can be 80%, 85%, 90%, 91%, 92%, 93%, 94%, 95%, 96%, 97%, 98%, 99% or 100% similar to unlyophilized chromophoric polymer dots. For example, about the photoluminesence wavelength of lyophilized chromophoric polymer dots can be about 80%, about 85%, about 90%, about 91%, about 92%, about 93%, about 94%, about 95%, about 96%, about 97%, about 98%, about 99% or about 100% similar to unlyophilized chromophoric polymer dots. For example, greater than the photoluminesence wavelength of lyophilized chromophoric polymer dots can be greater than 80%, greater than 85%, greater than 90%, greater than 91%, greater than 92%, greater than 93%, greater than 94%, greater than 95%, greater than 96%, greater than 97%, greater than 98%, greater than 99% or 100% similar to unlyophilized chromophoric polymer dots. For example, greater than about the photoluminesence wavelength of lyophilized chromophoric polymer dots can be greater than about 80%, greater than about 85%, greater than about 90%, greater than about 91%, greater than about 92%, greater than about 93%, greater than about 94%, greater than about 95%, greater than about 96%, greater than about 97%, greater than about 98%, greater than about 99% or 100% similar to unlyophilized chromophoric polymer dots.

Applications

Chromophoric polymer dots are useful for many detection and/or imaging applications. The detection and/or imaging applications may include single-cell labeling, multi-cell labeling, tissue labeling, organ labeling, in vitro labeling, and in vivo labeling. The detection and/or imaging of cells may include molecules expressed by the cells, such as, extracellular molecules or intracellular molecules. The detection and/or imaging may include molecules attached to the cells such as proteins, sugars, particulates.

Cases of the present disclosure relate to the fluorinated chromophoric polymer dots and their biomolecular conjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cellular imaging, in vivo imaging, bioorthogonal labeling, click reactions, fluorescence-based biological assays such as immunoassays and enzyme-based assays (e.g., ELISA), western blot, and a variety of fluorescence techniques in biological assays and measurements.

The chromophoric polymer dots described herein can be used in a wide variety of applications including, medical diagnostics, medical prognostics, biological research, and water and soil testing. Similarly, the chromophoric polymer dots may be used to detect a wide variety of analytes, such as cells, microbes, bacteria, viruses, proteins, peptides, carbohydrates, nucleic acids or portions thereof.

This disclosure provides methods for using chromophoric polymer dots to label and detect analytes within a sample such as a mixed sample. In some cases, the sample may be a fluid sample. The fluid sample may be a biological fluid sample, for example a blood sample, plasma sample, saliva sample, urine sample, lymph sample, or spinal fluid sample. In some cases, the sample may be an environmental fluid sample, for example from a lake, river, ocean, pond, stream, spring, marsh, or reservoir. In other cases, the sample may be a water sample, for example from a desalinization plant, water treatment plant, reservoir, spring, stream, glacial water flow, water tower, or other water source that may be contemplated as a source of potable water.

In some cases, a molecule expressed by an analyte such as a cell may be detected with the chromophoric polymer dots provided herein. For example, cells may be contacted with an agent (e.g., antibody) that recognizes a molecule (e.g, cell surface marker, intracellular marker, etc.). In some cases provided herein, the agent is modified so that it can bind to or connect to a binding partner that is connected to a chromophoric polymer dot. For example, the agent may be modified by conjugating the agent to biotin or streptavidin. In some specific examples, the agent is conjugated to biotin so that the agent is capable of recognizing a streptavidin molecule that is conjugated to a chromophoric polymer dot. Such chromophoric polymer dots are useful in a wide variety of applications, including cellular imaging studies.

The methods provided herein may include incubation periods. For example, the chromophoric polymer dots may be incubated with the agents (such as antibodies); the agents (including agents conjugated to chromophoric polymer dots) may be incubated with the analytes (e.g., cells). The incubation period may last for a length of time that is less than or equal to 100 hours, 75 hours, 60 hours, 50 hours, 24 hours, 20 hours, 15 hours, 10 hours, 5 hours, 3 hours, 2 hours, or 1 hour. In some cases, the incubation period may be greater than 5 minutes, 10 minutes, 30 minutes, 1 hour, 2 hours, 5 hours, 10 hours, 24 hours, 30 hours, 50 hours, 60 hours, 75 hours or 100 hours. In some cases, the incubation period may be 5 minutes, 10 minutes, 30 minutes, 1 hour, 2 hours, 5 hours, 10 hours, 24 hours, 30 hours, 50 hours, 60 hours, 75 hours or 100 hours. In some cases, the incubation period may be about 5 minutes, 10 minutes, 30 minutes, 1 hour, 2 hours, 5 hours, 10 hours, 24 hours, 30 hours; 50 hours, 60 hours, 75 hours or 100 hours.

The analyte in the fluid sample may be a cell, protein, protein complex, nucleic acid, nucleoprotein complex, carbohydrate, metabolite, catabolite, and the like. In some cases, the analyte may be a cell. Non-limiting examples of cells include mammalian cells, human cells, non-human mammalian cells, eukaryotic cells, prokaryotic cells, animal cells, insect cells, bacteria cells, microbial cells, fungal cells, amphibian cells and fish cells. The cells can originate from a variety of tissues including but not limited to: neural crest tissue, endodermal tissue, ectodermal tissue, mesodermal tissue, and mesenchymal tissue. Cell types may include but are not limited to: breast cells, brain cells, neural cells, pancreatic cells, liver cells, gall bladder cells, gastrointestinal cells, stomach cells, kidney cells, cells of the reproductive system, heart cells, skin cells, colon cells, urethral cells, endodermal cells, muscle cells, fibroblasts, adipocytes, tumor cells, cancer cells, virally-infected cells, bacterial infected cells, stem cells, dividing cells, apoptotic cells, necrotic cells, blood cells, white blood cells, and stromal cells.

The sample may be contacted with an agent suitable for labeling the analyte. In some cases, the agent may be an antibody, an antibody fragment, a peptide, a Fab fragment, an Fc fragment, a light chain, a heavy chain, an immunoglobin, or an immunoglobin fragment. In some cases, the agent is a peptide or a small molecule. In some cases, the agent is modified. The modification to the agent may include a chemical modification, an enzymatic modification, linkage of a hydrophilic functional group, a hydrophobic functional group and/or a reactive moiety.

In some cases, the cell may express an antigen, for example, that may be detected by the agent. For example, an agent may be an antibody. The antibody may be EpCAM which is expressed on some cancerous cells, including MCF-7 cells. Other examples of antibodies that may be conjugated to a chromophoric polymer dot include but are not limited to the pan-cytokeratin antibody A45B/B3, AE1/AE3, or CAM5.2 (pan-cytokeratin antibodies that recognize Cytokeratin 8 (CK8), Cytokeratin 18 (CK18), or Cytokeratin 19 (CK19) and ones against: breast cancer antigen NY-BR-1 (also known as B726P, ANKRD30A, Ankyrin repeat domain 30A); B305D isoform A or C (B305D-A ro B305D-C; also known as antigen B305D); Hermes antigen (also known as Antigen CD44, PGP1); E-cadherin (also known as Uvomorulin, Cadherin-1, CDH1); Carcino-embryonic antigen (CEA; also known as CEACAM5 or Carcino-embryonic antigen-related cell adhesion molecule 5); β-Human chorionic gonadotophin (β-HCG; also known as CGB, chronic gonadotrophin, β polypeptide); Cathepsin-D (also known as CTSD); Neuropeptide Y receptor Y3 (also known as NPY3R; Lipopolysaccharide-associated protein3, LAP3, Fusion; chemokine (CXC motif, receptor 4); CXCR4); Oncogene ERBB1 (also known as c-erbB-1, Epidermal growth factor receptor, EGFR); Her-2 Neu (also known as c-erbB-2 or ERBB2); GABA receptor A, pi ($\pi$) polypeptide (also known as GABARAP, GABA-A receptor, pi ($\pi$) polypeptide (GABA A($\pi$), γ-Aminobutyric acid type A receptor pi ($\pi$) subunit), or GABRP); ppGalNac-T(6) (also known as β-1-4-N-acetyl-galactosaminyl-transferase 6, GalNActransferase 6, GalNAcT6, UDP-N-acetyl-d-galactosamine:polypeptide N-acetylgalactosaminyltransferase 6, or GALNT6); CK7 (also known as Cytokeratin 7, Sarcolectin, SCL, Keratin 7, or KRT7); CK8 (also known as Cytokeratin 8, Keratin 8, or KRT8); CK18 (also known as Cytokeratin 18, Keratin 18, or KRT18); CK19 (also known as Cytokeratin 19, Keratin 19, or KRT19); CK20 (also known as Cytokeratin 20, Keratin 20, or KRT20); Mage (also known as Melanoma antigen family A subtytpes or MAGE-A subtypes); Mage3 (also known as Melanoma antigen family A 3, or MAGA3); Hepatocyte growth factor receptor (also known as HGFR, Renal cell carcinoma papillary 2, RCC P2, Protooncogene met, or MET); Mucin-1 (also known as MUC1, Carcinoma Antigen 15.3, (CA15.3), Carcinoma Antigen 27.29 (CA 27.29); CD227 antigen, Episialin, Epithelial Membrane Antigen (EMA), Polymorphic Epithelial Mucin (PEM), Peanut-reactive urinary mucin (PUM), Tumor-associated glycoprotein 12 (TAG12)); Gross Cystic Disease Fluid Protein (also known as GCDFP-15, Prolactin-induced protein, PIP); Urokinase receptor (also known as uPR, CD87 antigen, Plasminogen activator receptor urokinase-type, PLAUR); PTHrP (parathyroid hormone-related proteins; also known as PTHLH); BS106 (also known as B511S, small breast epithelial mucin, or SBEM); Prostatein-like Lipophilin B (LPB, LPHB; also known as Antigen BU101, Secretoglobin family 1-D member 2, SCGB1-D2); Mammaglobin 2 (MGB2; also known as Mammaglobin B, MGBB, Lacryglobin (LGB) Lipophilin C (LPC, LPHC), Secretoglobin family 2A member 1, or SCGB2A1); Mammaglobin (MGB; also known as Mammaglobin 1, MGB1, Mammaglobin A, MGBA, Secretoglobin family 2A member 2, or SCGB2A2); Mammary serine protease inhibitor (Maspin, also known as Serine (or cystein) proteinase inhibitor Glade B (ovalbumin) member 5, or SERPINB5); Prostate epithelium-specific Ets transcription factor (PDEF; also known as Sterile alpha motif pointed domain-containing ets transcription factor, or SPDEF); Tumor-associated calcium signal transducer 1 (also known as Colorectal carcinoma antigen CO17-1A, Epithelial Glycoprotein 2 (EGP2), Epithelial glycoprotein 40 kDa (EGP40), Epithelial Cell Adhesion Molecule (EpCAM), Epithelial-specific antigen (ESA), Gastrointestinal tumor-associated antigen 733-2 (GA733-2), KS1/4 antigen, Membrane component of chromosome 4 surface marker 1 (M4S1), MK-1 antigen, MIC18 antigen, TROP-1 antigen, or TACSTD1); Telomerase reverse transcriptase (also known as Telomerase catalytic subunit, or TERT); Trefoil Factor 1 (also known as Breast Cancer Estrogen-Inducible Sequence, BCEI, Gastrointestinal Trefoil Protein, GTF, pS2 protein, or TFF1); folate; or Trefoil Factor 3 (also known as Intestinal Trefoil Factor, ITF, p1.B; or TFF3).

In some cases, a sample containing analytes may be prepared for labeling. At any stage of a method provided herein, the analytes (e.g., cells) may be incubated with a blocking buffer to prevent or reduce non-specific binding of the agent. In some cases, non-specific binding may be measured, e.g., by percentage, fold, change, of non-specific binding, relative to another compound. For example, the fold of non-specific binding may be less than 1 fold, 2 fold, 3 fold, 4 fold, 5 fold, 6 fold, 7 fold, 8 fold, 9 fold or 10 fold. For example, the fold of non-specific binding may be 1 fold, 2 fold, 3 fold, 4 fold, 5 fold, 6 fold, 7 fold, 8 fold, 9 fold or 10 fold. For example, the fold of non-specific binding may be about 1 fold, 2 fold, 3 fold, 4 fold, 5 fold, 6 fold, 7 fold, 8 fold, 9 fold or 10 fold.

At any stage of a method provided herein, the analytes (e.g., cells) may be washed with a suitable buffer solution. The cells may be concentrated by any method known in the art, including but not limited to centrifugation or filtration. In some cases, the analytes (e.g., cells) are not concentrated as part of a method provided herein. In some cases, the method may include fixing the cells with a fixative. In other cases, the method may not include fixing the cells with a fixative. In some cases, the method may include permeablizing the cells with an agent suitable for permeabilization. In other cases, preparation of the cells may not include permeablizing the cells with an agent suitable for permeabilization.

The present disclosure provides the use of chromophoric polymer dots for the detection of proteins and peptides. In some cases, the present disclosure relates to the use of bioconjugated chromophoric polymer dots for use in Western blotting assays, including separation and detection of the proteins or peptides of interest. According to various cases of the present disclosure, the proteins or peptides can be separated by chromatography, filtration, capillary electrophoresis, precipitation, liquid or other extraction methods, immunoprecipitation, or a combination thereof. In certain cases, other protein detection assays can be performed using chromophoric polymer dots, including, but not limited to, immunostaining, spectrophotometry, enzyme-based assays (e.g., ELISA), and combinations thereof.

The present disclosure can be used in association with any assay that includes the detection of a protein or peptide analyte using chromophoric polymer dots. In various cases, the protein or peptide can be separated from a mixture before detection. The present methods can be used with an immunological method (e.g., an ELISA assay, an RIA assay, an ELI-Spot assay, a flow cytometry assay, an immunohistochemistry assay, a immunostaining, a Western blot analysis, and a protein chip assay), a physical method (e.g., one- or two-dimensional gel electrophoresis assays, a capillary electrophoresis assay, a FRET assay, a chromatographic assay, or a dye-detection assay, a spectrophotometry assay, a precipitation method), or a combination thereof.

In various cases, prior to detection using chromophoric polymer dots of the present disclosure, proteins or peptides can be separated by a chromatography method, a filtration method, a capillary electrophoresis method, a gel electrophoresis method, a liquid extraction method, a precipitation method, or an immunoprecipitation method. Further, the chromatography method can be reverse phase chromatography. In various cases, a plurality of assays can be performed in parallel to improve analysis throughput.

In various cases, the present disclosure provides methods for detecting proteins or peptides, the method comprising: separating the proteins or peptides from a mixture; contacting the separated proteins or peptides with a solution comprising a polymer dot conjugated to a biomolecule specific to at least some of the separated proteins or peptides; and detecting at least one signal from the polymer dots, the at least one signal corresponding to the separated proteins or peptides. In some cases, the present methods quantitate proteins or peptides.

In some cases, the separating the proteins or peptides comprises a chromatography method, a filtration method, a capillary electrophoresis method, a gel electrophoresis method, a liquid extraction method, a precipitation method, an immunoprecipitation method, or a combination thereof.

In some cases, the polymer dot comprises a polymer selected from a semiconducting polymer, a non-semiconducting polymer, or a combination thereof.

In some cases, the polymer dot comprises a polymer selected from a poly((meth)acrylic acid)-based polymer, a polydiene-based polymer, a poly(ethylene oxide)-based polymer, a polyisobutylene-based polymer, a polystyrene-based polymer, a polysiloxane-based polymer, a poly(ferrocenyldimethylsilane)-based polymer, a poly(2-vinyl naphthalene)-based polymer, a poly(vinyl pyridine)-based polymer, a poly(N-methyl vinyl pyridinium iodide)-based polymer, or a poly(vinyl pyrrolidone)-based polymer.

In some cases, the present disclosure provides for detection of proteins or peptides in conjunction with a Western blot assay. Western blotting is a protein analysis method in which proteins are separated by mass and/or length, typically using sodium dodecyl sulfate-polyacrylamide gel electrophoresis (SDS-PAGE), then transferred onto a membrane composed of, e.g., nitrocellulose or a fluoropolymer such as polyvinylidene fluoride (PVDF), and visualized using a labelling procedure. In the present disclosure, chromophoric polymer dots are shown to provide detection of protein at quantities as low as 50 picograms using Western blot analysis (see e.g., Example 5).

In some cases, the present disclosure enables ultrasensitive fluorescence imaging of proteins on Western blots using polymer dots. In certain cases, the bright, compact, and orange-emitting semiconducting polymer dot, CN-PPV, is used.

In certain cases, proteins or peptides are separated using gel electrophoresis. In further cases of the present disclosure, proteins and peptides are separated using capillary electrophoresis in which proteins or peptides are separated and labelled within the capillary. The method is similar to that performed in a standard SDS-PAGE separation, however, occurs within the capillary space.

During gel electrophoresis, proteins separate across the gel according to size. A size-range, or "band", can then be transferred from within the gel onto a membrane. In some cases, proteins or peptides are transferred to a membrane using an electric current to pull proteins from the gel onto the membrane, in a technique known in the art as electroblotting. In other cases, capillary forces may be used to move proteins from the gel onto a membrane. In other cases of the disclosure, other methods of transferring proteins from a gel to a membrane can be used.

In some cases, the proteins are disposed on a nitrocellulose membrane. In other cases, the proteins are disposed on a membrane composed of a fluoropolymer, e.g., PVDF. Any suitable membrane can be used according to the present disclosure.

In other cases, methods are provided for ultrasensitive fluorescence imaging of molecules using chromophoric polymer dots in a dot blot assay. In a dot blot assay, the proteins or peptides to be detected are not first separated. Instead, an un-separated sample is applied directly on a membrane as a dot and visualized using a labelling procedure. In the present disclosure, chromophoric polymer dots are shown to provide detection of protein at quantities lower than two picograms using dot blot analysis.

A detection limit at the single-picogram level has been observed with conventional Western blotting. Detection at the 50-picograms level has been observed for transferrin and trypsin inhibitor after SDS-PAGE and transfer onto a PVDF membrane. Among many advantages, the present disclosure includes methods that do not require any additional equipment or time compared to the conventional procedure with traditional fluorescent probes.

In some cases of the disclosure, analysis is performed on samples contained within one or more biological cells, tissues, fluids, or other samples. In other cases, the analysis can be performed on a sample after it has been collected from one or more biological cells, tissues, fluids or other samples. The protein or peptide can optionally be separated by methods such as, e.g., SDS-PAGE, after which the protein or peptide can be detected with a bioconjugated chromophoric polymer dot that is specific for the protein or peptide of interest.

Proteins or peptides can be collected from a tissue, cell, or fluid sample by methods can include, but are not limited to, freezing and thawing, sonication, homogenization by high pressure, filtration, permeabilization, and centrifugation. In some cases, an collected protein or peptide can also undergo one or more isolation or purification steps prior to analysis.

In some cases, analysis can be performed on a sample that contains a heterogeneous mix of different proteins. In other cases, analysis can be performed on a purified protein.

In some cases, a sample is separated prior to analysis, such as by gel electrophoresis or another method suitable for separating a sample. In some cases, proteins or peptides are separated based on their mass and/or charge prior to analysis.

In some cases, chromophoric polymer dots are suspended in a liquid, and this liquid is brought into physical contact with a sample, the sample being either suspended in a second liquid or disposed on a surface. In some cases, the sample is disposed on a surface which comprises a membrane.

In some cases, chromophoric polymer dots are disposed on a surface, and this surface is brought into physical contact with a sample, the sample being suspended in a liquid. In some cases, the surface on which chromophoric polymer dots are disposed comprises a membrane.

In some cases, an immunoprecipitation assay is performed, in which chromophoric polymer dots are disposed on a surface and brought into physical contact with a protein sample suspended in a liquid. According to this case, contact between the protein sample and the corresponding chromophoric polymer dot causes the protein to adhere to the surface via the binding chromophoric polymer dot.

In various cases, the presently described chromophoric polymer dots will emit fluorescence when properly induced by an excitation source. In certain cases, the quantity of chromophoric polymer dots present can be determined and subsequently correlated with the quantity of a given analyte of interest, such as e.g., a protein of interest. Thus, the presently described methods utilize an excitation light source to induce chromophoric polymer dot fluorescence, which can then be measured and correlated with sample concentration. In various cases, electromagnetic radiation (e.g., infrared radiation, visible light, or ultraviolet radiation) is used to trigger electromagnetic emission from chromophoric polymer dots, and the emitted signal can be used to assess the amount of target molecule present in a sample. In some cases, the source of electromagnetic radiation can comprise a laser, LED, lamp, spectral filter or multichroic mirror. In some cases, the light excitation source can be a component of a gel imaging apparatus, a microscope, or other suitable apparatus. The chemical and physical properties of a given chromophoric polymer dot can be adjusted in order to tune the excitation and emission wavelengths, among other optical properties.

In some cases, the peak wavelength of electromagnetic radiation that induces excitation of a chromophoric polymer dot is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some cases more than one excitation spectrum may be experienced by a sample, such as in multiplex analyses.

In some cases, the peak wavelength of electromagnetic radiation that induces excitation of a chromophoric polymer dot is between 200 nm and 300 nm, 250 nm and 350 nm, 300 nm and 400 nm, 350 nm and 450 nm, between 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, or 900 nm and 1000 nm. In some cases more than one excitation spectrum may be experienced by a sample, such as in multiplex analyses.

In some cases, the peak wavelength of the detected signal is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, about 900 nm and about 1000 nm, about 950 nm and about 1050 nm, about 1000 nm and about 1100 nm, about 1050 nm and about 1150 nm, about 1100 nm and about 1200 nm, about 1150 nm and about 1250 nm, or about 1200 nm and about 1300 nm.

In some cases, the peak wavelength of the detected signal is between 200 nm and 300 nm, 250 nm and 350 nm, 300 nm and 400 nm, 350 nm and 450 nm, between 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, 900 nm and 1000 nm, 950 nm and 1050 nm, 1000 nm and 1100 nm, 1050 nm and 1150 nm, 1100 nm and 1200 nm, 1150 nm and 1250 nm, or 1200 nm and 1300 nm.

In some cases, the assay is sensitive enough to detect less than 500 picograms, less than 400 picograms, less than 300 picograms, less than 200 picograms, less than 100 picograms, less than 50 picograms, less than 40 picograms, less than 30 picograms, less than 20 picograms, less than 10 picograms, less than five picograms, less than four picograms, less than three picograms, less than two picograms, or less than one picogram of a target molecule, such as a protein.

In some cases, the assay is sensitive enough to detect about 500 picograms, about 400 picograms, about 300 picograms, about 200 picograms, about 100 picograms, about 50 picograms, about 40 picograms, about 30 picograms, about 20 picograms, about 10 picograms, about five picograms, about four picograms, about three picograms, about two picograms, or about one picogram of a target molecule, such as a protein.

In some cases, the assay is sensitive enough to detect 500 picograms, 400 picograms, 300 picograms, 200 picograms, 100 picograms, 50 picograms, 40 picograms, 30 picograms, 20 picograms, 10 picograms, five picograms, four picograms, three picograms, two picograms, or one picogram of a target molecule, such as a protein.

Among many advantages, such as improved detection sensitivity and photo-stability, the present disclosure includes methods that do not require any additional equipment or time compared to the conventional procedure with traditional fluorescent probes.

As used herein, "specificity" refers to a conjugated chromophoric polymer dot having greater binding affinity for its target than it has for other components it is in physical contact with. A conjugated chromophoric polymer dot is specific for its target if the equilibrium constant for the conjugated chromophoric polymer dot and its target is greater than the average of the equilibrium constants for the conjugated chromophoric polymer dot and the other components it is in physical contact with. Greater specificity indicates a greater binding affinity for the target relative to other components, and this yields improvements in detection sensitivity in assays for a target. Advantageously, the present methods exhibit very high specificity for the target molecules of the present disclosure, such as, e.g., proteins or peptides.

In some cases, the use of conjugated chromophoric polymer dots improves detection sensitivity because of the relatively low levels of non-specific adsorption to surfaces by those chromophoric polymer dots, e.g., to membranes on which a sample is disposed. In certain cases, non-specific adsorption is minimized by using a blocking agent, which is any agent that blocks non-specific binding that is capable of interfering with the accurate detection of target proteins or peptides with chromophoric polymer dots. For example, blocking agents advantageously block non-specific adsorption of chromophoric polymer dots and/or biomolecules onto surfaces that the chromophoric polymer dots and/or biomolecules can come into physical contact with.

In certain cases, the detecting comprises detecting picogram quantities of the separated proteins. In further cases, the detecting comprises detecting less than two picograms of the separated proteins. In certain cases, the method further comprises exciting the polymer dot with a source of electromagnetic radiation. In some cases, the source of electromagnetic radiation comprises a laser, a lamp, an LED, or a combination thereof. In further cases, the electromagnetic radiation passes through a spectral filter, a multichroic mirror, or a combination thereof, before exciting the polymer dot.

In some cases, the peak wavelength of electromagnetic radiation exciting the sample is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some cases, two or more peak wavelengths of electromagnetic radiation excite the sample.

In some cases, the peak wavelength of electromagnetic radiation exciting the sample is between 200 nm and 300 nm, 250 nm and 350 nm, 300 nm and 400 nm, 350 nm and 450 nm, between 400 nm and 500 nm, 450 nm and 550 nm, 500 nm and 600 nm, 550 nm and 650 nm, 600 nm and 700 nm, 650 nm and 750 nm, 700 nm and 800 nm, 750 nm and 850 nm, 800 nm and 900 nm, 850 nm and 950 nm, or 900 nm and 1000 nm.

The disclosure provides for methods that may be used to detect analytes in a sample, particularly to detect a chromophoric polymer dot provided herein. The analytes may be labeled with chromophoric polymer dots; or, in some cases, the analytes may be labeled with a combination of chromophoric polymer dots and other labeling agents such as fluorophores. In some cases, labeled analytes from a sample may be analyzed for the presence of a chromophoric polymer dot. In some cases, a flow cytometer may be used to detect chromophoric polymer dots (e.g., FACS Canto II). In some cases, the flow cytometer may be equipped with a laser (e.g., 405 nm). In some cases, the chromophoric polymer dots may be detected using a laser (e.g., 405 nm) and detection channels for fluorescence emission with filters (e.g., 502 nm long-pass and a 510/50 nm band-pass filter). In some cases, the scattered light and fluorescence emission may be detected by photomultiplier tube arrays. In some cases, the data acquired from flow cytometry experiments may be analyzed using software (e.g., FlowJo).

In some cases, fluorescence microscopy may be used to detect the chromophoric polymer dots. For example, a fluorescent microscope equipped with a camera may be used to image cells. The microscope may be a confocal microscope (e.g., Zeiss LSM 510). The chromophoric polymer dots may be excited by laser (e.g., a 405-nm diode laser or a 488-nm argon laser). In some cases, cells may be imaged such as by using glass-bottomed culture dishes.

Compositions and Kits for Using Lyophilized Polymer Dots

In another case, the present disclosure provides kits including the lyophilized chromophoric polymer dot compositions. A typical kit of the disclosure includes a unit dosage form of a lyophilized chromophoric polymer dot composition of the present disclosure, e.g., in a sealed container. In one case, the kit further comprises a sealed container of a suitable vehicle in which the chromophoric polymer dot composition can be dissolved to form a particulate-free sterile solution that is suitable for administration or use.

In some cases of the present disclosure, kits are provided for analysis using polymer dots. In various cases, each of the compositions provided herein can also be configured for use in a kit. In some cases, the composition or kit comprises chromophoric polymer dots conjugated to biomolecules for performing an assay. In some cases, the kit provides an end user with methods and reagents for performing more sensitive assays using conventional lab equipment and procedures. Often, the kit may optionally comprise substances for use as standard and/or controls.

In various cases, the present disclosure provides kits for determining the absolute concentration or the relative concentration, or determining the presence or absence of a target protein or peptide. In some cases, the present kits can be used to analyze samples from a subject. In some cases, the kit can be used in conjunction with a separation method, such as e.g., gel electrophoresis, capillary electrophoresis, chromatography, filtration, precipitation, liquid or other extraction methods, immunoprecipitation, or a combination thereof.

In a further case, the kit of the present disclosure can optionally comprise instructions for separating and/or detecting proteins or peptides according to the present disclosure. The instructions can also include instructions for how to use the kit, how to prepare the samples, the kinds of samples to use, how to analyze and interpret the results.

In certain cases, the compositions and kits of the present disclosure contain polymer dots that comprise a lyophilized polymer selected from a semiconducting polymer, a non-semiconducting polymer, or a blend thereof.

In some cases, the polymer dots in the compositions and kits have a critical dimension of less than 30 nm, less than 25 nm, less than 20 nm, less than 15 nm, less than 10 nm or less than 5 nm.

In some cases, the compositions or kits comprise chromophoric polymer dots that have undergone an intermediate functionalizing step, such as carboxylation.

In certain cases, the kits of the present disclosure further provide reagents for conjugating the polymer dots to the biomolecules.

In some cases, the compositions or kits comprise chromophoric polymer dots that have been conjugated to one or more biomolecules that provide a function or other benefit, such as binding affinity for a target molecule.

In some cases, the compositions and kits of the present disclosure have a conjugation biomolecule that is conjugated to the polymer dots. That conjugation biomolecule can be a protein or other suitable biomolecule. In further cases, the biomolecule can be an antibody or avidin.

In some cases, the compositions or kits comprise chromophoric polymer dots conjugated to primary antibodies that specifically bind a target protein. In some cases, the kit comprises chromophoric polymer dots conjugated to secondary antibodies that specifically bind a target primary antibody. In some cases, the kit comprises chromophoric polymer dots conjugated to avidins that specifically bind biotin and/or biotinylated targets. In some cases, the kit comprises chromophoric polymer dots conjugated to one or more molecules that alter other properties of the chromophoric polymer dots, such as their size, fluorescence, hydrophobicity, non-specific binding or adsorption properties, and the like.

In some cases, the composition or kit comprises reagents configured for an end user to conjugate chromophoric polymer dots to proteins or peptides for use in performing an assay. In some cases, the kit comprises chromophoric polymer dots (e.g., CN-PPV or BODIPY derivatives as described herein and in WO2013/101902), biomolecules (e.g., streptavidin), PEG, and/or EDL. In other cases, the kit comprises other chromophoric polymer dots, biomolecules, and reagents configured for an end user to conjugate chromophoric polymer dots to biomolecules for use in performing an assay.

In various cases, the present disclosure provides compositions comprising conjugated polymer dots for Western blot analysis. In other cases, the present disclosure provides kits comprising conjugated polymer dots and at least one blocking agent for Western blot analysis. In other cases, the present disclosure provides kits for performing Western blot analysis, the kit comprising polymer dots, a conjugation biomolecule, and a blocking agent.

In other cases, the present disclosure provides kits for performing a protein or peptide analysis, the kit comprising lyophilized polymer dots and/or a conjugation biomolecule. In some cases, the polymer dots comprise a polymer selected from a semiconducting polymer, a non-semiconducting polymer, or a combination thereof. In further cases, the polymer dot comprises a BODIPY derivative. In still further cases, the BODIPY derivative has the structure of Formula (I):

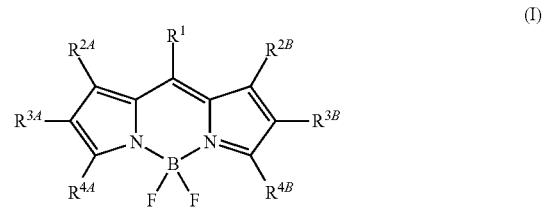

wherein each of $R^1$, $R^{2A}$, $R^{2B}$, $R^{3A}$, $R^{3B}$, $R^{4A}$ and $R^{4B}$ is independently selected from hydrogen, alkyl, aralkyl, aryl, and alkoxy-aryl, and wherein the BODIPY derivative is integrated into the chromophoric polymer by attachment to $R^1$, $R^{2A}$, $R^{2B}$, $R^{3A}$, $R^{3B}$, $R^{4A}$ and $R^{4B}$, or a combination thereof. In certain cases, the polymer dots comprise a polymer consisting of CN-PPV.

In some cases, the polymer dots comprises a polymer selected from a poly((meth)acrylic acid)-based polymer, a polydiene-based polymer, a poly(ethylene oxide)-based polymer, a polyisobutylene-based polymer, a polystyrene-based polymer, a polysiloxane-based polymer, a poly(ferrocenyldimethylsilane)-based polymer, a poly(2-vinyl naphthalene)-based polymer, a poly(vinyl pyridine)-based polymer, a poly(N-methyl vinyl pyridinium iodide)-based polymer, or a poly(vinyl pyrrolidone)-based polymer.

In various cases, the polymer dots comprise a polymer selected from poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(m-ethyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid), poly(butadiene(1,2 addition)-b-ethylene oxide), poly(butadiene(1,2 addition)-b-methylacrylic acid, poly(butadiene(1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly(isoprene-b-ethylene oxide), and poly(isoprene-b-N-methyl 2-vinyl pyridinium iodide), poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline), poly(isobutylene-b-acrylic acid), poly(isobutylene-b-ethylene oxide), poly(isobutylene-b-methacrylic acid), poly(styrene-b-acrylamide), poly(styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate), poly(dimethylsiloxane-b-acrylic acid), poly(dimethylsiloxane-b-ethylene oxide), poly(dimethylsiloxane-b-methacrylic acid), poly(ferrocenyldimethylsilane-b-ethylene oxide), poly(2-vinyl naphthalene-b-acrylic acid), poly(2-vinyl pyridine-b-ethylene oxide), poly(2-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(4-vinyl pyridine-b-ethylene oxide), poly(vinyl pyrrolidone-b-D/L-lactide), PDHF, PFO, PFPV, PFBT, PFTBT, MEH-PPV, CN-PPV, PPE, or a combination thereof.

In some cases, the polymer dot is surrounded by a polyelectrolyte coating. In some cases, the polyelectrolyte coating comprises a polyelectrolyte selected from the group consisting of poly(styrene sulfonate), polyphosphate, polyacrylates, polymethacrylates, polyacrylate-co-maleate, polyacrylamide, chitosan, polysaccharide, polylysine, polyhistidine, and polypeptide. In further cases, the polyelectrolyte coating comprises a polyelectrolyte polymer, wherein each repeating unit of the polyelectrolyte polymer comprises a charge group selected from the group consisting of carboxyl, sulfonate, phosphate, amino, hydroxyl, and mercapto.

In some cases, the polymer dots comprise a functional group attached to the polymer dot. In certain cases, the functional group is selected from a hydrophobic functional group, a hydrophilic functional group, or a combination thereof. In various cases, the functional group is suitable for bioconjugation. In some cases, the functional group is selected from aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, or a combination thereof. In some cases, the conjugation biomolecule is conjugated to the polymer dots. In further cases, the biomolecule is a protein. In still further cases, the biomolecule is an antibody or an avidin.

In some cases, the blocking agent modifies the non-specific adsorption properties of the conjugated polymer dots or wherein the blocking agent modifies the non-specific adsorption properties of the polymer dots. In further cases, the blocking agent competes with the polymer dots for adsorption onto a surface or a membrane. In yet further cases, the blocking agent competes with the polymer dots for binding of one or more biomolecules.

In some cases, the kits further comprise reagents for conjugating the polymer dots to the biomolecules.

In certain cases, the kits comprise membranes selected from a nitrocellulose or a fluoropolymer membrane. In further cases, the fluoropolymer is PVDF.

In some cases, the kits further comprise PEG, EDL, or a combination thereof.

As described herein, a kit may comprise any lyophilized composition described herein. In some cases, the kit may include a fluorescent nanoparticle, an aqueous solution suitable for dispersing the lyophilized composition, a set of instructions describing combining the lyophilized composition and the aqueous solution and agitating the combination the composition and the aqueous solution such that the lyophilized composition becomes dispersed in the aqueous solution.

In some cases, the kit may further comprise a carbohydrate, often the carbohydrate comprises a monosaccharide, a disaccharide, an oligosaccharide, a polysaccharide, or a combination thereof. In some cases, the kit may further comprise an alditol, hydroxypropyl-cyclodextrin, BSA, or a combination thereof. For example, the kit may further comprise a disaccharide. Often, the disaccharide may be present between about 1% w/v and 50% w/v or the disaccharide may be present between about 10% w/v and 20% w/v. In some cases, the disaccharide is selected from the group consisting of sucrose, trehalose dihydrate, maltose monohydrate, and lactose monohydrate. Often, the disaccharide is sucrose. For example, sucrose may be present between about 10% w/v and 20% w/v. Often, the disaccharide may be present between 1% w/v and 50% w/v or the disaccharide may be present between 10% w/v and 20% w/v. In some cases, the disaccharide is selected from the group consisting of sucrose, trehalose dihydrate, maltose monohydrate, and lactose monohydrate. Often, the disaccharide is sucrose. For example, sucrose may be present between 10% w/v and 20% w/v.

In some cases, the kit may further comprise a fluorescent nanoparticle that may be conjugated to a biomolecule. In some cases, the biomolecule is selected from a protein, antibody, nucleic acid molecule, lipid, peptide, aptamer, drug, or a combination thereof. For example, the biomolecule is streptavidin. For another example, the biomolecule is an antibody. For another example, the biomolecule is an aptamer. For another example, the biomolecule is a nucleic acid. For another example, the biomolecule comprises an antibody.

The disclosure now being fully described, it is apparent to one of ordinary skill in the art that various changes and modifications can be made without departing from the spirit or scope of the disclosure.

EXEMPLARY ASPECTS

The present disclosure has been described in terms of particular cases found or proposed to comprise preferred modes for the practice of the disclosure. It is appreciated by those of skill in the art that, in light of the present disclosure, numerous modifications and changes can be made in the particular cases exemplified without departing from the intended scope of the disclosure. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following examples are put forth so as to provide those of ordinary skill in the art with a complete disclosure and description of how to make and use the present disclosure and are not intended to limit the scope of what is regarded as the disclosure nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Preparation of Chromophoric Polymer Dots by Lyophilization

This example describes lyophilization, a freeze-drying/dehydration technique, that can be used to prepare chromophoric polymer dot bioconjugates for long-term storage or shipping, provided the right conditions are used. Lyophilization is an important practical advance for making chromophoric polymer dots practical to use in biomedical research.

Materials.

Poly[(9,9-dioctylfluorenyl-2,7-diyl)-co-(1,4-benzo-(2,10,3)-thiadiazole)] (PFBT; MW, 157 000 Da; polydispersity, 3.0), Poly(9,9-dioctylfluorenyl-2,7-diyl) end capped with dimethyl phenyl (PFO, MW 120000 Da), poly[(9,9-dioctylfluorenyl-2,7-diyl)-co-(1,4-benzo-(2,1',3)-thiadiazole)] 10% benzothiadiazole (PF10BT, MW 100000 Da) and poly[2-methoxy-5-(2-ethylhexyloxy)-1,4-(1-cyanovinylene-1,4-phenylene)] (CNPPV, MW 15000 Da) were purchased from American Dye Source Inc (Quebec, Canada). PFBT directly functionalized with carboxylic acid (PFBT-COOH) groups was synthesized in our lab. Polystyrene-grafted ethylene oxide functionalized with carboxyl groups (PS-PEG-COOH; MW 21,700 Da of PS moiety; 1200 Da of PEG-COOH; polydispersity, 1.25) were purchased from Polymer Source Inc. (Quebec, Canada). Sucrose was ordered from Avantor Performance Materials (Phillipsburg, N.J., USA). Streptavidin was purchased from Invitrogen (Eugene, Oreg., USA). Bovine serum albumin (BSA) and ethylcarbodiimide hydrochloride (EDC) were bought from Sigma (St. Louis, Mo., USA).

Streptavidin Conjugation of Chromophoric Polymer Dots.

Chromophoric polymer dots were prepared using a nanoreprecipitation method as reported earlier. Wu et al., J. American chem. Soc. 132: 15410-15417 (2010). Briefly, a tetrahydrofuran (THF) solution containing 50 µg/mL of semiconducting polymer (PFBT, CNPPV, PFO or PF10BT) and 16 µg/mL of PS-PEG-COOH was prepared. A 5-mL aliquot of the mixture was quickly injected into 10 mL of water under vigorous sonication. THF was removed by blowing nitrogen gas into the solution at 90° C. The THF-free chromophoric polymer dot solution was sonicated for 1-2 minutes and filtrated through a 0.2-µm cellulose membrane filter. For PFBT-COOH chromophoric polymer dots, no additional PS-PEG-COOH was added. THF solution containing only 50 µg/mL PFBT-COOH was injected into water directly. In a typical conjugation reaction, 80 µL of polyethylene glycol (5% w/v PEG, MW 3350) and 80 µL of HEPES buffer (1M, PH 7.3) was added to 4 mL of chromophoric polymer dot solution. Streptavidin (1 mg/mL, 30 µL) was then added to the solution and mixed well. Finally, 80 µL of freshly-prepared EDC solution (5 mg/mL in MilliQ water) was added to the solution, and the mixture was magnetically stirred for 4 hr at room temperature. The resulting chromophoric polymer dot conjugates were finally concentrated in a spin column (100K MW) and were purified with a Bio-Rad Econo-Pac 10DG column (Hercules, Calif., USA). After purification, the proper amount of BSA was added to reach a final concentration of 1% (w/v). The hydrodynamic sizes of chromophoric polymer dots were measured with a dynamic light scattering (DLS) spectrometer (Malvern Zetasizer Nano ZS, Worcestershire, United Kingdom). Fluorescence quantum yields were collected using an integrating sphere (model C9920-02, Hamamatsu Photonics) with proper wavelength excitation. Fluorescence spectra of chromophoric polymer dots were taken with a Fluorolog-3 fluorospectrometer (HORIBA JobinYvon, NJ, USA).

Lyophilization.

Solutions of streptavidin-conjugated chromophoric polymer dots or unconjugated chromophoric polymer dots were prepared at two different concentrations (4 nM and 20 nM) by diluting the chromophoric polymer dot solution with a buffer that was composed of 20 mM HEPES (pH 7.3), 0.1% (w/v) PEG and 0.05% (w/v) BSA. For PFBT, chromophoric polymer dots at 100 nM concentration were also prepared. Sucrose was added to reach the desired final concentrations (10%, w/v). The stock chromophoric polymer dot solutions were aliquoted into several vials. Half of them were rapidly frozen in liquid nitrogen for 2 minutes, and were immediately placed under vacuum on a Labconco Freezone 6 freeze-dryer (Kansas City, Mo., USA). After ~18 hr, lyophilized samples were removed from the freeze-dryer and were labeled as "lyophilized chromophoric polymer dots" and stored at −80° C. for a desired amount of time (from one day to 6 months). The other half of the aliquots were labeled "unlyophilized" and were placed in a 4° C. refrigerator.

Cell Culture.

The breast cancer cell line, MCF-7, was ordered from American Type Culture Collection (ATCC, Manassas, Va., USA). Cells were cultured at 37° C., 5% CO2 in Eagles minimum essential medium supplemented with 10% Fetal Bovine Serum (FBS) and 1% Pen Strep (5000 units/mL penicillin G, 50 µg/mL streptomycin sulfate in 0.85% NaCl). Cells were cultured prior to experiments until confluence was reached. The cells were harvested from the culture flask by briefly rinsing with culture media followed by incubation with proper amount of Trypsin-EDTA solution (0.25% w/v Trypsin, 0.53 mM EDTA) at 37° C. for 5 minutes. After complete detachment, cells were rinsed, centrifuged, and re-suspended in the culture media. Their concentration was determined by microscopy using a hemacytometer.

Immunofluorescence.

For labeling cell-surface markers with IgG conjugates, a million MCF-7 cells in 100 µL labeling buffer (1×PBS, 2 mM EDTA, 1% BSA) were incubated with 0.3 µL of 0.5 mg/mL biotinylated primary anti-human CD326 EpCAM antibody (eBioScience, San Diego, Calif., USA) on a rotary shaker in the dark and at room temperature for 30 minutes. This was followed by a washing step using the labeling buffer. The cells were incubated with 4 nM streptavidin-conjugated chromophoric polymer dots (diluted from the 20 nM chromophoric polymer dots solution) in BlockAid™ blocking buffer (Invitrogen, Eugene, Oreg., USA) for 30 minutes on a shaker in the dark and at room temperature, followed by two washing steps with the labeling buffer. Negative controls were obtained by incubating cells with streptavidin-conjugated chromophoric polymer dots without any previous incubation with the primary biotinylated antibody. Cell fixation was performed afterwards by dissolving the cell pellet obtained by centrifugation in 500 µL of fixing buffer (1×PBS, 2 mM EDTA, 1% BSA, 1% paraformaldehyde).

Flow Cytometry Experiments.

Measurements were performed on labeled cell samples containing 106 cells/0.5 ml and prepared as previously described. Wu et al., Angewandte chemie-Intl. Ed., 49:9436-9440 (2010). The flow cytometer BD FACSCanto II (BD Bioscience, San Jose, Calif. USA) was used. Cells flowing in the detection chamber were excited by a 488-nm laser light. Side- and forward-scattered light were collected and filtered by a 488/10 nm band-pass filter, while fluorescence emission was collected and filtered by a 502-nm long-pass and a 530/30 nm (for PFBT and PFBT-COOH) or a 582/42 nm (for CNPPV) band-pass filter. All signals were detected by photomultiplier tubes. For all flow experiments, representative populations of detected cells were chosen by selecting an appropriate gate. Detection of cell fluorescence was continued until at least 104 events had been collected in the active gate.

FIG. 1 shows an example lyophilization procedure. After being stored at −80° C. for the desired amount of time (from 1 day to 6 months), a lyophilized aliquot was taken out of the freezer and the appropriate amount of water was added for re-dispersion. The final volume of the reconstituted solution was kept the same as that prior to lyophilization. For comparison, the unlyophilized aliquot stored at 4° C. was used. Both samples had the same composition and were measured with the same instrumentation. Various lyophilization conditions were tested and chose the optimized procedure. Comparisons were made between the lyophilized and unlyophilized chromophoric polymer dot bioconjugates for hydrodynamic size, absorption spectra, emission spectra, quantum yield, and labeling efficiency. The hydrodynamic size was measured, absorption spectra, emission spectra, quantum yield, and labeling efficiency of freshly prepared chromophoric polymer dots versus chromophoric polymer dots stored at 4° C. for one day (unlyophilized 1-day), and found them to be similar in all measured properties.

Polymer Dot Size.

PFBT chromophoric polymer dots were conjugated to strepavidin (Strep-PFBT) to optimize the lyophilization recipe. The particular Strep-PFBT chromophoric polymer dots were prepared with a hydrodynamic diameter of 32 nm (FIG. 2A), which was measured immediately after they were prepared. The same chromophoric polymer dot-streptavidin conjugates were lyophilized without adding any reagents, and then re-hydrated the chromophoric polymer dots with water. Even after vigorous sonication, the hydrodynamic diameter of the rehydrated chromophoric polymer dots had increased to 220 nm, indicating that the lyophilization process had caused severe aggregation of the chromophoric polymer dots. Aggregated chromophoric polymer dot bioconjugates are not suitable for biological studies.

Figure 2:
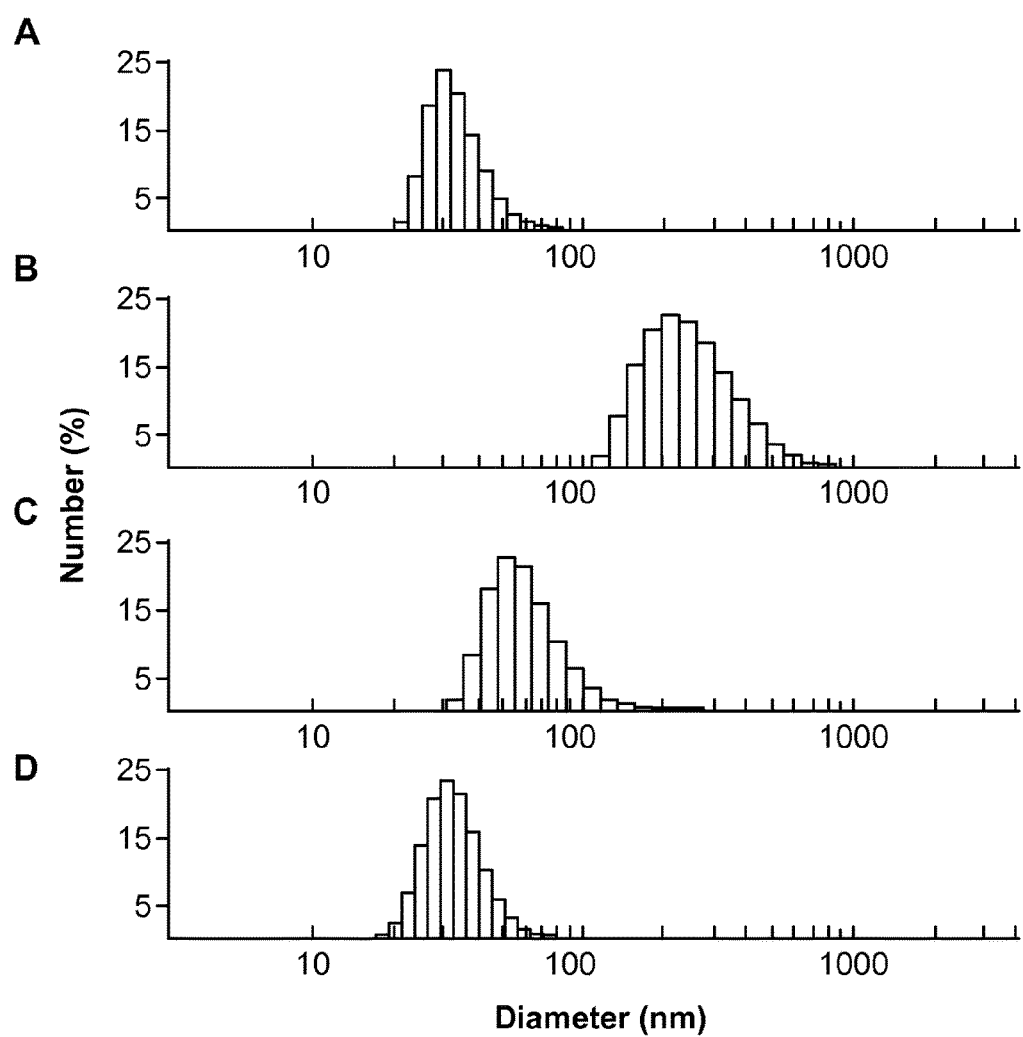
FIGS. 2A-2D provide examplary dynamic light scattering measurements showing size distributions of streptavidin-conjugated PFBT chromophoric polymer dots.
Figure 5:
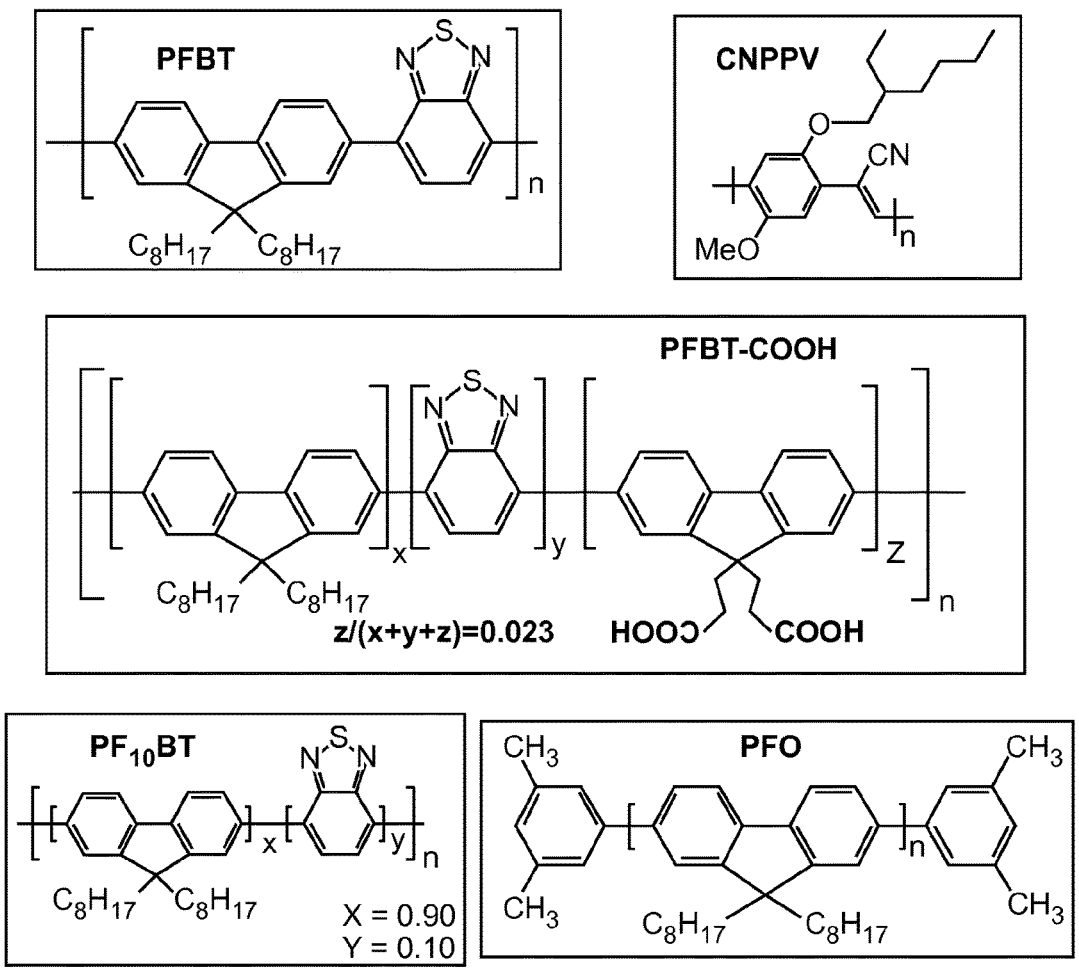
FIG. 5 depicts exemplary main-chain structures of tested chromophoric polymer dots composed of five different conjugated polymers.

A different lyophilization method was used. First, 1% (w/v) sucrose was added and the hydrodynamic diameter of the rehydrated chromophoric polymer dots decreased to 50 nm (FIG. 2C), which was much smaller than the 220 nm obtained without sucrose but it was still significantly larger than the original size of 32 nm. Sonication did not help further shift the size distribution of rehydrated chromophoric polymer dots to that before lyophilization. Therefore, the chromophoric polymer dot-streptavidin bioconjugates still were partially aggregated, albeit much less severely than without sucrose. The concentration of sucrose was increased to 10% (w/v). FIG. 2D shows the size of the rehydrated chromophoric polymer dots returned to 32 nm. It should be noted that additional sonication was not needed after the rehydration procedure. The lyophilized strep-pfbt chromophoric polymer dots used in the above measurements were stored at −80° C. for one day after lyophilization. The lyophilized strep-pfbt chromophoric polymer dots were tested at two different concentrations (4 nm and 20 nm) that were stored for longer (1-6 months) at −80° C. As shown in table 1, the size remained at around 32 nm independent of concentrations after 6 months. 100 nm concentration was also tested and the results were similar to that of 4 and 20 nm. This lyophilization recipe was also applied to chromophoric polymer dots made of other semiconducting polymers (CNPPV, PFO, PF10BT), including both streptavidin conjugated and unconjugated chromophoric polymer dots. The structures of the tested polymers are included in FIG. 5. The hydrodynamic sizes of the chromophoric polymer dots in the solution prior to lyophilization stored over different durations (1-6 months) were measured. The hydrodynamic sizes of the different lyophilized chromophoric polymer dots stored for up to 6 months were also measured and compared with that of their unlyophilized counterparts.

As shown in Table 1, all the lyophilized chromophoric polymer dots possessed similar size to the chromophoric polymer dots in the solution prior to lyophilization after rehydration. To facilitate the bioconjugation reaction and dispersion in aqueous solution, the aforementioned chromophoric polymer dots were functionalized with carboxylic acid groups by doping ps-peg-cooh during preparation. A new type of semiconducting polymers directly functionalized with low density carboxylic acid groups in the same polymer chain was also synthesized in our lab (pfbt-cooh, FIG. 5). With the directly incorporated carboxylic acid groups, pfbt-cooh chromophoric polymer dots offer a number of significant advantages, such as higher brightness and better colloidal stability. The size of such prepared streptavidin conjugated pfbt-cooh chromophoric polymer dots after lyophilization was measured; the sizes of lyophilized strep-pfbt-cooh chromophoric polymer dots stored for 1 month were the same as that of unlyophilized chromophoric polymer dots. The results in Table 1 show that lyophilized chromophoric polymer dots were easily re-dispersed back to their single particle form, independent of the concentration of the initial chromophoric polymer dot solution, even after being stored for up to 6 months. This indicates that the colloidal stability of streptavidin conjugated and unconjugated chromophoric polymer dots did not change after the lyophilization process with 10% sucrose. Therefore, the lyophilization procedure described in the following sections was carried out with 10% sucrose.

The hydrodynamic diameter of lyophilized and unlyophilized streptavidin conjugated and unconjugated chromophoric polymer dots after long term storage is shown in table 1. Strep-pfbt-cooh chromophoric polymer dots were stored at −80° C. for 1 month. All the other chromophoric polymer dots were stored for 6 months. All lyophilized chromophoric polymer dots were rehydrated with water. Both lyophilized and the chromophoric polymer dots in the solution prior to lyophilization were measured with dynamic light scattering without sonication. (lyoph.: lyophilized; unlyoph.: unlyophilized).

TABLE 1

Hydrodynamic diameter of lyophilized and lnlyophilized streptavidin conjugated and unconjugated chromophoric polymer dots after long-term storage.

| Pdot | Concentration (nM) | Lyoph./Unlyoph. | Diameter (nm) |
| --- | --- | --- | --- |
| Strep-PFBT | 4 | Lyoph. | 32 ± 2 |
|  |  | Unlyoph. | 32 ± 2 |
|  | 20 | Lyoph. | 30 ± 2 |
|  |  | Unlyoph. | 32 ± 1 |
|  | 100 | Lyoph. | 32 ± 1 |
|  |  | Unlyoph. | 32 ± 1 |
| Strep-CNPPV | 4 | Lyoph. | 28 ± 2 |
|  |  | Unlyoph. | 28 ± 2 |
|  | 20 | Lyoph. | 29 ± 2 |
|  |  | Unlyoph. | 28 ± 2 |
| Strep-PFBT COOH | 4 | Lyoph. | 26 ± 2 |
|  |  | Unlyoph. | 26 ± 2 |
|  | 20 | Lyoph. | 24 ± 2 |
|  |  | Unlyoph. | 24 ± 2 |
| Unconjugated PFBT | 4 | Lyoph. | 23 ± 2 |
|  |  | Unlyoph. | 21 ± 2 |
|  | 20 | Lyoph. | 22 ± 2 |
|  |  | Unlyoph. | 20 ± 2 |
| Unconjugated CNPPV | 4 | Lyoph. | 21 ± 2 |
|  |  | Unlyoph. | 20 ± 2 |
|  | 20 | Lyoph. | 20 ± 2 |
|  |  | Unlyoph. | 20 ± 2 |
| Unconjugated PFO | 4 | Lyoph. | 21 ± 2 |
|  |  | Unlyoph. | 21 ± 2 |
|  | 20 | Lyoph. | 22 ± 2 |
|  |  | Unlyoph. | 21 ± 2 |
| Unconjugated PF10BT | 4 | Lyoph. | 24 ± 2 |
|  |  | Unlyoph. | 21 ± 2 |
|  | 20 | Lyoph. | 24 ± 2 |
|  |  | Unlyoph. | 22 ± 2 |

Optical Properties.

Figure 3:
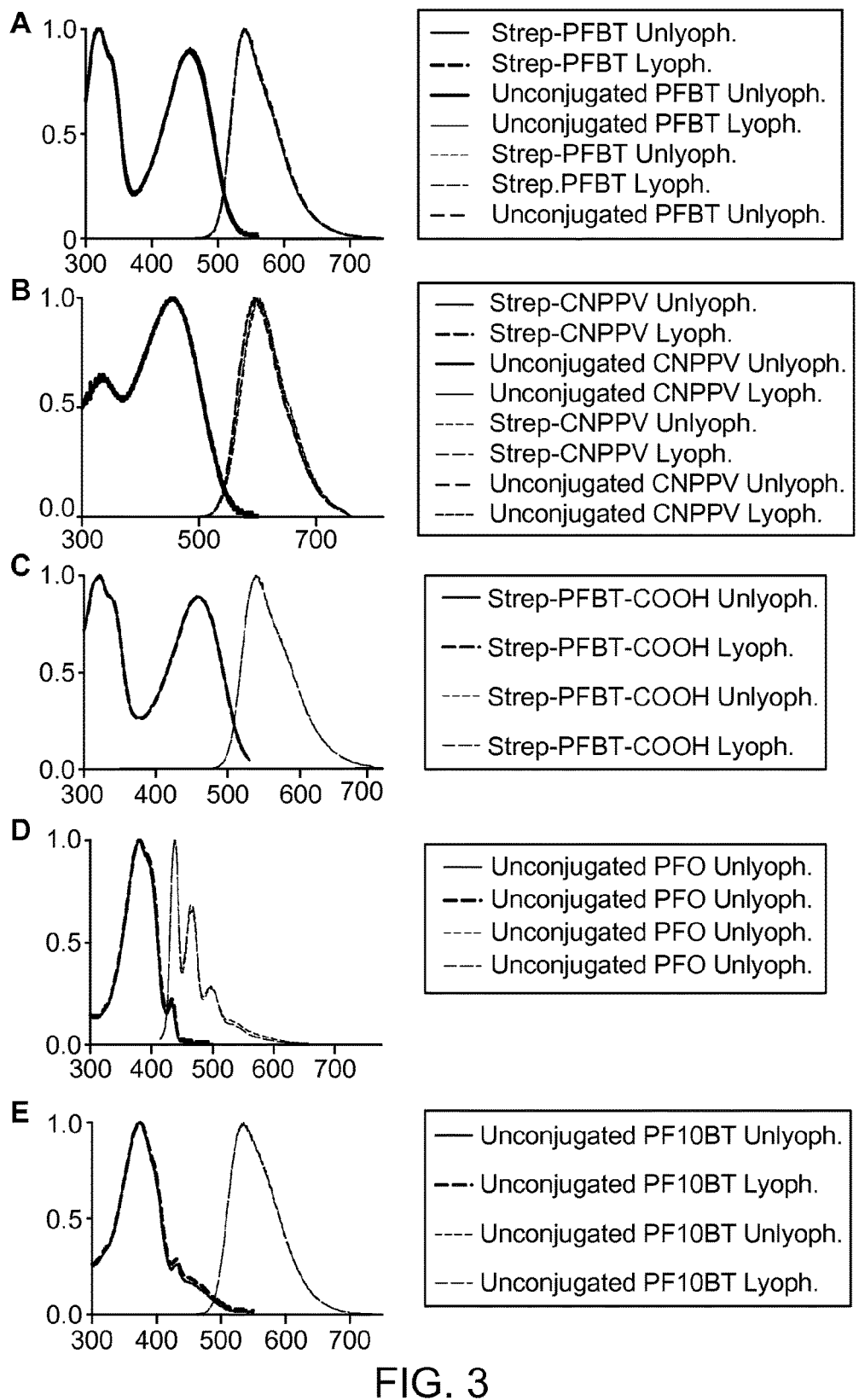
FIGS. 3A-3E show normalized absorption and fluorescence emission spectra of lyophilized and the chromophoric polymer dots in the solution prior to lyophilization stored for up to 6 months. Chromophoric polymer dots were made of PFBT (A), CNPPV (B), PFBT-COOH (C), PFO (D) and PF10BT (E). Chromophoric polymer dots A, B, D and E were stored at −80° C. for 6 months. Chromophoric polymer dots C were stored at −80° C. for 1 month. Solid curves correspond to absorption. Dotted curves correspond to fluorescence emission. The x-axis is wavelength with units in nanometers (nm).

The optical properties of both lyophilized and the chromophoric polymer dots in the solution prior to lyophilization were measured and compared. The absorption spectra, emission spectra, and quantum yield were measured, and both the absorption and emission spectra of lyophilized chromophoric polymer dots after 6 months storage were measured. These values were compared with those of their unlyophilized counterparts. As shown in FIGS. 3A-3C, the absorption and emission spectra of lyophilized streptavidin conjugated chromophoric polymer dots (Strep-PFBT, Strep-CNPPV and Strep-PFBT-COOH) were identical to their unlyophilized counterparts after being stored for up to 6 months. The same phenomenon was also observed in chromophoric polymer dots made of PFO (FIG. 3D) and PF10BT (FIG. 3E). These results indicate lyophilization did not change the absorption and emission spectra of these conjugated and unconjugated chromophoric polymer dots.

The brightness of chromophoric polymer dots was measured to determine if lyophilization had a negative effect on their fluorescence intensity. To facilitate the brightness comparison between lyophilized and the chromophoric polymer dots in the solution prior to lyophilization of different concentrations, their quantum yield (QY) was measured, because quantum yield is less dependent on concentration than fluorescence intensity as shown in Equation (1) below:

$$F = \alpha * I * Q * n \tag{1}$$

Where F is fluorescence emission intensity; $\alpha$ is the instrument factor; I is the excitation intensity; Q is the quantum yield; n is the concentration of chromophoric polymer dots. Table 2 below shows the quantum yield values of various chromophoric polymer dots that had and had not undergone lyophilization. First, the conjugated streptavidin molecules did not affect the quantum yield of chromophoric polymer dots. The quantum yield values of streptavidin conjugated CNPPV and PFBT chromophoric polymer dots stayed at similar levels as their corresponding unconjugated chromophoric polymer dots. For example, the QY values of 4 nM lyophilized Strep-PFBT and unconjugated PFBT chromophoric polymer dots after 6 months storage were both 33%. Second, the quantum yield of lyophilized chromophoric polymer dots did not fluctuate much among different concentrations of chromophoric polymer dots. For example, the QY values of 4 nM lyophilized and 20 nM lyophilized PFO chromophoric polymer dots after 6 months storage were both 47%.

More importantly, the quantum yield of most the chromophoric polymer dots in the solution prior to lyophilization decreased after long term storage, but the quantum yield of lyophilized chromophoric polymer dots remained at the same level for the duration of the storage time. For example, the quantum yield of 20 nM lyophilized Strep-PFBT chromophoric polymer dots was 37% after stored for 1 day and 36% after 6 months storage, respectively. In contrast, the quantum yield of most the chromophoric polymer dots in the solution prior to lyophilization showed a small but consistent decrease: when the same chromophoric polymer dots (20 nM Strep-PFBT chromophoric polymer dots) were stored unlyophilized, the quantum yield decreased from 33% to 30% after 6 months storage. Similar quantum yield changes were also found in unconjugated PFBT and PFO chromophoric polymer dots. It is likely that oxidation of the semiconducting polymer, which would reduce the quantum yield, was minimized when the chromophoric polymer dots were lyophilized and stored at −80° C.

These results demonstrate that the brightness of chromophoric polymer dots certainly was not adversely affected by the lyophilization process, and remarkably, there could even be an enhancement in the optical performance of chromophoric polymer dots by going through the lyophilization procedure. For example, the quantum yield enhancement of 4 nM lyophilized Strep-PFBT chromophoric polymer dots over unlyophilized Strep-PFBT chromophoric polymer dots after 1 day storage was (0.35−0.32)/0.32=9.4%. Although the mechanism that underlies this increase in quantum yield caused by lyophilization is unclear, the lyophilization process may have caused the internal rearrangement of the backbone or internal packing of the semiconducting polymer.

The quantum yield values of lyophilized and the chromophoric polymer dots in the solution prior to lyophilization stored for up to 6 months. For each chromophoric polymer dot, samples with two concentrations (4 nM and 20 nM) were tested (see Table 2 below) (1D: 1 day; 1 M: 1 month; 6 M: 6 months.)

TABLE 2

Quantum yield values of lyophilized and the chromophoric polymer dots in the solution prior to lyophilizationafter storage.

| Pdot | Lyoph./Unlyoph. | Storage Time | Concentration (nM) | Quantum Yield (%) |
|---|---|---|---|---|
| Strep-PFBT | Lyoph. | 1 D | 4 | 35 ± 1 |
| | | | 20 | 37 ± 1 |
| | | | 100 | 35 ± 1 |
| | | 6 M | 4 | 35 ± 1 |
| | | | 20 | 36 ± 1 |
| | | | 100 | 34 ± 1 |
| | Unlyoph. | 1 D | 4 | 32 ± 1 |
| | | | 20 | 33 ± 1 |
| | | | 100 | 32 ± 1 |
| | | 6 M | 4 | 29 ± 1 |
| | | | 20 | 30 ± 1 |
| | | | 100 | 28 ± 1 |
| Strep-CNPPV | Lyoph. | 1 D | 4 | 46 ± 1 |
| | | | 20 | 49 ± 1 |
| | | 6 M | 4 | 49 ± 1 |
| | | | 20 | 48 ± 1 |
| | Unlyoph. | 1 D | 4 | 48 ± 1 |
| | | | 20 | 48 ± 1 |
| | | 6 M | 4 | 48 ± 1 |
| | | | 20 | 48 ± 1 |
| Strep-PFBT-COOH | Lyoph. | 1 D | 4 | 29 ± 1 |
| | | | 20 | 30 ± 1 |
| | | 1 M | 4 | 28 ± 1 |
| | | | 20 | 29 ± 1 |
| | Unlyoph. | 1 D | 4 | 27 ± 1 |
| | | | 20 | 29 ± 1 |
| | | 1 M | 4 | 26 ± 1 |
| | | | 20 | 27 ± 1 |
| Unconjugated PFBT | Lyoph. | 1 D | 4 | 36 ± 1 |
| | | | 20 | 34 ± 1 |
| | | 6 M | 4 | 34 ± 1 |
| | | | 20 | 32 ± 1 |
| | Unlyoph. | 1 D | 4 | 34 ± 1 |
| | | | 20 | 33 ± 1 |
| | | 6 M | 4 | 31 ± 1 |
| | | | 20 | 29 ± 1 |
| Unconjugated CNPPV | Lyoph. | 1 D | 4 | 46 ± 1 |
| | | | 20 | 49 ± 1 |
| | | 6 M | 4 | 49 ± 1 |
| | | | 20 | 50 ± 1 |
| | Unlyoph. | 1 D | 4 | 47 ± 1 |
| | | | 20 | 48 ± 1 |
| | | 6 M | 4 | 47 ± 1 |
| | | | 20 | 49 ± 1 |
| Unconjugated PFO | Lyoph. | 1 D | 4 | 47 ± 1 |
| | | | 20 | 49 ± 1 |
| | | 6 M | 4 | 47 ± 1 |
| | | | 20 | 47 ± 1 |
| | Unlyoph. | 1 D | 4 | 48 ± 1 |
| | | | 20 | 48 ± 1 |
| | | 6 M | 4 | 44 ± 1 |
| | | | 20 | 43 ± 1 |
| Unconjugated $PF_{10}BT$ | Lyoph. | 1 D | 4 | 71 ± 2 |
| | | | 20 | 70 ± 2 |
| | | 6 M | 4 | 70 ± 2 |
| | | | 20 | 71 ± 2 |
| | Unlyoph. | 1 D | 4 | 68 ± 2 |
| | | | 20 | 66 ± 2 |
| | | 6 M | 4 | 67 ± 2 |
| | | | 20 | 70 ± 2 |

Labeling Efficiency.

Under conditions where chromophoric polymer dots retained their colloidal stability after lyophilization and confirmed that the brightness of lyophilized chromophoric polymer dots did not decrease, the cell targeting capability of the chromophoric polymer dot bioconjugates was tested to ensure they maintained their biological specificity. Streptavidin-conjugated chromophoric polymer dots were used to label the cell surface receptor, EpCAM, which is an epithelial cell adhesion marker currently used for the detection of circulating tumor cells. Flow cytometry was used to quantify the brightness of the cell labeling and the degree of non-specific absorption. For comparison between lyophilized and unlyophilized chromophoric polymer dot-streptavidin, 20 nM streptavidin conjugated chromophoric polymer dots (Strep-CNPPV, Strep-PFBT and Strep-PFBT-COOH) were used with 10% sucrose. The labeling efficiency of both lyophilized and unlyophilized chromophoric polymer dot-streptavidin conjugates stored for up to 6 months was tested.

Figure 4:
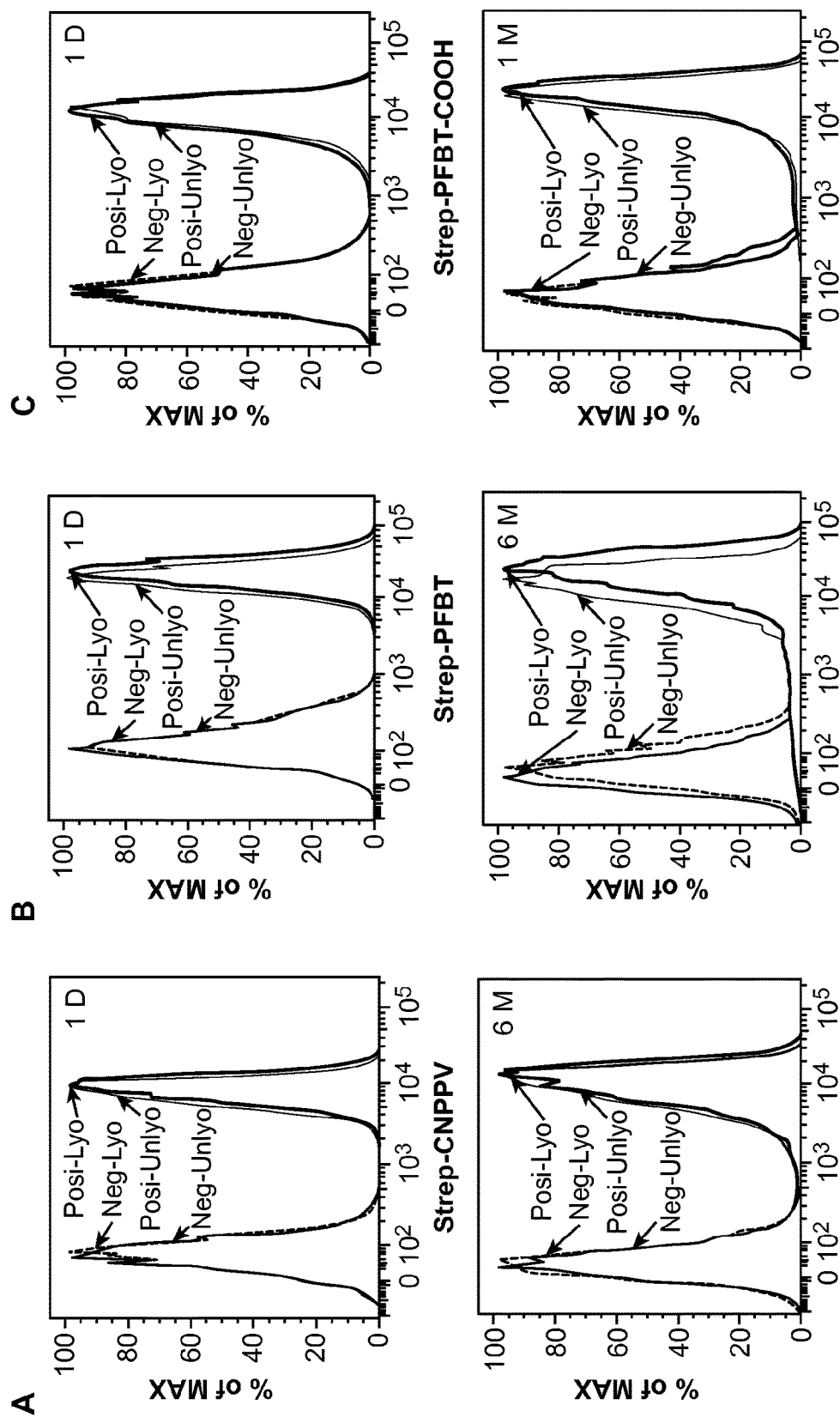
FIG. 4 shows flow cytometry measurements of cells labeled with lyophilized and the chromophoric polymer dots in the solution prior to lyophilization stored for up to 6 months. Column A utilized strep-CNPPV Pdots; column B utilized strep-PFBT Pdots; column C utilized strep-PFBT-COOH Pdots. The x-axis corresponds to relative fluorescence intensity. Chromophoric polymer dots used in the top figures were stored for 1 day. Chromophoric polymer dots used in the bottom figures were stored for a longer term: strep-CNPPV (FIG. 4A, bottom) was stored for 6 months; strep-PFBT (FIG. 4B, bottom) was stored for 6 months; strep-PFBT-COOH (FIG. 4C, bottom) was stored for 1 month. (1D: 1 day; 1 M: 1 month; 6 M: 6 months.)

The non-specific absorption and positive cell labeling by chromophoric polymer dot-streptadvidin that had been lyophilized and stored over various time was compared to chromophoric polymer dots that were not lyophilized. Samples stored for 1 day after lyophilization were first tested. This experiment reports on any potential effect caused by undergoing the lyophilization process. As shown in the top panels in FIG. 4, when cells were incubated with chromophoric polymer dot-streptavidin in the absence of the primary antibody (negative), the intensity peaks of both lyophilized (solid line) and unlyophilized (dashed line) samples were low and comparable. This result confirmed that both lyophilized and the chromophoric polymer dots in the solution prior to lyophilization produced very low amounts of non-specific binding in the absence of the primary antibody.

The data also show that the intensity peaks for cells labeled with both lyophilized solid line) and unlyophilized (dashed line) chromophoric polymer dots in the presence of primary antibody (positive) were well separated from that of the negative control samples. Specifically, for Strep-CNPPV and Strep-PFBT-COOH chromophoric polymer dots, the positive peak intensity values of lyophilized chromophoric polymer dots were similar to that of unlyophilized chromophoric polymer dots. For Strep-PFBT chromophoric polymer dots, the peak intensity value of lyophilized chromophoric polymer dots was a little larger than that of unlyophilized chromophoric polymer dots. The labeling brightness difference is consistent with our measured quantum yield values: for 20 nM Strep-CNPPV and Strep-PFBT-COOH, which were stored for 1 day, the QY values of lyophilized chromophoric polymer dots were similar to that of the chromophoric polymer dots in the solution prior to lyophilization(see Table 2); for Strep-PFBT, the cell labeling enhancement is 10%, which is similar to our measured quantum yield enhancement (9%). This result indicates that the lyophilization process did not impair the performance of chromophoric polymer dot bioconjugates, and for some semiconducting polymers, even enhanced their performance.

The cell labeling efficiency of lyophilized and the chromophoric polymer dots in the solution prior to lyophilization after long term storage was further tested. As displayed in the bottom panels in FIG. 4, the intensity peaks for cells labeled with either lyophilized or the chromophoric polymer dots in the solution prior to lyophilization stored for up to 6 months in the presence of primary antibody (positive) were still well separated from that of negative control samples. Specifically, for Strep-CNPPV chromophoric polymer dots, positive peaks of lyophilized and unlyophilized samples overlapped. For Strep-PFBT-COOH chromophoric polymer dots, positive peak of lyophilized sample was slightly higher than that of unlyophilized sample. For Strep-PFBT chromophoric polymer dots, the lyophilized sample showed a more noticeable brightness enhancement of 22%, which is consistent with our measured quantum yield enhancement of 20%. This result again indicates that the lyophilization process effectively maintained the performance of chromophoric polymer dot bioconjugates. Our data suggest that lyophilization is a good strategy for the long-term storage of chromophoric polymer dot bioconjugates.

Control Experiment.

Figure 6:
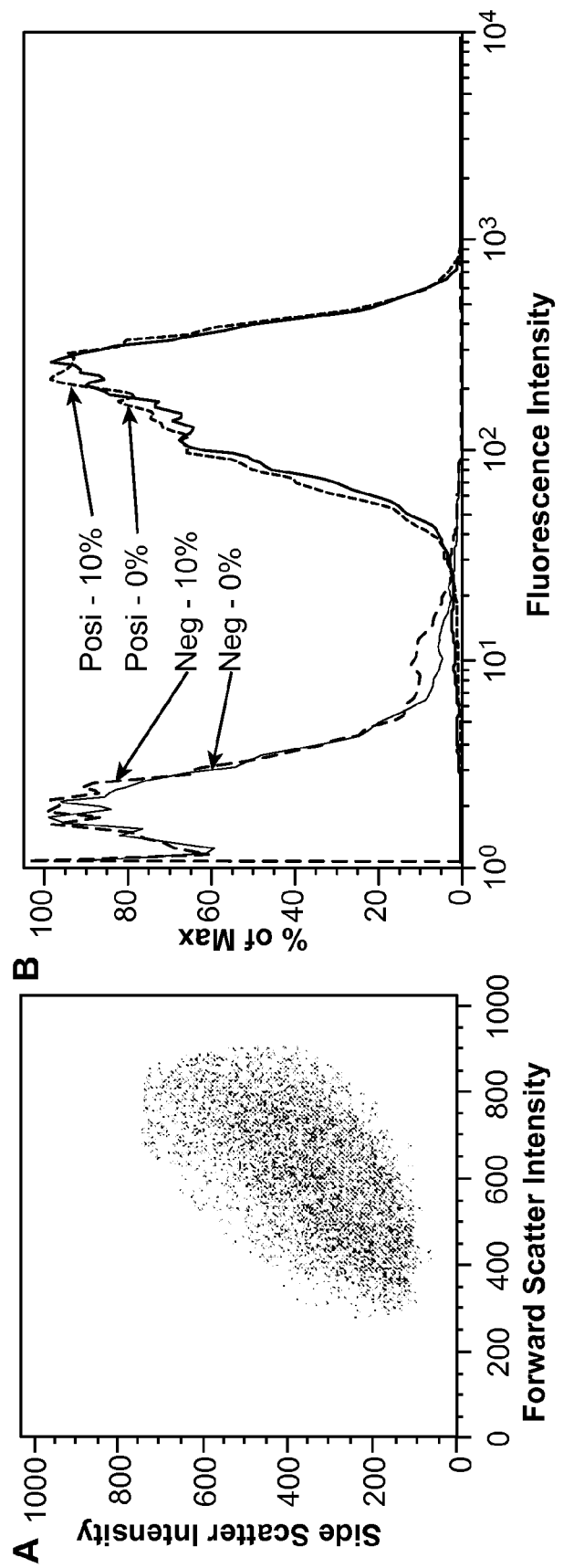
FIGS. 6A and B show results from flow cytometry studies of chromophoric polymer dot-tagged MCF-7 cells in the presence and absence of sucrose during cell labeling.
FIG. 6B shows a fluorescence intensity distribution of MCF-7 cells labeled with chromophoric polymer dot-streptavidin in presence of 10% and 0% sucrose in the chromophoric polymer dot solutions used for cell labeling. The primary antibody used was biotinylated anti-EpCAM; the negative control was carried out under identical conditions as in the cell labeling experiments, but in the absence of the biotinylated primary antibody.

Flow cytometry was used to quantify the brightness of chromophoric polymer dot-tagged MCF-7 cells, where the cells were labeled using chromophoric polymer dot solutions that contained either 10% or 0% sucrose. FIG. 6 shows the resulting flow-cytometry data, which clearly indicates the presence of 10% sucrose had no effect on the brightness of the labeled cells and thus did not affect cell labeling. The negative controls (performed under identical conditions except in the absence of primary antibody) were also similar between these two samples, which shows the presence of sucrose in the chromophoric polymer dot solution also had no effect on the non-specific binding properties of the chromophoric polymer dot bioconjugates.

The flow data was collected with a commercial BD FACSCanto II cytometer (BD Bioscience, San Jose, Calif. USA). Cells were illuminated by 488-nm laser light and fluorescence emission was filtered by a 502-nm long pass filter before being detected by an array of photomultiplier tubes (PMTS).

Figure 7:
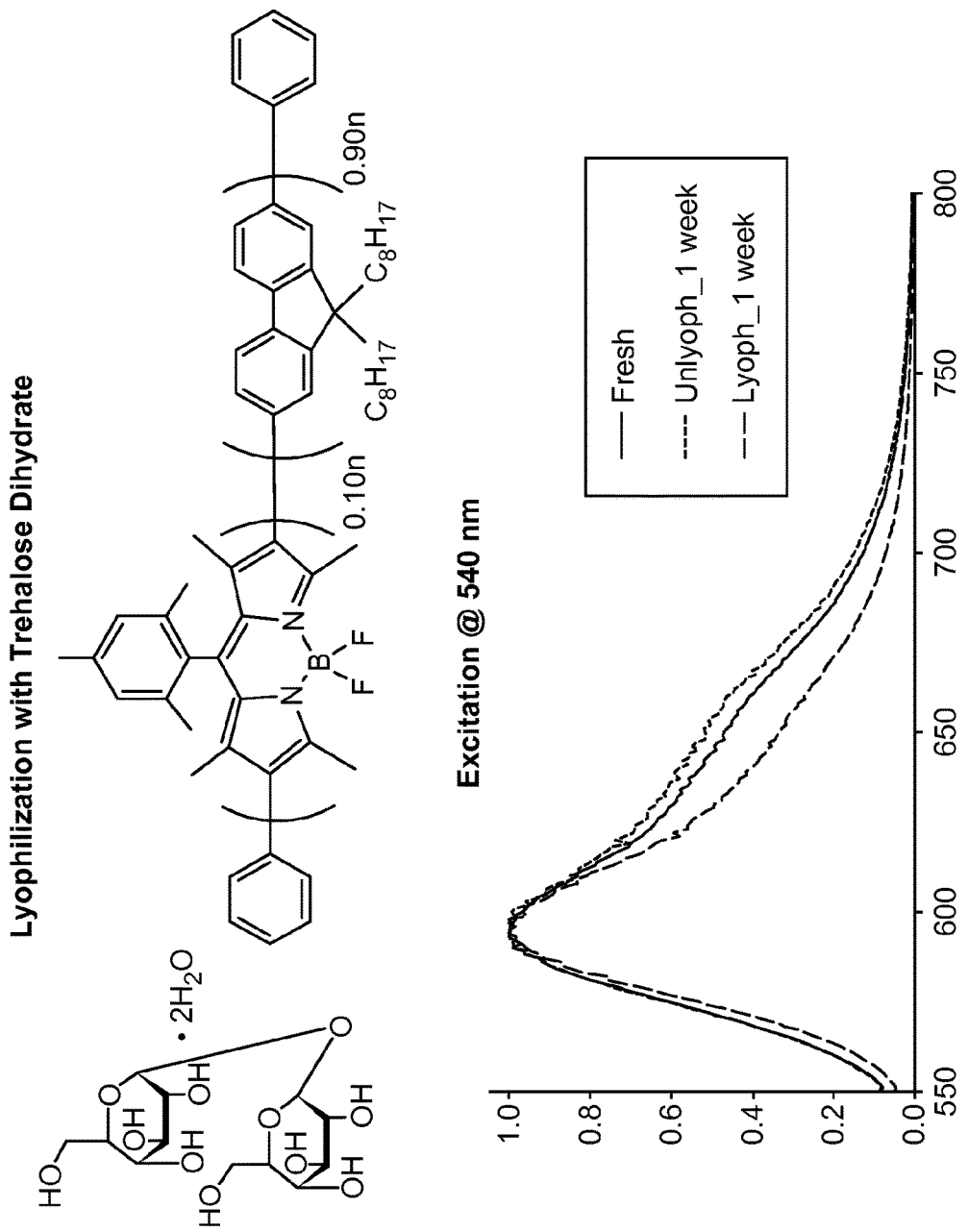
FIG. 7 compares the emission bandwidth for fresh polymer dots, lyophilized polymer dots, and unlyophilized polymer dots. Each of the polymer dot compositions comprised trehalose dihydrate. The chromophoric polymer dots were made of BODIPY-based conjugated polymer with emission peak at 590 nm (BODIPY-590). As shown after 1 week of storage, the emission bandwidth of chromophoric polymer dots without going through the lyophilization process became wider than when the chromophoric polymer dots were freshly prepared. The lyophilized chromophoric polymer dots, however, showed a narrower emission bandwidth.

The effect of lyophilization on the properties of chromophoric polymer dot-streptavidin bioconjugates, including colloidal stability, spectral properties, brightness, and labeling efficiency was determined Samples of various concentrations were stored for up to 6 months. Lyophilization with 10% sucrose was a good strategy to preserve chromophoric polymer dot bioconjugates. The rehydrated chromophoric polymer dots after lyophilization had the same size as that before lyophilization, even in the absence of sonication to help re-disperse the chromophoric polymer dots. The lyophilization procedure did not negatively affect the optical properties of chromophoric polymer dots. The quantum yield values of lyophilized chromophoric polymer dots using sucrose showed a consistent, albeit small, improvement in quantum yield after lyophilization; this phenomenon is likely caused by the rearrangement of the polymer backbone or internal packing during lyophilization. The use of other lyoprotectant molecules other than sucrose can result in much more significant increase in quantum yield (see Example 2), which is an important finding because chromophoric polymer dots with high quantum is highly desired for improving the brightness of the probe for a wide range of application. In addition to improving quantum yield, the use of appropriate lyoprotectant molecules can also result in a narrowing of the emission spectrum of the chromophoric polymer dot (FIG. 7), which is also desired because narrow-band emission chromophoric polymer dots are valuable for their multiplexing capability.

The brightness of cells labeled with lyophilized Strep-PFBT chromophoric polymer dots stored for 6 months showed a 22% enhancement over the unlyophilized counterpart, likely because oxidation of the semiconducting polymer was minimized when the chromophoric polymer dots were lyophilized and stored at −80° C. Lyophilization will be a preferred route for the long-term storage of chromophoric polymer dots, which makes it an important practical consideration for the wide-spread adoption of bioconjugated chromophoric polymer dots in biomedical research.

Example 2

Effect of Sucrose Concentration on Lyophilization of Chromophoric Polymer Dots

This example describes the effect of sucrose concentration on the lyophilization of chromophoric polymer dots. A series of sucrose concentrations (0%, 1%, 10%, 20%, 50%) (w/v) were used to lyophilize chromophoric polymer dots. Two types of chromophoric polymer dots were used. One is PFBT (Mw=73 k)+30% (w/w) PS-PEG-COOH, and the other is the directly functionalized PFBT-COOH 2%. The chromophoric polymer dots were prepared using nanoprecipitation as described in Example 1. The samples had a size of 21 nm at 20 nM concentration in aqueous solution. Different concentration of sucrose was added to the chromophoric polymer dot aqueous solution. The sample was then lyophilized. After lyophilization, the sample was stored in −80° C. freezer for 1 day and then re-dispersed in aqueous solution.

Figure 8:
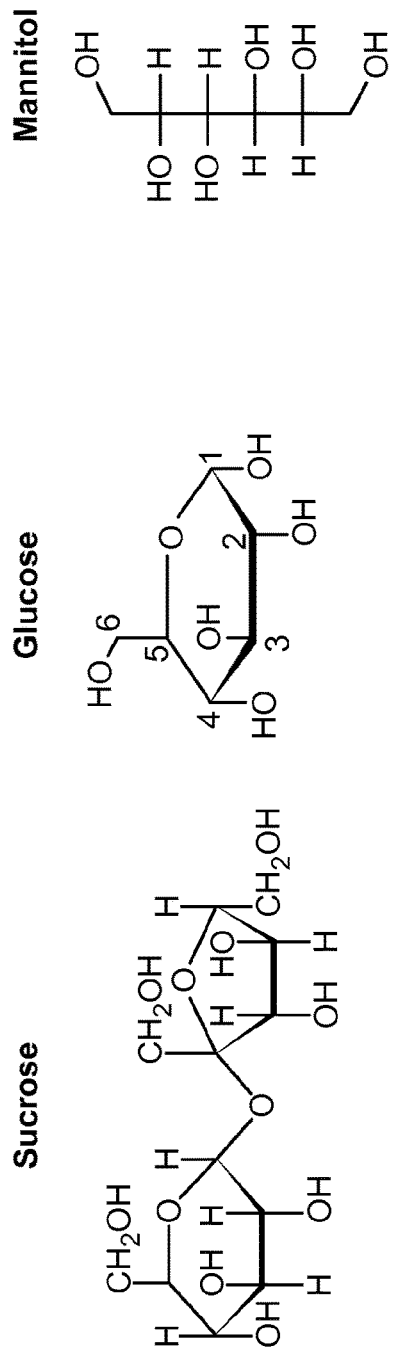
FIG. 8 shows the chemical structures of lyophilization agents used for the chromophoric polymer dots.
Figure 8:
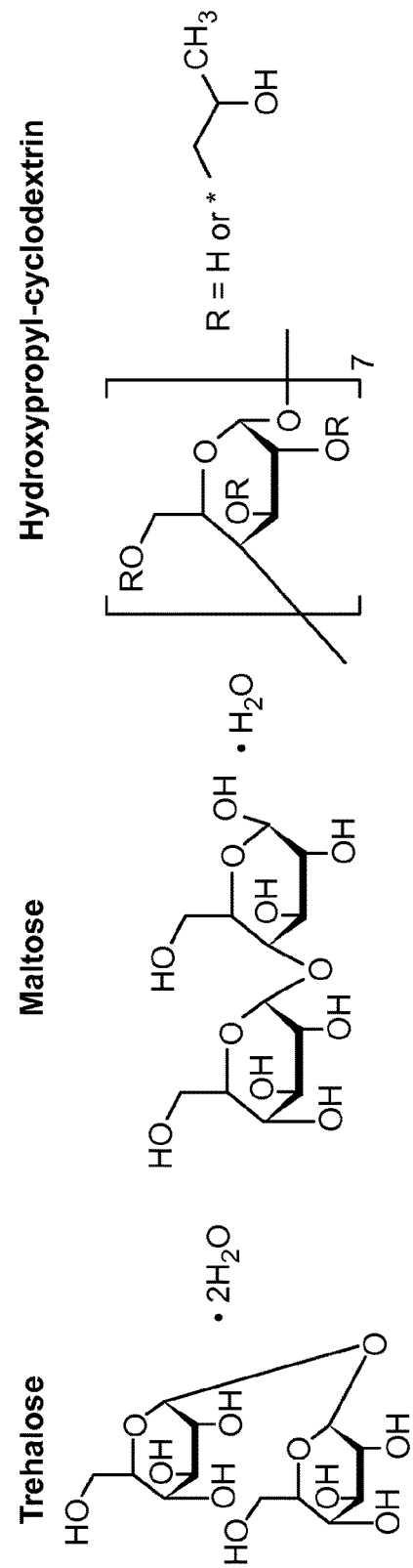

Size and quantum yield were measured to describe whether there is any change of the chromophoric polymer dot after lyophilization (see FIG. 8). Without the addition of sucrose (0%), a size as large as 220 nm for lyophilized PFBT/PS-PEG-COOH chromophoric polymer dot and 230 nm for lyophilized PFBT-COOH2% (their unlyophilized counterparts have the size of ~21 nm) was obtained, indicating serious aggregation during lyophilization. Compared to 0% sucrose, the lyophilization with 1% sucrose resulted in relatively smaller chromophoric polymer dot, i.e., ~50 nm (see Table 3). However, it was still significantly larger than the original size of 21 nm. At a sucrose concentration of 10% or 20%, the lyophilized chromophoric polymer dot showed exactly the same size as that of the original chromophoric polymer dot, both having a size of 21 nm. However, when the sucrose concentration was at 50%, the sample could not be completely dried under vacuum during lyophilization and the lyophilization at this sucrose concentration was not successful.

TABLE 3

Hydrodynamic diameter of chromophoric polymer dots with lyophilization. "N/A" indicates that data is not available because the Pdot cannot be completely dried during lyophilization.

| | Diameter (nm) | | | |
| --- | --- | --- | --- | --- |
| | PFBT/PS-PEG-COOH | | PFBT-COOH-2% | |
| Sucrose (%) | Lyoph. | Unlyoph. | Lyoph. | Unlyoph. |
| 0 | 220 ± 20 | 21 ± 2 | 230 ± 20 | 18 ± 2 |
| 1 | 50 ± 5 | 21 ± 2 | 58 ± 8 | 18 ± 2 |
| 10 | 21 ± 2 | 21 ± 2 | 21 ± 2 | 21 ± 2 |
| 20 | 21 ± 2 | 21 ± 2 | 24 ± 2 | 21 ± 2 |
| 50 | N/A* | 24 ± 2 | N/A* | 21 ± 2 |

Example 3

Use of Various Lyophilization Agents for Lyophilization of Chromophoric Polymer Dots This example describes the use of several lyophilization agents in the application of chromophoric polymer dot lyophilization. The direct functionalized PFBT-COOH 2% chromophoric polymer dots and BODIPY-690 were prepared using nanoprecipitation method as described in Example 1. Both the as-prepared chromophoric polymer dots had a size of ~20 nm and at a concentration of 20 nM in aqueous solution. Different lyophilization agents with 5-20% (w/v) were added to the chromophoric polymer dot aqueous solution. In the combination of lyophilization agents, the total agents concentration was 10% (w/v) in the solution. The sample with lyophilization agent was then lyophilized. After lyophilization, the sample was stored in −80° C. freezer for 1 day and then re-dispersed to aqueous solution.

FIG. 8 shows the chemical structures of the lyophilization agents used for the chromophoric polymer dots; they are sucrose, glucose, mannitol, trehalose, maltose, hydroxypropyl-cyclodextrin, and bovine serum albumin (BSA). In addition, two combination agents were used; they are 5% sucrose+5% trehalose and 5% sucrose+5% maltose.

Size and quantum yield were measured to describe whether there was any change of the chromophoric polymer dots after lyophilization. The results are shown in Table 4 below. The results indicate that the agents used herein were able to lyophilize the chromophoric polymer dots. For example, the size and quantum yield of lyophilized chromophoric polymer dots were similar to its unlyophilized counterpart for many of these lyophilization agents. Remarkably, several agents showed an ability to increase significantly the chromophoric polymer dots' quantum yield after lyophilization. For example, when mannitol was used, the size of the lyophilized PFBT-COOH 2% chromophoric polymer dot did not change as compared to its unlyophilized chromophoric polymer dot (see Table 3 above), but its quantum yield increased ~50% for the chromophoric polymer dots after lyophilization.

TABLE 4

Hydrodynamic diameter and quantum yield of lyophilized chromophoric polymer dots.
PFBT—COOH 2%

| Lyophilization Agents | Concentration (w/v %) | Lyoph./ Unlyoph. | Diameter (nm) | Quantum yield (%) |
| --- | --- | --- | --- | --- |
| Glucose | 5 | Lyoph. | 19 ± 2 | 20 ± 1 |
| | | Unlyoph. | 19 ± 2 | 19 ± 1 |
| | 10 | Lyoph. | 20 ± 2 | 21 ± 1 |
| | | Unlyoph. | 19 ± 2 | 20 ± 1 |
| | 20 | Lyoph. | 44 ± 2 | 20 ± 1 |
| | | Unlyoph. | 20 ± 2 | 20 ± 1 |

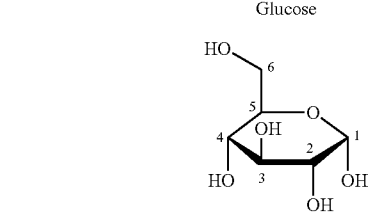

TABLE 4-continued

Hydrodynamic diameter and quantum yield of lyophilized chromophoric polymer dots.
PFBT—COOH 2%

| Lyophilization Agents | Concentration (w/v %) | Lyoph./ Unlyoph. | Diameter (nm) | Quantum yield (%) |
|---|---|---|---|---|
| Mannitol 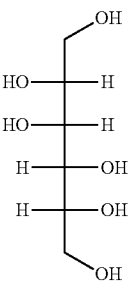 | 5 | Lyoph. | 21 ± 2 | 25 ± 1 |
|  |  | Unlyoph. | 20 ± 2 | 21 ± 1 |
|  | 10 | Lyoph. | 24 ± 2 | 27 ± 1 |
|  |  | Unlyoph. | 21 ± 2 | 21 ± 1 |
|  | 20 | Lyoph. | 21 ± 2 | 30 ± 1 |
|  |  | Unlyoph. | 20 ± 2 | 21 ± 1 |
| Trehalose 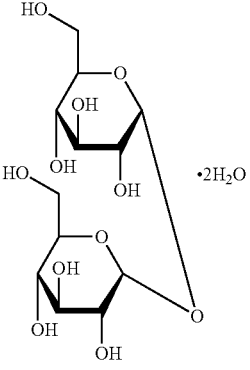 | 5 | Lyoph. | 58 ± 2 | 28 ± 1 |
|  |  | Unlyoph. | 21 ± 2 | 22 ± 1 |
|  | 10 | Lyoph. | 24 ± 2 | 32 ± 1 |
|  |  | Unlyoph. | 20 ± 2 | 23 ± 1 |
|  | 20 | Lyoph. | 28 ± 2 | 22 ± 1 |
|  |  | Unlyoph. | 20 ± 2 | 22 ± 1 |
| Maltose 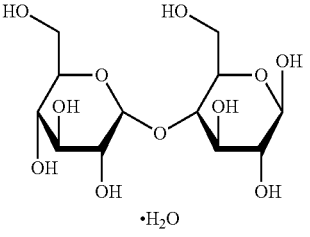 | 5 | Lyoph. | 37 ± 2 | 20 ± 1 |
|  |  | Unlyoph. | 20 ± 2 | 21 ± 1 |
|  | 10 | Lyoph. | 26 ± 2 | 23 ± 1 |
|  |  | Unlyoph. | 21 ± 2 | 21 ± 1 |
|  | 20 | Lyoph. | 21 ± 2 | 23 ± 1 |
|  |  | Unlyoph. | 20 ± 2 | 22 ± 1 |
| Hydroxypropyl-cyclodextrin 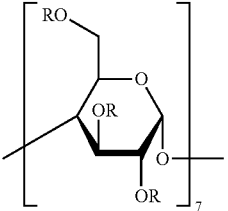 R = H or *—CH(OH)CH$_3$ | 5 | Lyoph. | 19 ± 2 | 28 ± 1 |
|  |  | Unlyoph. | 20 ± 2 | 22 ± 1 |
|  | 10 | Lyoph. | 18 ± 2 | 33 ± 1 |
|  |  | Unlyoph. | 19 ± 2 | 23 ± 1 |
|  | 20 | Lyoph. | 20 ± 2 | 33 ± 1 |
|  |  | Unlyoph. | 20 ± 2 | 24 ± 1 |
| bovine serum albumin (BSA) Mw = 66.5 kDA | 5 | Lyoph. | N/A* | 26 ± 1 |
|  |  | Unlyoph. | N/A* | 18 ± 1 |
|  | 10 | Lyoph. | N/A* | 26 ± 1 |
|  |  | Unlyoph. | N/A* | 19 ± 1 |

TABLE 4-continued

Hydrodynamic diameter and quantum yield of lyophilized chromophoric polymer dots.
PFBT—COOH 2%

| Lyophilization Agents | Concentration (w/v %) | Lyoph./ Unlyoph. | Diameter (nm) | Quantum yield (%) |
|---|---|---|---|---|
|  | 20 | Lyoph. | N/A* | 28 ± 1 |
|  |  | Unlyoph. | N/A* | 25 ± 1 |
| 5% Sucrose + 5% Trehalose | 10 | Lyoph. | 24 ± 2 | 20 ± 1 |
|  |  | Unlyoph. | 20 ± 2 | 22 ± 1 |
| 5% Sucrose + 5% Maltose | 10 | Lyoph. | 24 ± 2 | 20 ± 1 |
|  |  | Unlyoph. | 21 ± 2 | 21 ± 1 |

For BODIPY-690 chromophoric polymer dot, its quantum yield showed ~20% increase as compared to its unlyophilized counterpart as shown in Table 5 below.

TABLE 5

Quantum yield for various lyophilization agents with BODIPY-690 polymer dot compositions.
BODIPY-690

| Lyophilization agent | Concentration (w/v %) | Lyoph./ Unlyoph. | Quantum yield (%) |
|---|---|---|---|
| Mannitol | 10 | Lyoph. | 20 ± 1 |
|  |  | Unlyoph. | 17 ± 1 |
| Trehalose | 10 | Lyoph. | 20 ± 1 |
|  |  | Unlyoph. | 16 ± 1 |
| Hydroxypropyl-cyclodextrin | 10 | Lyoph. | 21 ± 1 |
|  |  | Unlyoph. | 16 ± 1 |
| BSA | 10 | Lyoph. | 18 ± 1 |
|  |  | Unlyoph. | 16 ± 1 |

When hydroxypropyl-cyclodextrin was used, the quantum yield of lyophilized PFBT-COOH 2% chromophoric polymer dot showed ~75% increase (see Table 6) and lyophilized BODIPY-690 showed ~30% increase (see Table 5) as compared to their unlyophilized counterparts, respectively.

TABLE 6

Quantum yield of chromophoric polymer dots with lyophilization as a function of sucrose concentration. "N/A" indicates that data is not available because the Pdot could not be completely dried during lyophilization.

| | Quantum Yield (%) | | | |
|---|---|---|---|---|
| | PFBT/ PS-PEG-COOH | | PFBT-COOH-2% | |
| Sucrose (%) | Lyoph. | Unlyoph. | Lyoph. | Unlyoph. |
| 1 | 25 ± 1 | 24 ± 1 | 32 ± 1 | 32 ± 1 |
| 10 | 25 ± 1 | 24 ± 1 | 33 ± 1 | 32 ± 1 |
| 20 | 24 ± 1 | 24 ± 1 | 34 ± 1 | 34 ± 1 |
| 50 | N/A* | 24 ± 1 | N/A* | 33 ± 1 |

Example 4

Lyophilization of BODIPY-Conjugated Chromophoric Polymer Dots

This example describes the lyophilization of three types of BODIPY based chromophoric polymer dots with centered emission at 570 nm, 590 nm and 690 nm. It shows the lyophilized BODIPY chromophoric polymer dots can be stored for at least 6 months.

Figure 9:
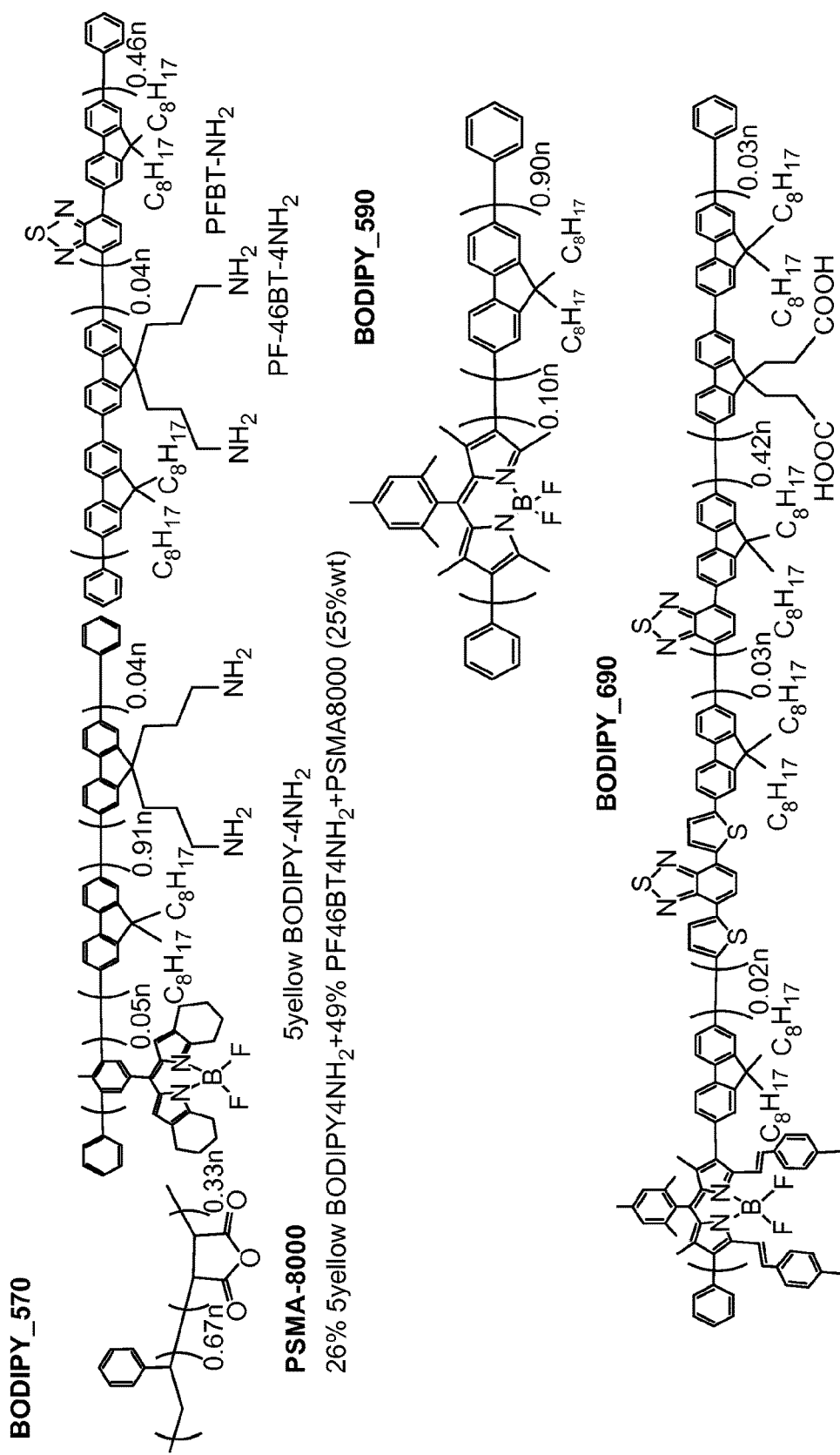
FIG. 9 shows the structures of exemplary main-chain components of tested chromophoric polymer dots composed of three different BODIPY-based conjugated polymers, BODIPY-570, 590 and 690.
Figure 10:
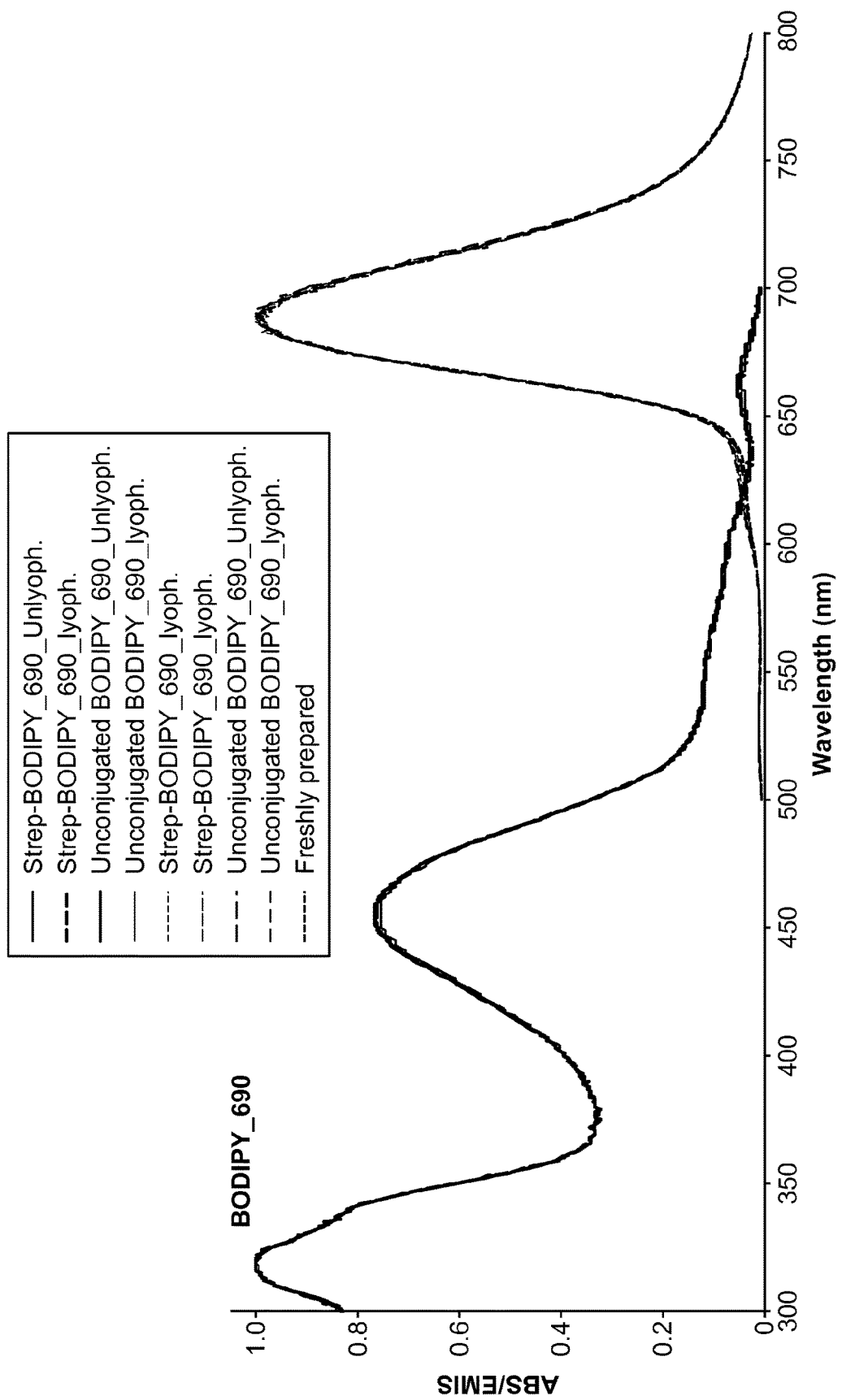
FIG. 10 shows the optical properties of unconjugated/conjugated and unlyophilized/lyophilized BODIPY-690 chromophoric polymer dots.

FIG. 9 shows the structures of the three BODIPY-based polymer structures. The chromophoric polymer dots were prepared by mixing the BODIPY-based conjugated polymer with 30% PS-PEG-COOH (w/w) using the nanoprecipitation method. The three types of chromophoric polymer dots had a size of ~23 nm at 20 nM concentration in aqueous solution. The BODIPY-690 chromophoric polymer dot was bioconjugated by covalently linking streptavidin to the chromophoric polymer dot, which gave a ~4 nm increase to the final chromophoric polymer dot size. All the chromophoric polymer dots (including the BODIPY-690 chromophoric polymer dot conjugated to streptavidin) were lyophilized with 10% sucrose (w/v). After lyophilization, the sample was stored in −80° C. freezer for up to 6 months and then was re-dispersed in aqueous solution and the size and quantum yield were measured.

Table 7 below shows the size and quantum yield values of various BODIPY-based chromophoric polymer dots that had and had not undergone lyophilization. The conjugated streptavidin molecules did not affect the quantum yield of BODIPY-based chromophoric polymer dots. The quantum yield values of streptavidin conjugated BODIPY-690 stayed at similar levels as their corresponding unconjugated chromophoric polymer dots. Second, compared to their unlyophilized counterparts, the size and quantum yield of lyophilized chromophoric polymer dots did not change much.

TABLE 7

Quantum yield of chromopohoric polymer dots of varied composition and size with and without lyophilization.

| Pdot | Lyoph./ Unlyoph. | Storage Time | Concentration (nM) | Size (nm) | Quantum Yield (%) |
|---|---|---|---|---|---|
| Unconjugated BODIPY_570 | Lyoph. | 1 D | 20 | 23 (±2) | 29 ± 1 |
|  |  | 1 M |  | 23 (±2) | 30 ± 1 |
|  | Unlyoph. | 1 D | 20 | 22 (±2) | 29 ± 1 |
|  |  | 1 M |  | 22 (±2) | 29 ± 1 |
| Unconjugated BODIPY_590 | Lyoph. | 1 D | 20 | 24 (±2) | 6.0 ± 0.2 |
|  |  | 6 M |  | 24 (±2) | 5.6 ± 0.2 |
|  | Unlyoph. | 1 D | 20 | 22 (±2) | 6.0 ± 0.2 |
|  |  | 6 M |  | 22 (±2) | 5.5 ± 0.2 |
| Unconjugated BODIPY_690 | Lyoph. | 1 D | 20 | 23 (±2) | 19 ± 1 |
|  |  | 1 M |  | 23 (±2) | 17 ± 1 |
|  | Unlyoph. | 1 D | 20 | 23 (±2) | 19 ± 1 |
|  |  | 1 M |  | 23 (±2) | 17 ± 1 |
| Strep_BODIPY_690 | Lyoph. | 1 D | 20 | 28 (±2) | 18 ± 1 |
|  |  | 1 M |  | 28 (±2) | 19 ± 1 |
|  | Unlyoph. | 1 D | 20 | 28 (±2) | 18 ± 1 |
|  |  | 1 M |  | 28 (±2) | 17 ± 1 |

The optical properties of both lyophilized and the chromophoric polymer dots in the solution prior to lyophilization were measured and compared. The absorption and emission spectra of lyophilized chromophoric polymer dots were measured after 6 months storage and compared them with that of their unlyophilized counterparts. As shown in Table 7, the absorption and emission spectra of lyophilized streptavidin conjugated BODIPY-690 chromophoric polymer dots were similar to their unlyophilized counterparts after being stored for up to 6 months.

While preferred cases of the present disclosure have been shown and described herein, it will be obvious to those skilled in the art that such cases are provided by way of example only. Numerous variations, changes, and substitutions will now occur to those skilled in the art without departing from the disclosure. It should be understood that various alternatives to the cases of the disclosure described herein may be employed in practicing the disclosure. It is intended that the following claims define the scope of the disclosure and that methods and structures within the scope of these claims and their equivalents be covered thereby.

What is claimed is:

1. A lyophilized composition comprising:
   a lyophilization agent that comprises a carbohydrate; and
   a plurality of fluorescent nanoparticles, wherein:
      each fluorescent nanoparticle in the plurality of fluorescent nanoparticles comprises at least one condensed conjugated, semiconducting polymer; and
      the plurality of fluorescent nanoparticles after lyophilization has a quantum yield that is greater than 80% of the quantum yield of the plurality of fluorescent nanoparticles that have not been lyophilized,
   wherein the lyophilization agent is present between about 1% w/v and 50% w/v.

2. The lyophilized composition of claim 1, wherein the carbohydrate comprises a monosaccharide, a disaccharide, an oligosaccharide, a polysaccharide, or any combination thereof.

3. The lyophilized composition of claim 2, wherein the disaccharide is selected from the group consisting of sucrose, trehalose dihydrate, maltose monohydrate, and lactose monohydrate.

4. The lyophilized composition of claim 1, wherein the lyophilization agent further comprises an alditol, hydroxypropyl-cyclodextrin, BSA, or any combination thereof.

5. The lyophilized composition of claim 1, wherein the plurality of fluorescent nanoparticles has an average diameter of less than about 30 nm as measured by dynamic light scattering.

6. The lyophilized composition of claim 1, wherein the plurality of fluorescent nanoparticles has an average diameter of between 30 nm and 100 nm as measured by dynamic light scattering.

7. The lyophilized composition of claim 1, wherein the plurality of fluorescent nanoparticles has an average diameter of less than about 100 nm as measured by dynamic light scattering.

8. The lyophilized composition of claim 1, wherein the plurality of fluorescent nanoparticles after lyophilization comprises a similar or increased quantum yield when dispersed in an aqueous solution as compared to the plurality of fluorescent nanoparticles prior to lyophilization.

9. The lyophilized composition of claim 1, wherein at least some fluorescent nanoparticles in the plurality of fluorescent nanoparticles are conjugated to a biomolecule.

10. The lyophilized composition of claim 9, wherein the biomolecule is a protein, a nucleic acid molecule, a lipid, or a peptide.

11. The lyophilized composition of claim 9, wherein the biomolecule is an antibody or an aptamer.

12. The lyophilized composition of claim 1, wherein each fluorescent nanoparticle in the plurality of fluorescent nanoparticles comprises a plurality of polymers.

13. The lyophilized composition of claim 1, wherein the plurality of fluorescent nanoparticles after lyophilization have a similar average particle diameter when dispersed in an aqueous solution as compared to the average particle diameter of the plurality of fluorescent nanoparticles prior to lyophilization.

14. The lyophilized composition of claim 1, wherein the at least one condensed conjugated, semiconducting polymer is selected from the group consisting of a fluorene polymer, a phenylene vinylene polymer, a phenylene ethynylene polymer, a BODIPY polymer, and any derivative thereof.

15. A kit comprising:
   a composition comprising a lyophilized lyophilization agent that comprises a carbohydrate and a plurality of lyophilized fluorescent nanoparticles, wherein:
      each lyophilized fluorescent nanoparticle in the plurality comprises at least one condensed conjugated, semiconducting polymer; and
      the plurality of lyophilized fluorescent nanoparticles after lyophilization has a quantum yield that is greater than 80% of the quantum yield of the plurality of fluorescent nanoparticles that have not been lyophilized; and
   a set of instructions describing combining the composition with an aqueous solution,
   wherein the lyophilized lyophilization agent is present between about 1% w/v and 50% w/v.

16. The kit of claim 15, wherein the lyophilized lyophilization agent further comprises an alditol, hydroxypropyl-cyclodextrin, BSA, or any combination thereof.

17. The kit of claim 15, wherein at least some fluorescent nanoparticles in the plurality of fluorescent nanoparticles are conjugated to a biomolecule.

18. The kit of claim 15, wherein the at least one condensed conjugated, semiconducting polymer is selected from the group consisting of a fluorene polymer, a phenylene vinylene polymer, a phenylene ethynylene polymer, a BODIPY polymer, and any derivative thereof.

19. The lyophilized composition of claim 1, wherein the at least one condensed conjugated, semiconducting polymer comprises a narrow-band emissive unit.

20. The lyophilized composition of claim 19, wherein the narrow-band emissive unit is covalently attached to the at least one condensed conjugated, semiconducting polymer.

21. The lyophilized composition of claim 19, wherein the narrow-band emissive unit comprises a BODIPY monomer, a squaraine monomer, a metal complex, a porphyrin, a phthalocyanine, a lanthanide complex, a perylene, a cyanine, a rhodamine, a coumarin, a xanthene, or any derivative thereof.

22. The lyophilized composition of claim 14, wherein the at least one condensed conjugated, semiconducting polymer is a copolymer.

* * * * *